(12) United States Patent
Tehrani et al.

(10) Patent No.: US 10,966,693 B2
(45) Date of Patent: *Apr. 6, 2021

(54) DIAGNOSIS AND TREATMENT OF TISSUE

(71) Applicant: Precision Biopsy, Inc., Aurora, CO (US)

(72) Inventors: Amir Tehrani, San Francisco, CA (US); Edward A. Jasion, San Diego, CA (US)

(73) Assignee: THE REGENTS OF THE UNIVERSITY OF COLORADO, Denver, CO (US)

(*) Notice: Subject to any disclaimer, the term of this patent is extended or adjusted under 35 U.S.C. 154(b) by 309 days.

This patent is subject to a terminal disclaimer.

(21) Appl. No.: 16/030,521

(22) Filed: Jul. 9, 2018

(65) Prior Publication Data

US 2019/0000430 A1    Jan. 3, 2019

Related U.S. Application Data

(63) Continuation of application No. 15/804,042, filed on Nov. 6, 2017, now Pat. No. 10,016,185, which is a
(Continued)

(51) Int. Cl.
*A61B 10/04* (2006.01)
*A61B 5/00* (2006.01)
(Continued)

(52) U.S. Cl.
CPC ............ *A61B 10/04* (2013.01); *A61B 1/0016* (2013.01); *A61B 1/043* (2013.01); *A61B 1/0684* (2013.01);
(Continued)

(58) Field of Classification Search
CPC . A61B 10/0241; A61B 10/04; A61B 17/3403; A61B 18/1477; A61B 18/22;
(Continued)

(56) References Cited

U.S. PATENT DOCUMENTS

| 4,930,516 A | 6/1990 | Alfano et al. |
| 5,042,494 A | 8/1991 | Alfano |

(Continued)

FOREIGN PATENT DOCUMENTS

| EP | 1559363 A2 | 8/2005 |
| WO | 96/03923 A1 | 2/1996 |

(Continued)

OTHER PUBLICATIONS

Bigio, Irving J. et al., Ultraviolet and visible spectroscopies for tissue diagnostics: fluorescence spectroscopy and elastic-scattering spectroscopy, Phys. Med. Biol. 42 (1997) 803-814.

(Continued)

*Primary Examiner* — Michael T Rozanski
(74) *Attorney, Agent, or Firm* — Dorsey & Whitney LLP

(57) ABSTRACT

A method of evaluating an image indicating a potential presence of a cancer lesion at a location within a prostate of a patient by transmitting light from an optical probe toward a location, receiving fluorescence spectra by the optical probe from the location, and generating a visual display of a diagnosis classification so as to confirm or contradict the existence of the cancer lesion at the location.

16 Claims, 37 Drawing Sheets

Related U.S. Application Data continuation of application No. 15/202,860, filed on Jul. 6, 2016, now Pat. No. 9,814,449, which is a continuation-in-part of application No. 14/400,942, filed as application No. PCT/US2013/041858 on May 20, 2013, now Pat. No. 9,814,448, which is a continuation-in-part of application No. 13/898,062, filed on May 20, 2013, now abandoned.

(60) Provisional application No. 61/649,694, filed on May 21, 2012, provisional application No. 62/189,542, filed on Jul. 7, 2015.

(51) Int. Cl.

| | | |
|---|---|---|
| *A61B 10/02* | (2006.01) | |
| *A61B 17/34* | (2006.01) | |
| *A61B 6/12* | (2006.01) | |
| *A61B 8/08* | (2006.01) | |
| *A61B 1/00* | (2006.01) | |
| *A61B 1/04* | (2006.01) | |
| *A61B 8/12* | (2006.01) | |
| *A61B 1/06* | (2006.01) | |
| *A61B 1/07* | (2006.01) | |
| *A61B 8/00* | (2006.01) | |
| *A61B 5/06* | (2006.01) | |
| *A61B 90/11* | (2016.01) | |
| *A61B 90/00* | (2016.01) | |
| *A61B 90/30* | (2016.01) | |
| *A61B 34/20* | (2016.01) | |
| *A61B 1/307* | (2006.01) | |
| *A61B 6/03* | (2006.01) | |
| *A61B 18/14* | (2006.01) | |
| *A61B 18/22* | (2006.01) | |
| *A61B 17/00* | (2006.01) | |
| *A61B 18/02* | (2006.01) | |
| *A61B 18/04* | (2006.01) | |
| *A61N 5/06* | (2006.01) | |
| *A61N 5/10* | (2006.01) | |
| *A61N 7/02* | (2006.01) | |

(52) U.S. Cl.
CPC .............. *A61B 1/07* (2013.01); *A61B 5/0035* (2013.01); *A61B 5/0036* (2018.08); *A61B 5/0071* (2013.01); *A61B 5/0073* (2013.01); *A61B 5/0075* (2013.01); *A61B 5/0084* (2013.01); *A61B 5/061* (2013.01); *A61B 5/4381* (2013.01); *A61B 5/4836* (2013.01); *A61B 5/6848* (2013.01); *A61B 6/12* (2013.01); *A61B 8/0841* (2013.01); *A61B 8/12* (2013.01); *A61B 8/461* (2013.01); *A61B 10/0241* (2013.01); *A61B 17/3403* (2013.01); *A61B 90/11* (2016.02); *A61B 1/0638* (2013.01); *A61B 1/307* (2013.01); *A61B 5/6835* (2013.01); *A61B 6/032* (2013.01); *A61B 18/1477* (2013.01); *A61B 18/22* (2013.01); *A61B 2010/045* (2013.01); *A61B 2017/00274* (2013.01); *A61B 2017/3411* (2013.01); *A61B 2017/3413* (2013.01); *A61B 2018/0293* (2013.01); *A61B 2018/048* (2013.01); *A61B 2034/2055* (2016.02); *A61B 2034/2063* (2016.02); *A61B 2090/309* (2016.02); *A61B 2090/364* (2016.02); *A61B 2090/3614* (2016.02); *A61B 2090/373* (2016.02); *A61B 2090/3782* (2016.02); *A61B 2562/046* (2013.01); *A61N 5/062* (2013.01); *A61N 5/1001* (2013.01); *A61N 5/1027* (2013.01); *A61N 7/022* (2013.01); *A61N 2005/0612* (2013.01)

(58) Field of Classification Search
CPC ..... A61B 1/0016; A61B 1/043; A61B 1/0638; A61B 1/0684; A61B 1/07; A61B 1/307; A61B 2010/045; A61B 2017/00274; A61B 2017/3411; A61B 2017/3413; A61B 2018/0293; A61B 2018/048; A61B 2034/2055; A61B 2034/2063; A61B 2090/309; A61B 2090/3614; A61B 2090/364; A61B 2090/373; A61B 2090/3782; A61B 2562/046; A61B 5/0035; A61B 5/0036; A61B 5/0071; A61B 5/0073; A61B 5/0075; A61B 5/0084; A61B 5/061; A61B 5/4381; A61B 5/4836; A61B 5/6835; A61B 5/6848; A61B 6/032; A61B 5/12; A61B 8/0841; A61B 8/12; A61B 8/461; A61B 90/11; A61N 2005/0612; A61N 5/062; A61N 5/1001; A61N 5/1027; A61N 7/022
See application file for complete search history.

(56) References Cited

U.S. PATENT DOCUMENTS

| | | |
|---|---|---|
| 5,131,398 A | 7/1992 | Alfano et al. |
| 5,280,788 A | 1/1994 | Janes et al. |
| 5,318,023 A | 6/1994 | Vari et al. |
| 5,368,045 A | 11/1994 | Clement et al. |
| 5,983,125 A | 11/1999 | Alfano et al. |
| 6,124,358 A | 9/2000 | Estanove et al. |
| 6,167,297 A | 12/2000 | Benaron |
| 6,174,291 B1 | 1/2001 | McMahon et al. |
| 6,205,353 B1 | 3/2001 | Alfano et al. |
| 6,405,074 B1 | 6/2002 | Banerjee |
| 6,485,413 B1 | 11/2002 | Boppart et al. |
| 6,564,087 B1 | 5/2003 | Pitris et al. |
| 6,760,613 B2 | 7/2004 | Nordstrom et al. |
| 8,406,858 B2 | 3/2013 | Werahera et al. |
| 9,814,448 B2 | 11/2017 | Werahera et al. |
| 9,814,449 B2 | 11/2017 | Tehrani et al. |
| 10,016,185 B2 * | 7/2018 | Tehrani ............... A61B 5/4836 |
| 2002/0026127 A1 | 2/2002 | Balbierz et al. |
| 2002/0082518 A1 | 6/2002 | Weiss et al. |
| 2002/0143243 A1 | 10/2002 | Georgakoudi et al. |
| 2003/0041041 A1 | 2/2003 | Cristianini |
| 2003/0055341 A1 | 3/2003 | Banerjee |
| 2003/0135122 A1 | 7/2003 | Bambot et al. |
| 2003/0162301 A1 | 8/2003 | Noergaard et al. |
| 2006/0139633 A1 | 6/2006 | Puppels et al. |
| 2006/0173359 A1 | 8/2006 | Lin et al. |
| 2007/0075226 A1 | 4/2007 | Engstrand |
| 2008/0194969 A1 | 8/2008 | Werahera et al. |
| 2010/0198080 A1 | 8/2010 | Liu et al. |
| 2010/0228238 A1 | 9/2010 | Brennan et al. |
| 2010/0331782 A1 | 12/2010 | Hendriks et al. |
| 2011/0319759 A1 | 12/2011 | Liu et al. |
| 2012/0071749 A1 | 3/2012 | Xu et al. |
| 2012/0245473 A1 | 9/2012 | Mycek et al. |
| 2013/0310680 A1 | 11/2013 | Werahera et al. |
| 2014/0213911 A1 | 7/2014 | Bierhoff et al. |
| 2015/0150459 A1 | 6/2015 | Werahera et al. |

FOREIGN PATENT DOCUMENTS

| | | |
|---|---|---|
| WO | 98/27965 | 7/1998 |
| WO | 2004/041060 A3 | 5/2004 |
| WO | 2005/092194 A1 | 10/2005 |
| WO | 2006/119166 A2 | 11/2006 |
| WO | 2009/109873 A1 | 9/2009 |
| WO | 2009/144653 A2 | 12/2009 |

(56) References Cited

FOREIGN PATENT DOCUMENTS

| WO | 2011066149 A1 | 6/2011 |
|----|---------------|--------|
| WO | 2011093108 A1 | 8/2011 |

OTHER PUBLICATIONS

Crawford, E. David et al., Clinical staging of prostate cancer: a computer-simulated study of transperineal prostate biopsy, (2005) BJU International 96, 999-1004.

Palmer, Gregory M. et al., Autofluorescence Spectroscopy of Normal and Malignant Human Breast Cell Lines, Photochemistry and Photobiology, 2003, 78(5), 462-469.

Palmer, Gregory M. et al., Comparison of Multiexcitation Fluorescence and Diffuse Reflectance Spectroscopy for the Diagnosis of Breast Cancer, IEEE Transactions on Biomedical Engineering, vol. 50, No. 11, Nov. 2003, pp. 1233-1242.

Ramanujam, Nirmala, Fluorescence Spectroscopy of Neoplastic and Non-Neoplastic Tissues, Neoplasia, vol. 2, Nos. 1-2, Jan.-Apr. 2000, pp. 89-117.

Utzinger, Urs et al., Fiber optic probes for biomedical optical spectroscopy, Journal of Biomedical Optics, Jan. 2003, vol. 8, No. 1, pp. 121-147.

Werahera, Priya N. et al., Biomorphometric Analysis of Human Prostatic Carcinoma by Using Three-Dimensional Computer Models, Human Pathology, vol. 35, No. 7 (Jul. 2004), pp. 798-807.

Crawford, E. David et al., Computer Modeling of Prostate Biopsy: Tumor Size and Location—Not Clinical Significance—Determine Cancer Detection, The Journal of Urology, vol. 159, pp. 1260-1264 (Apr. 1998).

Kuo, Wei-Cheng et al., Real-time three-dimensional optical coherence tomography image-guided core-needle biopsy system, Biomedical Optics Express, vol. 3, No. 6, Jun. 1, 2012, pp. 1149-1161.

Peikari, Mohammad et al., Characterization of ultrasound elevation beamwidth artifacts for prostate brachytherapy needle insertion, Medical Physics, vol. 39, No. 1, Jan. 2012, pp. 246-256.

Extended European Search Report dated Jan. 27, 2016 relating to European Patent Application No. 13794535.8, 14 pages.

* cited by examiner

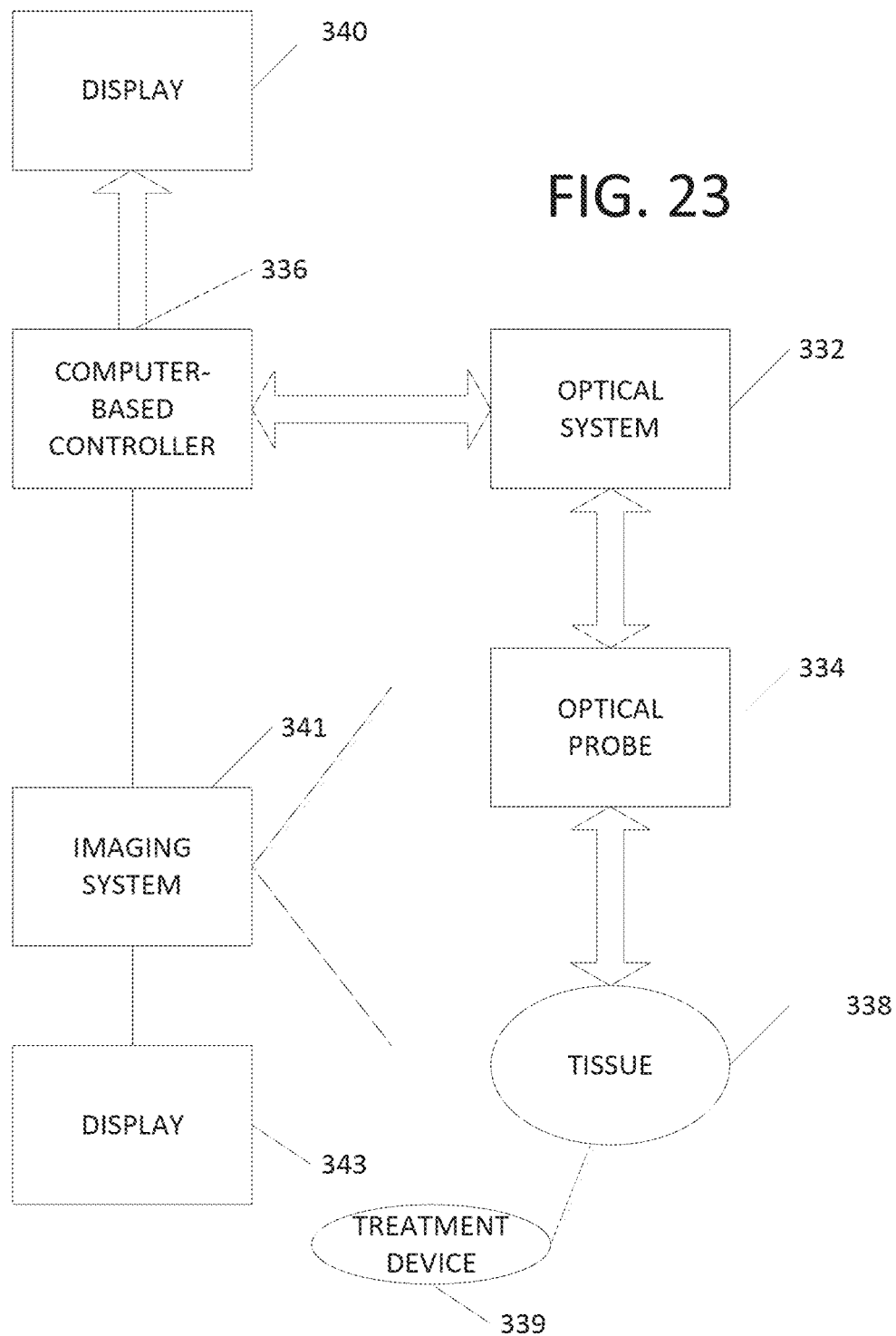

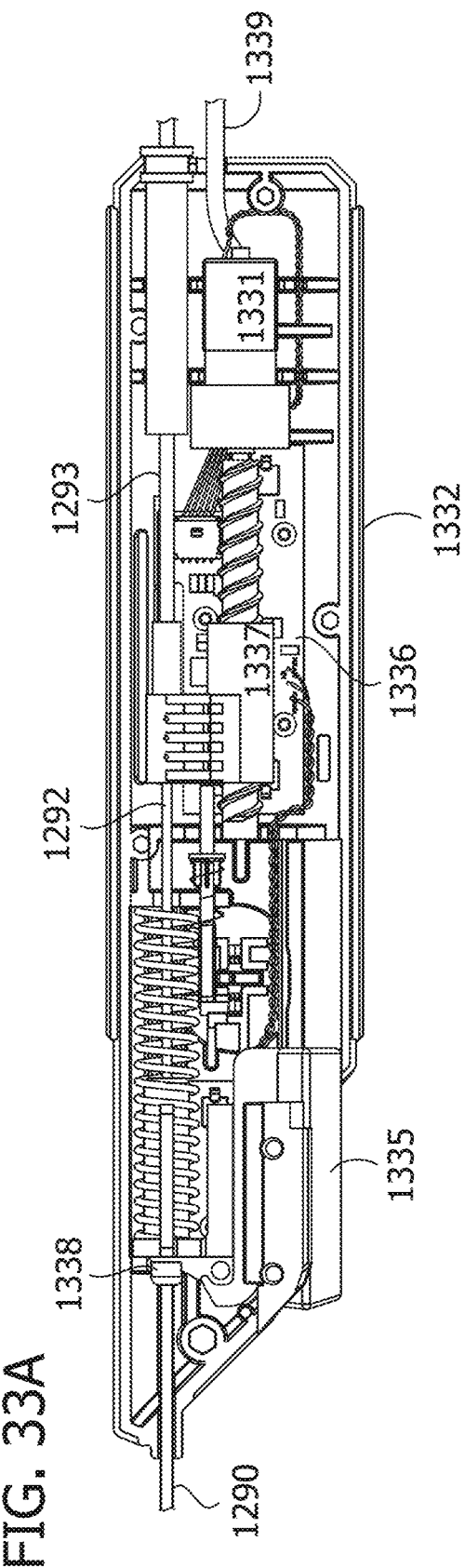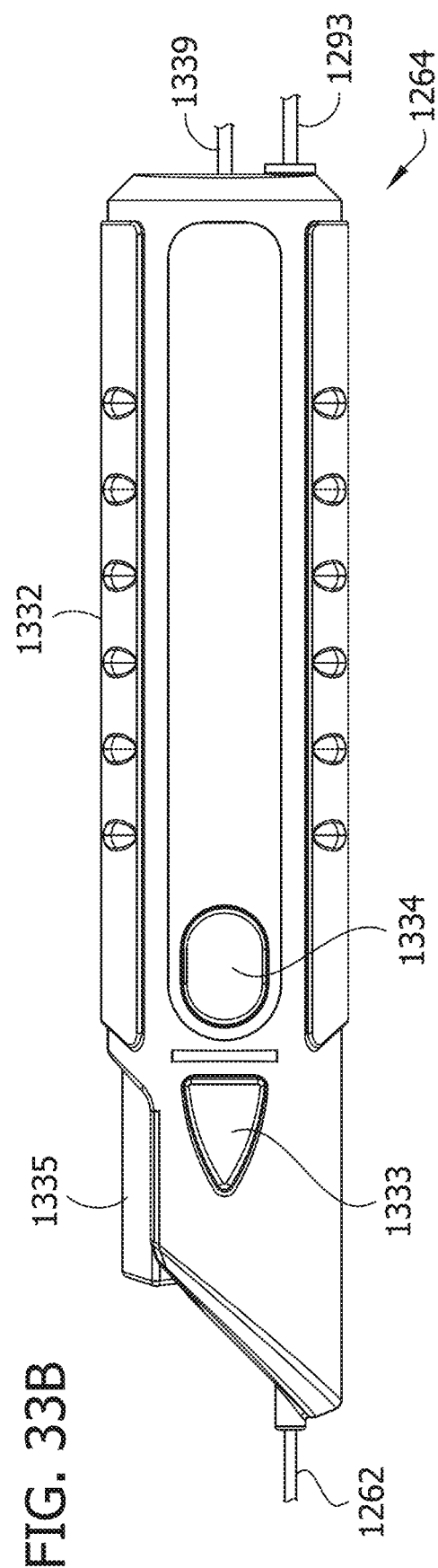
FIG. 33A
FIG. 33B

DIAGNOSIS AND TREATMENT OF TISSUE

REFERENCE TO RELATED APPLICATIONS

This application is a continuation of U.S. application Ser. No. 15/804,042 filed on Nov. 6, 2017 (issued as U.S. Pat. No. 10,016,185), which is a continuation of U.S. application Ser. No. 15/202,860 filed on Jul. 6, 2016 (issued as U.S. Pat. No. 9,814,449), which is continuation-in-part of U.S. national stage application Ser. No. 14/400,942, filed Nov. 13, 2014 (issued as U.S. Pat. No. 9,814,448), of International Patent Application No. PCT/US2013/041858, filed May 20, 2013, which claims the benefit of U.S. Provisional Application No. 61/649,694, filed May 21, 2012, the entire disclosures of which are incorporated herein by reference; and application Ser. No. 14/400,942 is a continuation-in-part of U.S. application Ser. No. 13/898,062 filed on May 20, 2013, which claims the benefit of U.S. Provisional Application No. 61/649,694, filed May 21, 2012, the entire disclosures of which are incorporated herein by reference; and U.S. application Ser. No. 15/202,860 claims the benefit of U.S. Provisional Application No. 62/189,542, filed Jul. 7, 2015, the entire disclosures of which are incorporated herein by reference.

SUMMARY

In one form, a method of evaluating an image indicating a potential presence of a cancer lesion at a location within a prostate of a patient comprises positioning an optical probe so as to target the location within the prostate of the patient; transmitting light from the optical probe toward the location and receiving fluorescence spectra by the optical probe from the location which is utilized by a tissue classification system having at least one algorithm that generates a diagnosis classification based only on selected data of the fluorescence spectra; and generating a visual display of the diagnosis classification at the location overlapping the image so as to confirm or contradict the existence of the cancer lesion at the location.

BRIEF DESCRIPTION OF THE DRAWINGS

FIG. 1 is schematic representation of a transverse view plus ultrasound image of an array of cryoneedles, and FIG. 2 is an ultrasound image of a longitudinal view of FIG. 1 showing an array of cryoneedles (striated).

FIG. 5B is provided to illustrate some of the details of FIG. 5A.

FIG. 23 illustrates in block diagram form one embodiment of an optical system connected to an optical probe and a computer controller executing user interface software and a tissue classification algorithm, in combination with an imaging system.

FIG. 33A illustrates in one form a side view of the interior of the Handle housing showing the stepper motor for auto-advancing the inner needle in 1 mm increments up to 22 mm. The cannula through which the inner needle passes is mechanically driven by a spring, and manually retracted and released. The cannula can also be retracted and released automatically via a combination of being driven by a motor or spring and controlled by computer.

FIG. 33B illustrates in one form a plan side view of the Handle showing the various buttons.

DETAILED DESCRIPTION

Figure 1:
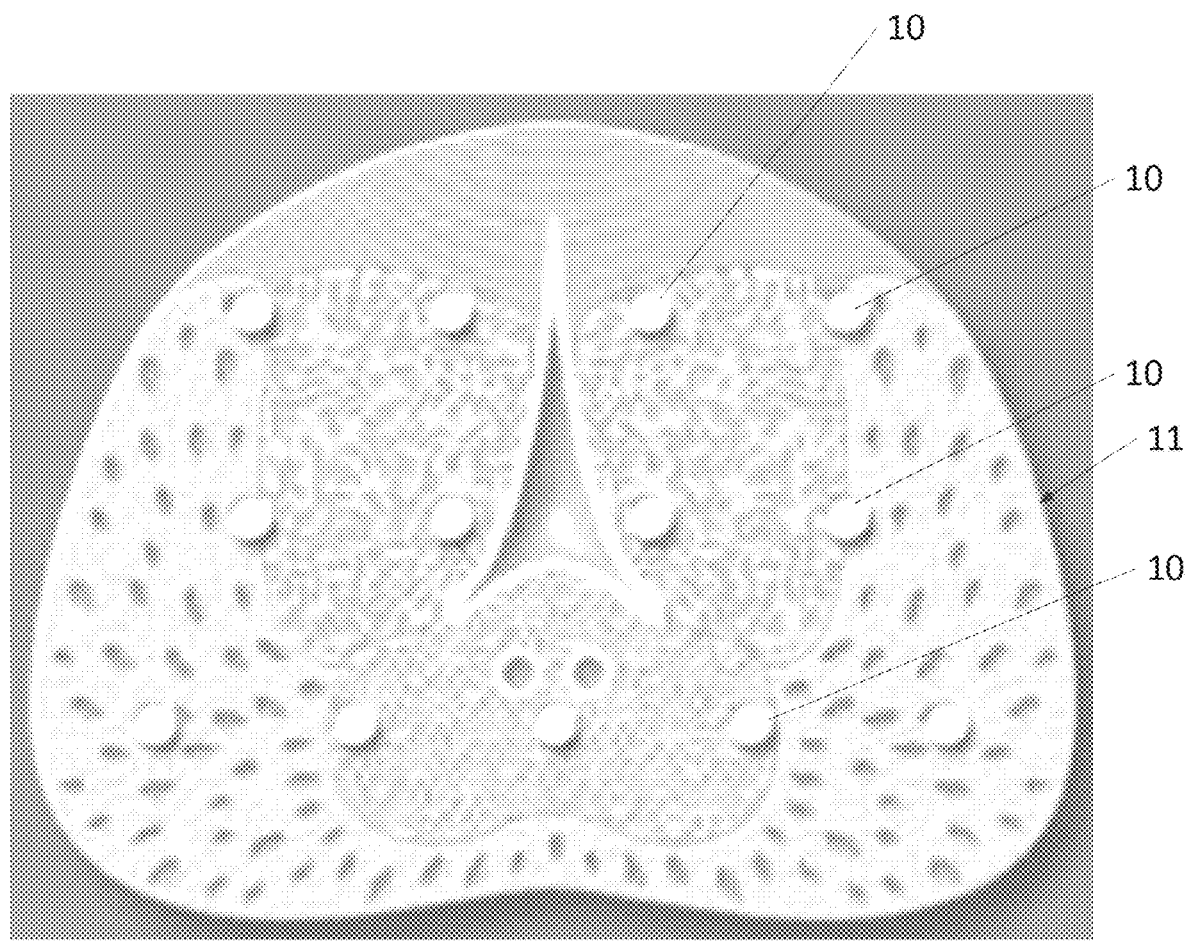
FIGS. 1 and 2 illustrate positioning of the cryoneedles within prostate tissue for either whole-gland therapy or focal therapy purposes.

The American Cancer Society estimates that in the United States in 2013, 238,590 new cases of prostate cancer (PCa) will be diagnosed compared with approximately 99,000 cases diagnosed in 1988 attributable to the advent of prostate-specific antigen (PSA) screening. Consequently, there has been stage migration with earlier stage at diagnosis. Presently, 92% of incident PCa are locoregional versus metastatic. Hence, only 29,720 men are estimated to die from this disease in 2013. Accurate staging before treatment is desirable given the relatively high number of men who must be treated to prevent PCa-specific death. PCa has a long latency period and consequently more men die with rather than from this disease. Hence, a significant proportion of US men with localized PCa are overdiagnosed and overtreated with attendant morbidity and significant cost escalations as insignificant tumors were detected via aggressive screening procedures.

Transrectal ultrasound (TRUS) guided tissue biopsy of the prostate is the current method of screening for PCa. Pathological examination of tissue needs to confirm the presence of the disease. However, prostate biopsies are subjected to serious sampling errors and frequently miss aggressive PCa that warrant definitive therapy during initial screenings. The PCa detection rate according to the current standard of care for TRUS-guided needle biopsies with 10-12 biopsy cores is only 25-30%, while more than 50% of cancers that require definitive treatment remain undetected during initial biopsies. Such undetected cancers due to false negative biopsies are at risk of spreading beyond the prostate gland and metastasizing to distant sites. Even when PCa were diagnosed by prostate biopsies, they may fail to provide accurate information regarding histologic grade and stage of the disease that are needed for therapeutic decisions. Aggressive PCa lesions may be differentiated from non-aggressive or latent PCa based on histologic grade, pathologic stage, and volume. Aggressive PCa for organ-confined disease may be defined as those tumors with volume≥0.5 cc or Gleason[8] sum≥7.

An optical probe array (e.g., a needle having an integrated optical sensor at its tip) is used in combination with an image guiding system (e.g., an ultrasound system) and/or in combination with an imaging system (e.g., fluorescence and/or diffuse reflectance spectroscopy) to obtain in vivo optical spectroscopically-guided prostate analysis and/or treatment. This enables one to sample and diagnostically classify different types of tissue within the prostate. The optical probes interface with a device, such as a fluorometer or fluorescence spectroscope, used to measure light parameters, such as fluorescence. In one embodiment, software to control a fluorometer, an optical data acquisition device, a user interface, and a tissue classification system resides on a laptop computer. In one configuration, the fluorometer comprises two light sources with peak emissions respectively at 280-290 and 340 nm, one broadband light source 500-1000 nm and a spectrometer (e.g., CCD-based (charge coupled device), PMT-based (photon multiplier tube), etc.). Systematic application of this technology uses optical measurements to indicate presence of cancer or other abnormal tissue within the prostate permitting determination of highest histologic grade and stage of the disease at the time of biopsy and permitting targeted treatment. In addition, based on the number of positive cores and percentage core involvement, embodiments provide information regarding size (volume), location, and distribution of PCa. In at least some situations this information can be combined to determine if a patient has aggressive disease or not and hence to customize therapeutic options to meet the needs of each patient.

Embodiments significantly improve diagnosis, staging, and therapy of PCa involving the following: 1) Accurate diagnosis and localization of PCa lesions using a TRUS-guided standard biopsy, MR/Fusion biopsy, saturation biopsy, or brachytherapy template-guided mapping biopsy using optical biopsy needle and associated technology, 2) Determine whether patient has aggressive PCa based on histopathological grade, pathologic stage, number of positive cores, and percentage core involvement, 3) Personalized therapy and when applicable adjunct with an optical probe and associated technology, and 4) Monitor response during therapy and progress following therapy. Based on histopathological findings from biopsy tissue, patients with aggressive PCa lesions that require definitive, potentially curative treatment which may include surgery, radiation, and neoadjuvant therapy can be identified. The aim of neoadjuvant therapy is to maximize cure rates for patients who have undergone definitive therapy for localized disease, theoretically by eliminating micrometastatic disease. Patients assessed to have non-aggressive disease may be candidates for watchful-waiting (WW) or active surveillance (AS). We believe this approach is a vital step to minimize overtreatment of PCa according to the current standard of care since 5 out of 6 men diagnosed with PCa may be candidates for WW or AS. It will also lead to early diagnosis of clinically important cancer and gives an opportunity to intervene where therapy benefits the patient.

Figure 2:
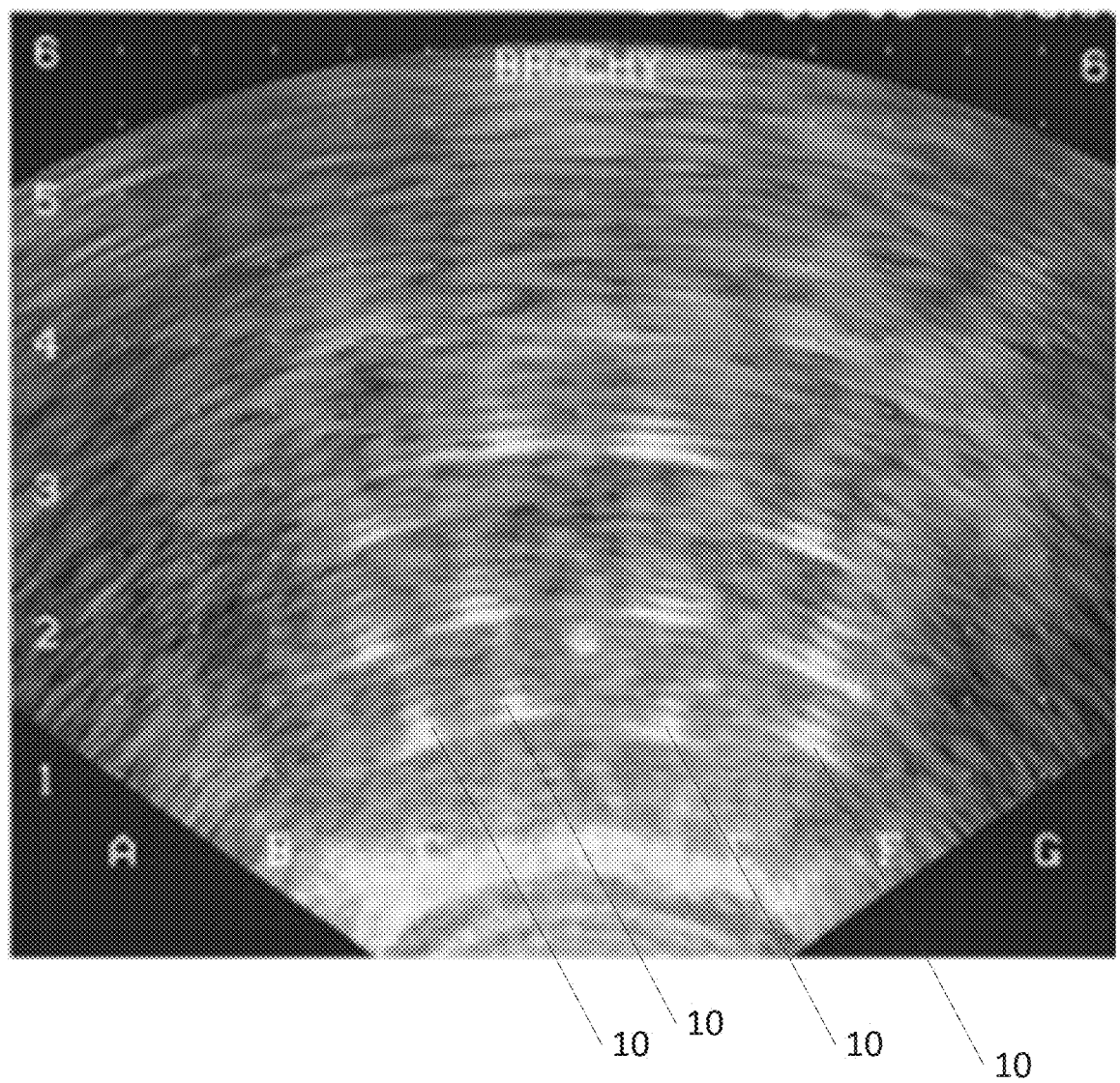

Definitive whole-gland therapy for PCa has serious side effects including erectile dysfunction (ED) and urinary incontinence. The concept of "highly selective" ablative procedures or targeted focal therapy (TFT) for PCa is being considered in certain low-risk patients. During TFT, therapeutic agent is targeted directly onto each PCa lesion or regions within the prostate instead of the entire gland. This option would hypothetically result in a significant decrease in the morbidity associated with PCa treatment, particularly ED. The process of TFT includes careful three-dimensional (3D) mapping of PCa lesions within the prostate gland followed by focused targeted treatment to only those lesions or regions where PCa lesions are located. However, screening patients for this procedure is a challenge. Further, guiding treatment based on TRUS-guided biopsy findings is difficult due to prostate movement and deformation or warping. Using 3D computer models of autopsy prostates with previously undetected carcinomas, it has been proven that transperineal mapping biopsy (TMB) as the method to identify patients with low-risk PCa for TFT (e.g., positioning of cryoneedles 10 within prostate tissue 11 following transperineal mapping biopsy procedure). FIG. 1 is schematic representation of a transverse view, and FIG. 2 is an ultrasound image of a longitudinal view of an array of cryoneedles (striated) 10.

In one embodiment, a 5-mm grid transperineal mapping biopsy consistently sampled the highest Gleason grade 4/5 tumors and detected aggressive PCa with sensitivity, specificity, positive predictive value (PPV), and negative predictive value (NPV) of 95%, 30%, 31%, and 95%, respectively. Specificity and positive predictive value were lower since the transperineal mapping biopsy detected a higher proportion of clinically insignificant PCa lesions.

By combining an optical biopsy needle and/or an optical probe with transperineal mapping biopsy, similar diagnostic information regarding tumor locations and tumor distribution can be obtained enabling therapeutic agents to be directed to these same locations for targeted focal therapy (TFT). This document describes diagnostic and therapeutic modalities based on the optical probe and associated technologies for TFT for low risk PCa cancer patients sparing them serious side-effects associated with definitive therapies such as surgery and radiation.

Therapeutic Modalities

Cryotherapy:

Cryoablation of the prostate may be used to treat localized prostate cancer or recurrences after previous treatments. Cryoablation of the prostate may be done through total freezing of the prostate. Alternatively, cryoablation may be restricted to focal or regional freezing to treat only the involved areas of the prostate as in TFT. In this manner the nerves for erection sitting on the uninvolved part of the prostate may remain intact to preserve erections. Cryotherapy has been performed worldwide for over 50 years. The American and European Association of Urology guidelines on prostate cancer state that cryotherapy is a true therapeutic alternative for patients with clinically localized prostate cancer. The American Association of Urology recently made an announcement of a best practice statement confirming cryotherapy as a valid treatment option for both primary and recurrent localized prostate cancer. In 2005 in the UK, the National Institute of Clinical Excellence approved the use of cryotherapy for patients with prostate cancer, both as a primary treatment and as salvage treatment after radiotherapy or hormone therapy.

Cryotherapy causes cell death through two principle mechanisms. First, as the temperature falls, extracellular ice crystallizes causing movement of water from the intracellular to the extracellular environment after an osmotic gradient. As the temperature continues to fall, intracellular ice crystals form, causing direct damage to the intracellular organelle system and the cell membrane. The second mechanism is platelet aggregation and microthrombus formation in small blood vessels, which leads to ischemic change in the tissue area supplied by the affected blood vessels. These changes lead to coagulative necrosis and cause a well demarcated lesion. In addition, severe temperature changes and ischemic change induce apoptosis in cells at the periphery of the cryolesion.

The effectiveness of the cellular destruction depends on rapid freezing, the lowest temperature reached, and slow thawing. This is generally achieved through two freeze-thaw cycles to a target temperature of −40° C.

Cryoablation of prostate cancer first took place in 1968 using probes cooled by liquid nitrogen in a closed system. The early technique was associated with considerable complications, such as rectourethral fistulas, urethral sloughing and urinary incontinence. With the introduction of TRUS guidance and the urethral warming catheter, improved results have been achieved. The subsequent development of cryotherapy using 17-gauge needles with echogenic tips has allowed controlled and accurate delivery of the treatment. The current system uses high-pressure argon and helium gas for freezing and warming, respectively. The temperature change is governed by the Joule-Thompson effect, whereby high-pressure gases, when forced though a very small opening into a low-pressure area (within the tip of the cryoneedles), undergo specific temperature changes. This allows the freezing and subsequent thawing of the prostate using the same needle. During the treatment, the temperature in different areas of the prostate is monitored in real time by means of interstitial thermosensors. The needles are placed under TRUS guidance through the skin of the perineum using a brachytherapy template without the need for tract dilatation and with minimal trauma to the patient. As the gas is delivered through the specialized needles, it cools the prostate tissue rapidly to the target temperature of −40° C.

The ice ball is clearly visible on TRUS as it forms and is monitored continuously throughout the procedure. The use of urethral warmer reduces the incidence of urethral sloughing.

Cryotherapy following 3-D mapping of PCa lesions using optical probes with optical sensors and associated system to treat tissue identified in a generated image as noted herein will allow accurate real-time reading and staging of the tumor, directing treatment to the areas affected by PCa (FIGS. 1-2). As noted above, FIGS. 1 and 2 illustrate positioning of the cryoneedles for whole-gland or focal therapy procedure. FIG. 1 is schematic representation of a transverse view plus ultrasound image, and FIG. 2 is an ultrasound image of a longitudinal view of the array of cryoneedles (striated) 10. It should be noted that prostate cancer localization and cryoablation or another form of therapy is not only limited to transperenial procedure. In some embodiments, a TRUS (transrectal ultrasound) system of cancer localization and immediate application of therapy through the mapping or biopsy needle or alternatively an independent catheter is contemplated.

Careful mapping of the prostate can be done using the brachytherapy grid that separates areas of the prostate by 0.5 cm allowing adequate therapeutic ice ball formation. The longitudinal area that will be surveyed by the optical probe will define every 0.5-1.7 cm the presence of PCa cells. The average prostate biopsy core is 1.7 cm and the average length of the prostate is approximately 4 cm.

Ultimately, biopsies will not be needed once correlation between PCa and optical probe is established, allowing intra-operative survey and assessment of tumors to be treated by cryoablation. The result of this work decreases the rate of complications or side effects due to cryotherapy, i.e.; erectile dysfunction, urinary incontinence and rectourethral fistula. TFT with recurrent treatment will be available allowing all procedures to be performed as outpatient basis increasing patient satisfaction and decrease cost of treatment.

Figure 3:
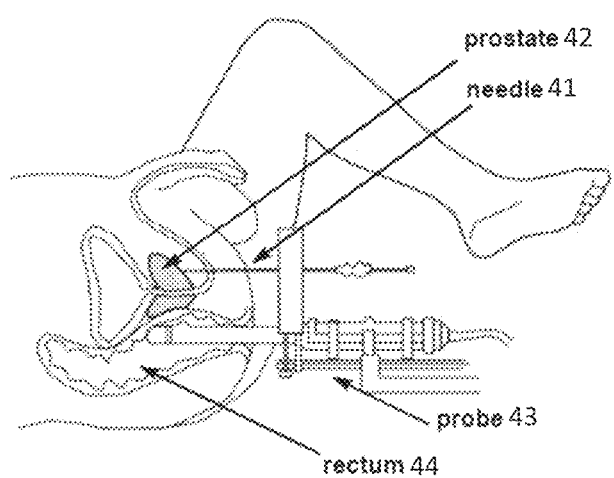
FIG. 3 illustrates strategic placement of a brachytherapy needle, such as to locate radioactive pellets within the prostate.
Figure 4:
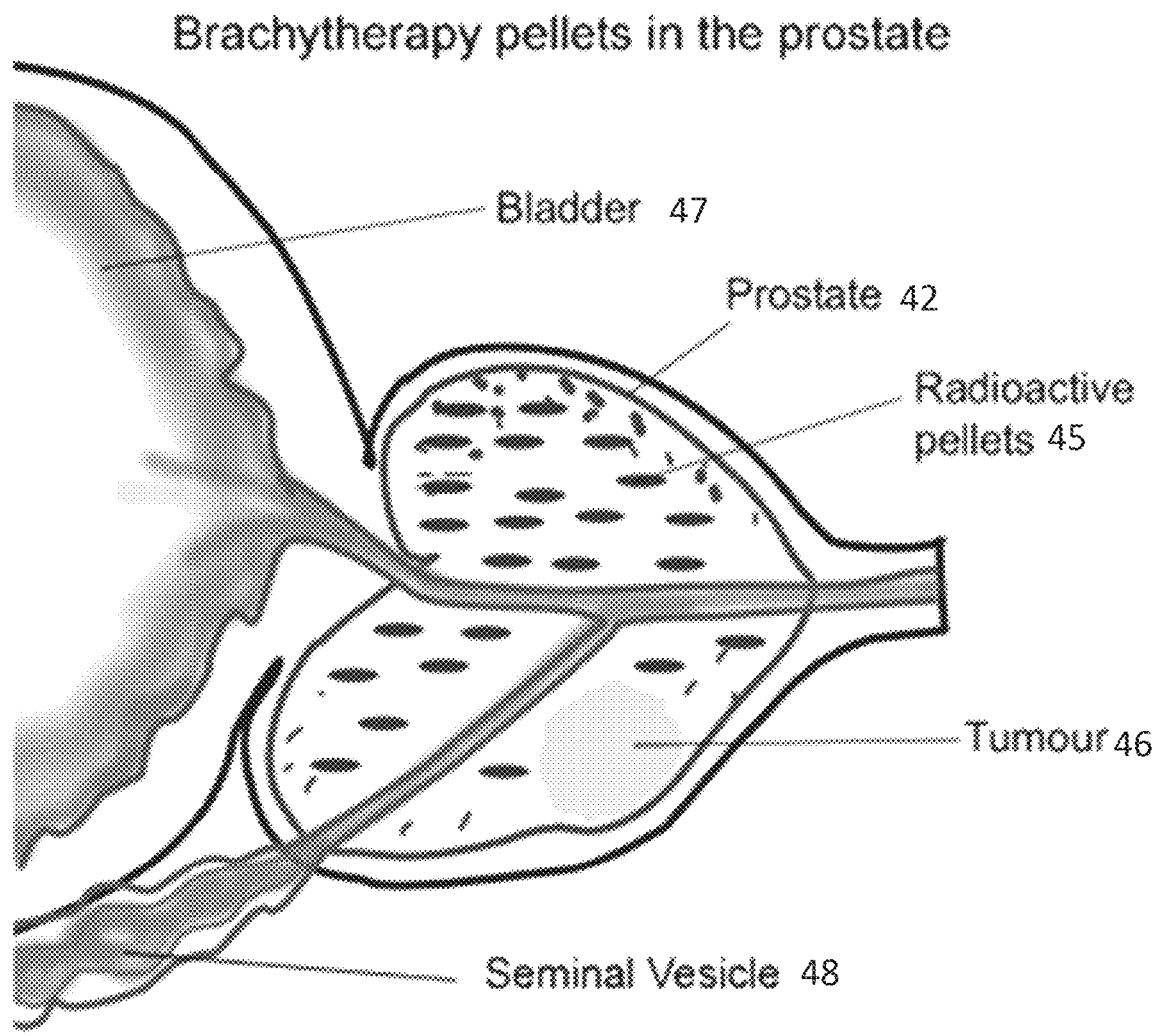
FIG. 4 illustrates brachytherapy in which radioactive pellets have been located within the prostate.

Optical probes will be placed in the prostate using the brachytherapy template. Following identification or confirmation of tumors and tumor margins within the prostate, cryoprobes or brachytherapy needles with radioactive pellets are strategically placed for TFT applications (FIGS. 1-2 for cryotherapy and 3-4 for brachytherapy). For example, FIG. 1 may be a schematic representation of a transverse view plus ultrasound image of strategic placement of cryoprobes, and FIG. 2 is an ultrasound image of a longitudinal view of the array of cryoprobes (striated) 10. For example, FIG. 3 illustrates strategic placement of a brachytherapy needle 41 within a prostate 42, such as to locate radioactive pellets within the prostate 42, under the guidance of an ultrasound probe 43 within the rectum 44. FIG. 4 illustrates brachytherapy in which radioactive pellets 45 have been located within the prostate 42 about a tumor 46 relative to a bladder 47 and relative to a seminal vesicle 48.

Figure 5A:
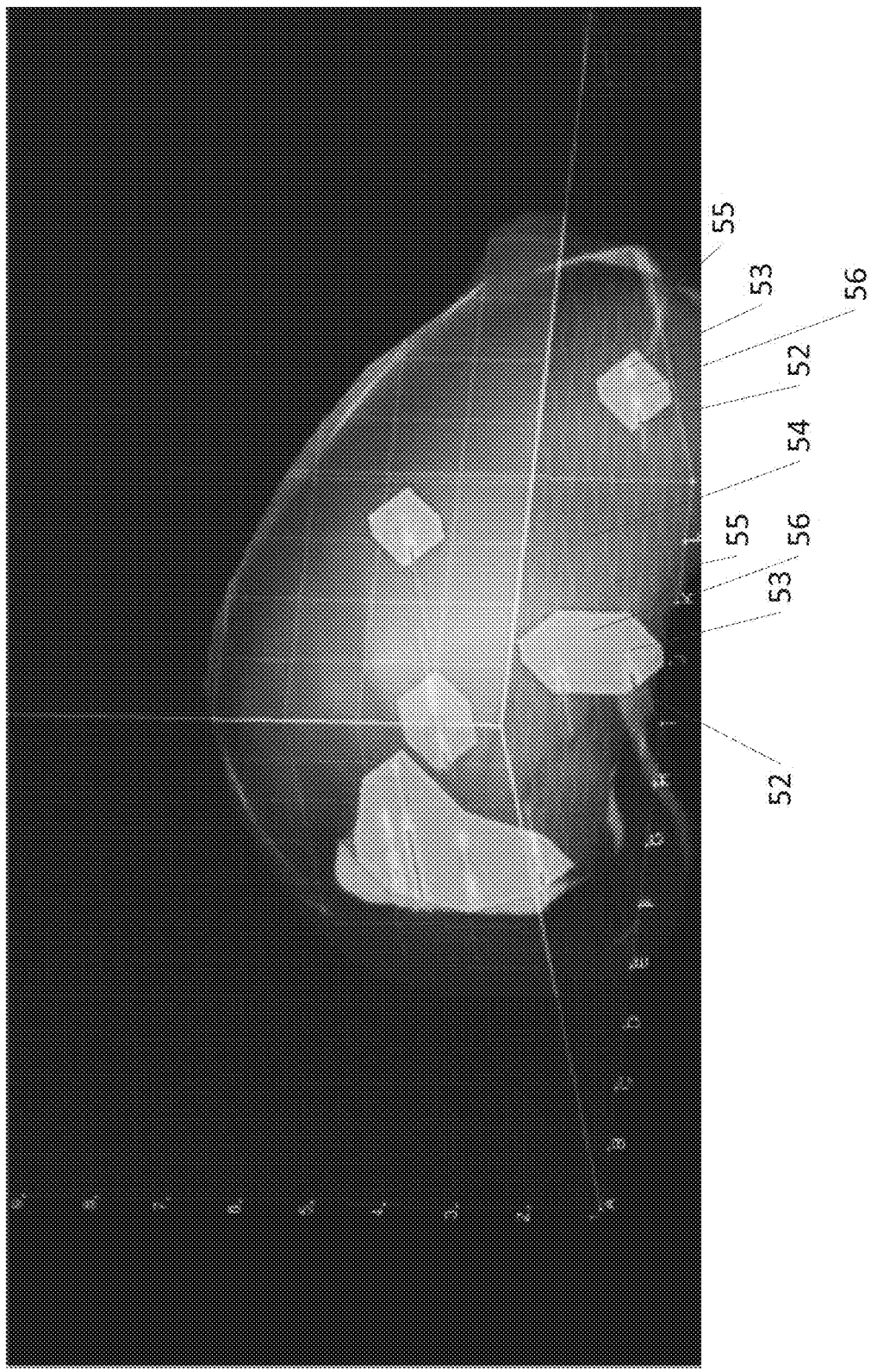
FIG. 5A illustrates a photograph of a three-dimensional (3D) optically mapped image of the prostate following optical measurements identifying locations of prostate cancer lesions according to one embodiment.
Figure 5B:
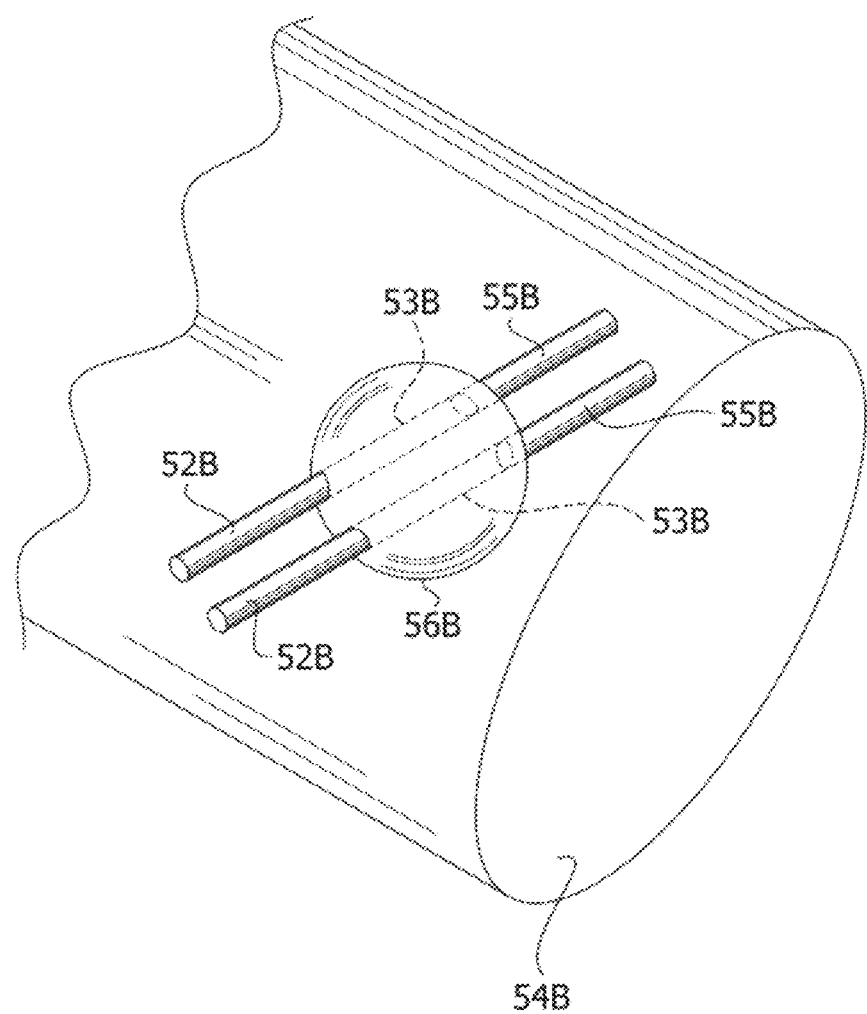
FIG. 5B corresponds to FIG. 5A and illustrates in a simplified line drawing of a perspective view of the three-dimensional (3D) optically mapped image of the prostate shown in FIG. 5A.

FIG. 5A illustrates a photograph of a three-dimensional (3D) optically mapped image of the prostate following optical measurements identifying locations of prostate cancer lesions according to one embodiment. FIG. 5B corresponds to FIG. 5A and illustrates in a simplified line drawing of a perspective view of the three-dimensional (3D) optically mapped image of the prostate shown in FIG. 5A; FIG. 5B is provided to illustrate some of the details of FIG. 5A.

FIG. 5A provides information which can serve as a precursor to a prostate biopsy or to guide therapy. In this context, optical biopsy needles (see needle tracks 52 which are on the near side of lesions 56, needle tracks 53 within the lesions 56, and needle tracks 55 on the far side of the lesions 56) are inserted in to a prostate gland 54 guided by a brachytherapy or another template. This template is located in transperineal direction and 5 mm and 10 mm or other grid points are provided for needle insertions. Optical spectroscopy measurements are obtained in discrete or continuous modes to detect cancer. Each grid coordinate and depth where lesions 56 are located will be recorded for therapeutic applications. Alternatively, lesions 56 may be treated as they are detected by laser ablation or photodynamic therapy using the optical biopsy needle 52.

In FIG. 5B, the partial cylinder 54B is intended to represent a portion of the prostate gland 54 shown in FIG. 5A. The sphere 56B is intended to represent the lesion 56 shown in FIG. 5A. The rods 52B represent the needle tracks 52 which are on the near side of lesion 56 shown in FIG. 5A. The rods 53B shown in phantom represent the needle tracks 53 which are within the lesion 56. The rods 55B represent the needle tracks 55 which are on the far side of lesion 56.

The whole prostate should be surveyed with the optical probe transversally and longitudinally using the TRUS probe in different views and detect continuous read from the optical sensors mounted on the optical probe. Pre-operative measurements of the prostate aid the placement of cryoneedles but also the previous biopsy report with histopathological data may help the surgeon concentrate attention in the areas proven to be positive for PCa.

Embodiments include several modifications to a needle (e.g., a biopsy needle) such as an optical probe with optical sensors, and associated technology to accommodate critical needs in cryotherapy applications including TFT. These embodiments will be discussed in further details herein.

1. Optical probe with multiple sensors separated by 5 mm or at greater or less spacing intervals.
2. Probe with either single or multiple sensors in motorized 2×2 or 3×3 configurations for transperineal forward/backward movement.
3. Optical needles in motorized 2×2 or 3×3 configurations for transperineal forward/backward movement.
4. Hardware and software modifications to fluorometer to accommodate configurations 1 and 2.
5. Above arrangement requires careful mapping of the prostate followed by cryoablation. Alternative configuration may be an integrated optical sensor and cryoneedle to concurrently achieve PCa diagnosis followed by cryoablation of those lesions.

Photodynamic Therapy:

Another minimally invasive treatment modality for PCa patients is photodynamic therapy (PDT). PDT is a treatment that uses photosensitizing drugs; these agents are pharmacologically inactive until they are exposed to near infrared (NIR) light in the presence of oxygen. The activated drug forms reactive oxygen species that are directly responsible for tissue destruction around the area exposed to NIR light. For PCa, the photosensitizers can be administered orally or intravenously, and are activated in the prostate by NIR light of a specific wavelength. This light is produced by a low-power laser or LED, and is delivered to the prostate using optical fibers within transparent plastic needles. The placement of the needles within the prostate is usually guided by transrectal ultrasound and brachytherapy template, and the procedure is normally performed under general anesthetic. Energy is either delivered via a cylindrical diffuser, which emits light along a length of fiber, or via a bare-tipped fiber, where the light comes out of the end only.

The photosensitizing drugs available vary in their modes of action. Some drugs are tissue-based photosensitizers, and take a number of days to reach maximal concentration in the target organ. These drugs tend to accumulate in the skin, where they can be activated by sunlight or artificial room light for a number of weeks after administration; patients who receive these drugs require protection from light until the drug has been completely cleared from the skin. Other photosensitizers are activated in the vasculature; these drugs are activated within minutes of light delivery, and are cleared rapidly. This quick clearance allows the drug and light to be administered in the same treatment session, and avoids the need for prolonged light protection.

Embodiments include several modifications to the optical probe and associated equipment to facilitate PDT for TFT applications to treat tissue identified in a generated image as noted herein:

1. Addition of an LED at NIR range to fluorometer to deliver light to PCa;
2. Modifications to software to facilitate above 1; and
3. Modifications to probe with single or multiple sensors to deliver NIR light to PCa for therapeutic efficacy.

Brachytherapy (See FIG. 4 which illustrates brachytherapy in which pellets have been placed within the prostate): Brachytherapy (the term is derived from the Greek word brachys, which means brief or short) refers to cancer treatment with ionizing radiation delivered via radioactive material placed a short distance from, or within, the tumor. In PCa, brachytherapy involves the ultrasound- and template-guided insertion of radioactive seeds into the gland. Permanent seed brachytherapy, also known as low dose rate brachytherapy, involves having tiny radioactive seeds implanted in the prostate gland. Radiation from the seeds destroys cancer cells in the prostate over time. In addition to permanent brachytherapy, temporary brachytherapy has also been used. In this technique, the implants deliver radiation to the prostate at a higher dose rate than is provided by a permanent implant. Currently, the isotope most commonly used for temporary brachytherapy is iridium (Ir)-192, which provides a higher dose of radiation than the iodine (I)-125 and palladium (Pd)-103 permanent implants. Low dose rate prostate brachytherapy is an effective treatment for localized PCa. Recently, it has been considered for use in a focused manner whereby treatment is targeted only to areas of prostate cancer. The objective of focal brachytherapy for potential TFT applications is to provide effective cancer control for low-risk disease but with reduced genitourinary and rectal side-effects in a cost-effective way. Embodiments include modification to the technology to facilitate focal brachytherapy for TFT applications. At least two configurations can be incorporated to treat tissue identified in a generated image as noted herein:

1. Removable probe with a single sensor coupled with a cannula (outer needle). This is inserted via brachytherapy template until a PCa lesion is located. Sensor is then removed and a radioactive seed is inserted into the outer cannula. It is then pushed via metal tubing to the exact location where PCa lesion is located.
2. Probe with a seed-notch coupled with an outer needle. In this mechanism, radioactive seed is already hidden inside the notch covered by the outer needle. Once the sensor locate PCa lesion, trigger mechanism fires and leave the radioactive seed where PCa lesions is located.

HIFU:

Similar TFT applications may be achieved using high-intensity focused ultrasound (HIFU). HIFU is a treatment that uses ultrasound wave energy focused on the prostate via a transrectal probe to treat tissue identified in a generated image as noted herein. Multiple focal areas of destruction are created within the prostate. The prostate tissue is destroyed through coagulation by the ultrasound wave energy causing rapid heat elevation to about 90° C. at the focal point. An optical biopsy needle and/or an optical needle probe may be used separately or as an integrated device for HIFU treatment of PCa in TFT applications.

AC/DC current for PCa tissue ablation: Tumor efficacy is achieved by passing AC or DC current across PCa tissue by strategically placed electrodes to treat tissue identified in a generated image as noted herein. An optical probe can be used for identification of locations of PCa lesions and thereby enabling strategic placement of the electrodes. In an alternative configuration, both the electrode and optical sensor may be an integrated unit enabling concurrent diagnosis followed by ablation of each PCa lesion.

Laser ablation: Laser ablation could be yet another method to ablate the cancer tissue identified within the prostate once the locations of the cancer lesions are found in a generated image as noted herein. A variety of laser types have been developed for use in medical applications. These lasers may be routed to each PCa lesion using an optical needle probe with either single or multiple sensors.

RF ablation: RF ablation is yet another method to treat the identified cancerous tissue within the prostate gland to treat tissue identified in a generated image as noted herein. RF ablation is currently approved for treatment of BPH (benign prostate hyperplasia) and is commercially available.

Vapor ablation: Vapor ablation is a modality to treat cancer or other type of abnormal tissues within the body such as to treat tissue identified in a generated image as noted herein. Instead of using electrical, laser, or tissue freezing modalities, vapor with high temperature is used to shrink tissue or tumor.

Local drug delivery: once the 3D mapping system has identified the location of cancerous tumor within the prostate, using the same or another needle, drugs and pharmaceutical agents could be delivered as means of treating the cancer locally.

3D Optical Imaging

Figure 6:
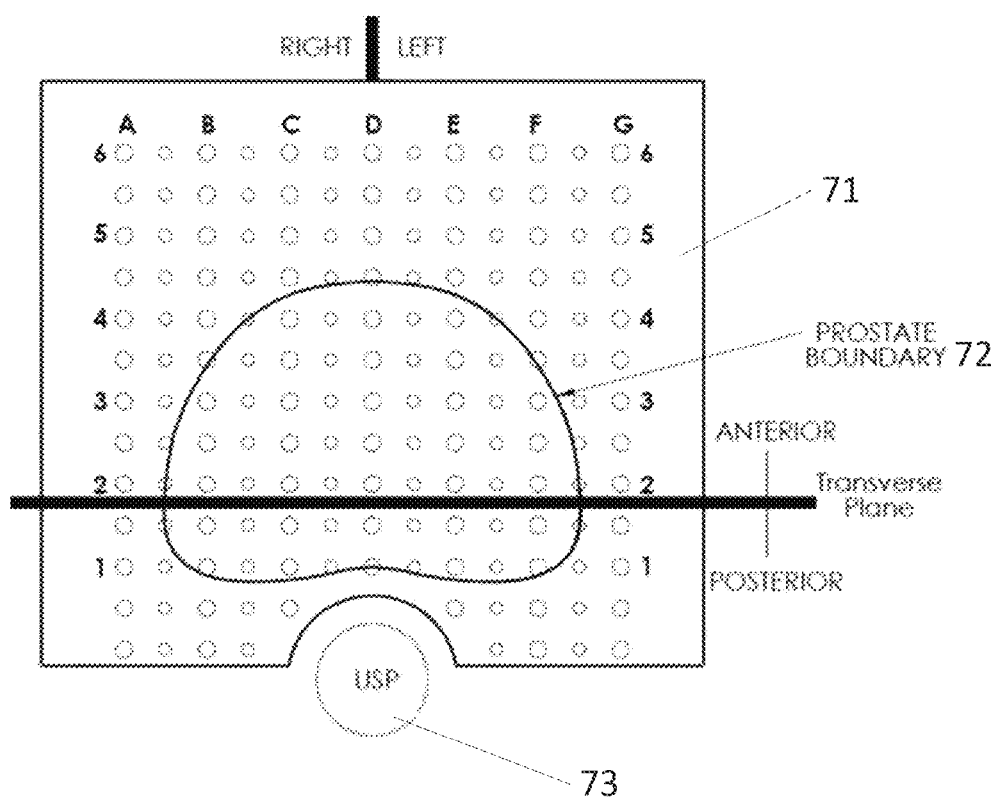
FIGS. 6 and 7 illustrate a coronal view of brachytherapy template and a prostate gland, and a sagittal view of the template, optical probe array including optical sensors, prostate gland, and USP according to embodiments.
Figure 7:
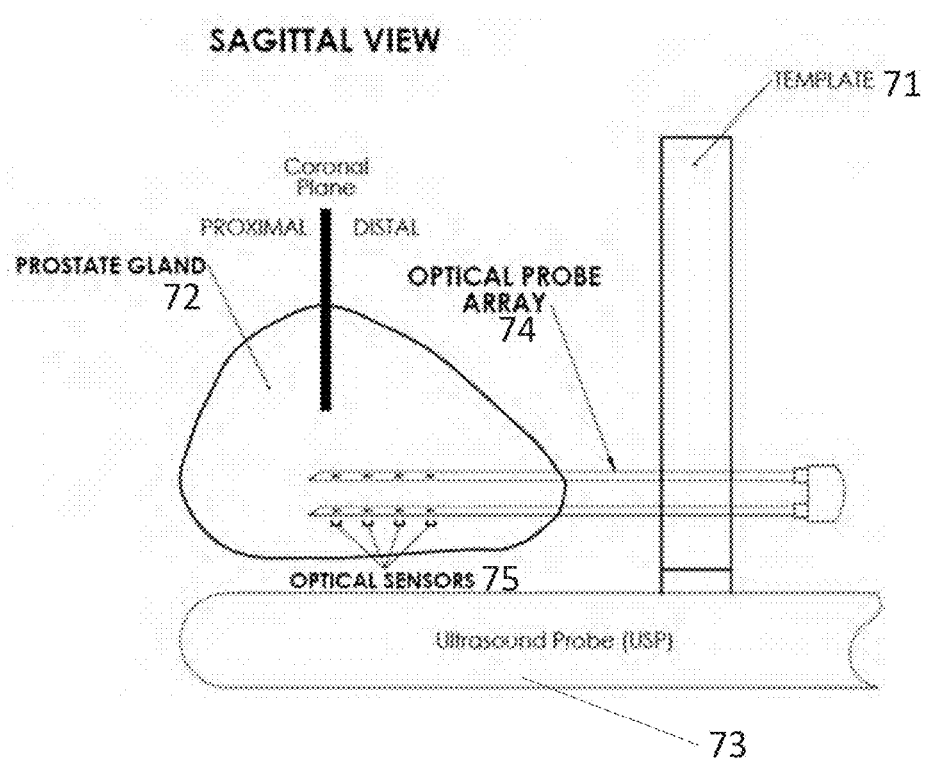

FIGS. 6-10 illustrate one embodiment of a system for use with a patient in the lithotomy position. FIG. 6 illustrates a coronal view of a brachytherapy template 71, a prostate gland 72, and an ultrasound probe (USP) 73. FIG. 7 illustrates a sagittal view of the template 71, an optical probe array 74 including optical sensors 75, the prostate gland 72, and the ultrasound probe 73 according to embodiments. In one embodiment, the template 71 may have alternating columns of openings of different diameter to accommodate different size probes, although any size opening and any type of hole configuration may be part of the template 71.

Figure 8:
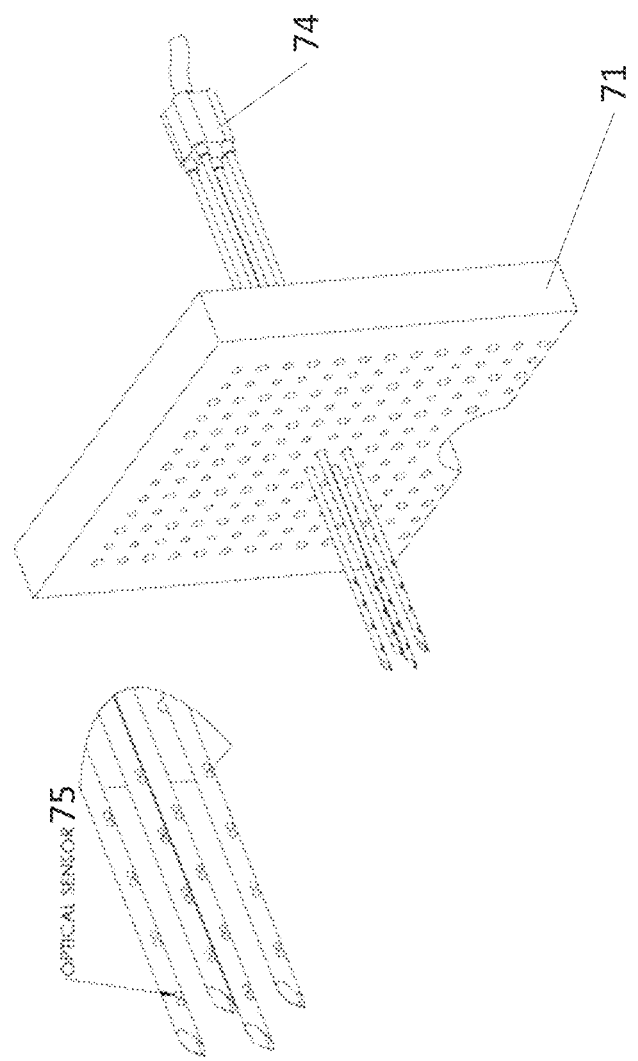
FIG. 8 illustrates a 2×2 fiber optic probe array with optical sensors on the left side and the 2×2 fiber optic probe array with optical sensors in combination with a brachytherapy template or similar on the right according to one embodiment.

FIG. 8 illustrates tips of a 2×2 fiber optic probe array 74 with optical sensors 75 shown in a partial exploded view and the 2×2 fiber optic probe array 74 with optical sensors 75 in combination with a perineal 13×13 grid template 74 according to one embodiment.

Figure 9:
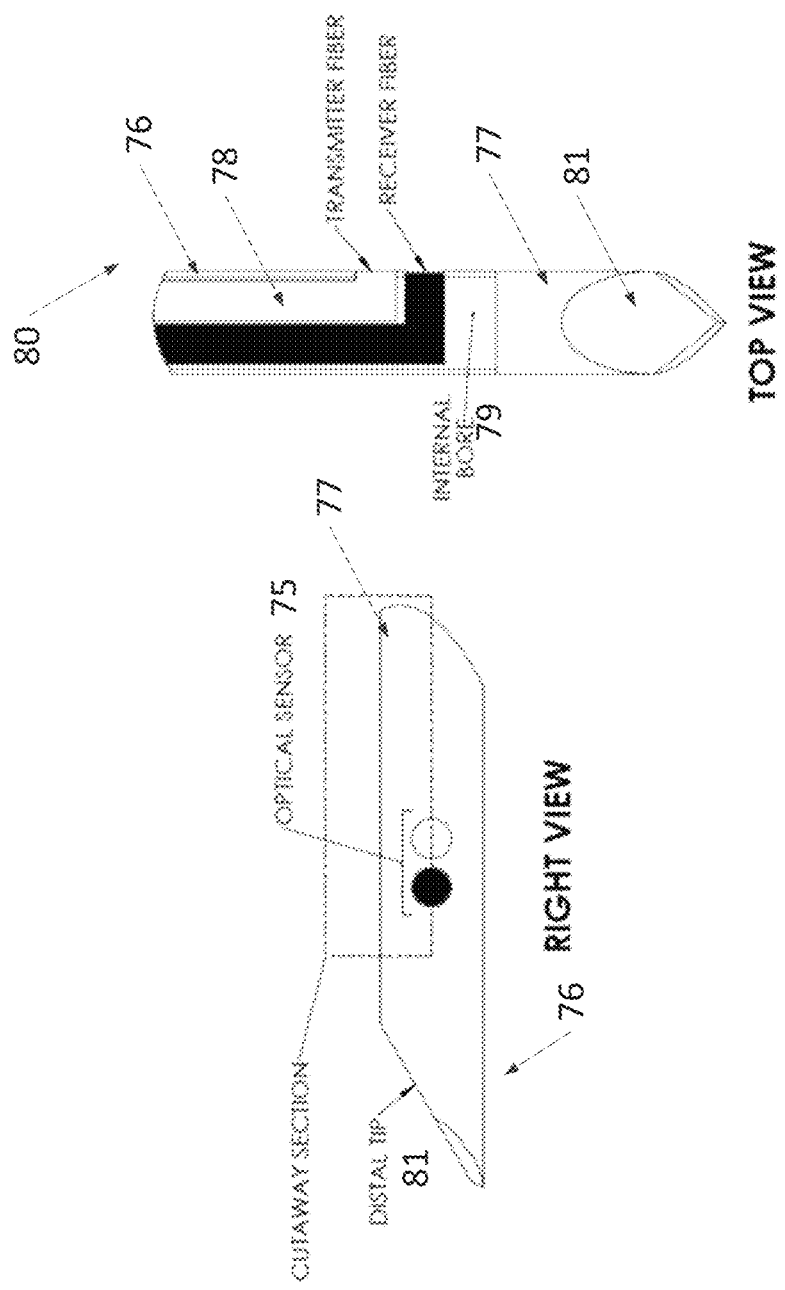
FIG. 9 illustrates a right side view and a top view with a portion cut away of a tip of a fiber optic probe according to one embodiment.

FIG. 9 illustrates a right side view and a top view with a portion cut away of a tip of a fiber optic probe 76 according to one embodiment. In one embodiment, the probe 76 comprises a hollow tube or shaft 77, a light source comprising a transmitting fiber optic 78 positioned within a bore 79 of the hollow tube 77 and supported by the shaft 77 to illuminate the tissue located near or at an end of the hollow tube or at angle with respect to the axis of the hollow tube, and a receiving optical fiber 80 positioned within the hollow tube to detect light from the illuminated tissue. In one form, the fiber 80 transmits the detected light to an optical light sensor which is part of an optical system (e.g., see FIG. 10 and optical system 115, below). Alternatively or in addition, light sensors may be positioned on the shaft 77. In one form, a distal tip 81 is tapered to facilitate insertion into the prostate gland. In one form, the transmitter and receiver fibers can be the same fiber. An optical splitter to separate the transmitted and received light can be located in the probe (disposable), within the cable (disposable), or within the system (as a capital or longer-lasting component).

Figure 10:
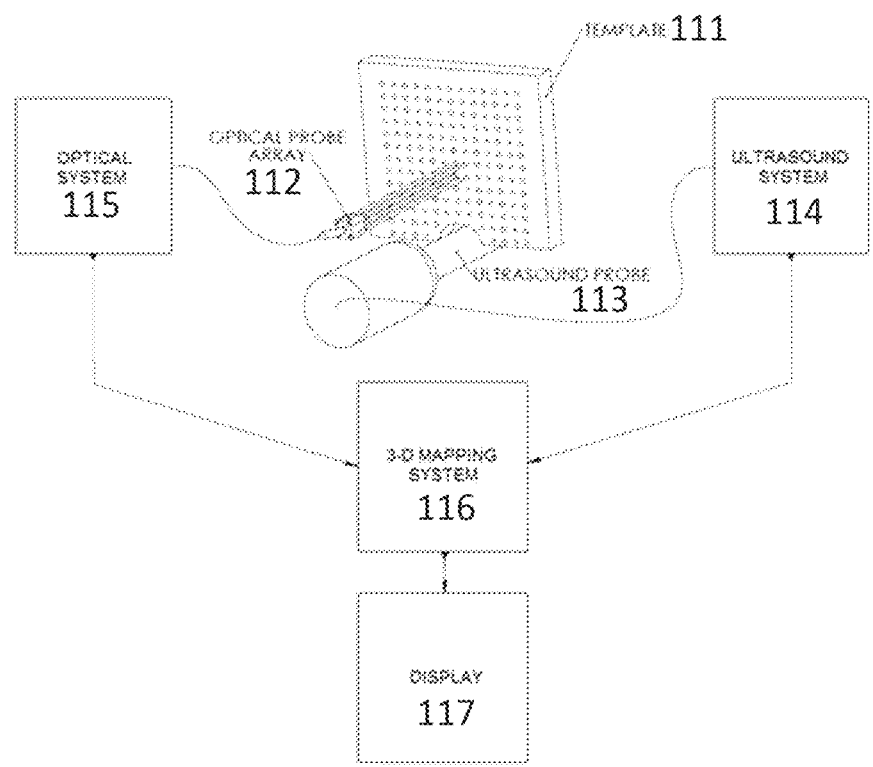
FIG. 10 illustrates a block diagram of an imaging system to diagnose and identify cancer lesions of the prostate according to one embodiment.

FIG. 10 illustrates a block diagram of a system for 3D imaging of the prostate according to one embodiment. The patient is positioned in the lithotomy position and a spatial template 111 or grid is placed against the perineum for aligning optical probes of an array 112 into a predetermined orientation relative to each other and relative to the tissue. The optical probe array 112 is guided into the prostate under imaging guidance (e.g. transrectal ultrasound probe 113 connected to an imaging guidance system 114) so that the optical sensors are within the prostate gland. Thus, the imaging guidance system 114 identifies the position of the optical probes of the array 112 relative to the prostate tissue. An optical system 115 which comprises at least one light source and at least one light detector (e.g. spectrometer) transmits to and receives light from the optical probe array 112. Light received by the optical system 115 is collected by the light sensor or detector, then digitized and processed (e.g., through a diagnostic algorithm) giving an indication of tissue condition (e.g. the presence or absence of disease). Diagnostic information from the optical system 114 is then combined with spatial information from the ultrasound probe 113 (e.g. probe and probe sensor positions within the prostate are stored). Once an acquisition has been performed, the probe array 112 can be moved to a new site within the prostate to perform additional acquisitions. With acquisitions covering sufficient volume of the prostate, a three-dimensional diagnostic imaging system 116 forms a 3D map of the imaged prostate gland based on the generated light signals and the identified position of the optical probe 112. The imaging system 116 and/or a 3D map displayed as an image on display 117 can be used to guide targeted therapeutic modalities to positions where lesions have been identified.

Among other things, the system includes an ultrasound transducer and sensor (e.g., probe 113) with ultrasound control system 114, an optical probe array 112 connected to an optical control system 115, a template 111 or other spatial control device (e.g. a grid), a 3-D imaging system 116 (e.g. a processor, memory user software, and graphical display) and an optional therapeutic modality system (e.g., a processor, not shown) for analyzing the test results. A fluorometer (not shown), spectrometer (not shown) or other optical phenomena detecting device with user interface software and tissue classification algorithm may be part of the optical system 115.

In one embodiment, the optical system 115 includes light sources such as LEDs, broadband tungsten-halogen or xenon lamps or lasers that transmit light to the tissue under examination through at least one optical fiber. Light reflected or emitted from the tissue under examination is routed via optical fiber or fibers to at least one optical detector or sensor of the optical system 115. The light sources and detectors are controlled by the optical system 115 which comprises a processor, memory, and communication components similar to a computer. The optical probes of the array 112 are positioned adjacent to or inserted into inside the prostate (or other tissue) through a transperineal grid template or other methods in order to create a 3-D image of the prostate based on tissue fluorescence and/or based on any other type of light spectroscopy measurements based on scattering phenomena of the tissue to reflect, shift (Raman scattering), absorb or scatter light or other energy (e.g., ultraviolet). In general, it has been found that the tissue is somewhat translucent and that when the tissue is illuminated with light energy, the energy tends to penetrate about 0.3 mm to 3.0 cm, depending on the wavelength and intensity. In addition, depending on wavelength and tissue composition, some tissue tends to fluoresce or otherwise provide excitations of varying wavelengths or other optical phenomena. Other energy may result in different penetration and response, depending on the type of tissue, its location and composition.

Using the spectroscopy measurements, tissue abnormalities are identified and mapped. For example, using fluorescence spectroscopy, NADH, tryptophan, and collagen components of the tissue will be identified as correlated to tissue abnormalities and mapped. Similarly, diffuse reflectance, scattering or absorptive light also provide irregularities and discontinuities in cell nuclei, cellular boundaries, etc., and presence/absence of various proteins as correlated to tissue abnormalities. This information can be translated for tissue classification for the purpose of identifying benign, malignant, calcified, and other components are labeled within the 3D optical mapping image.

Figure 11:
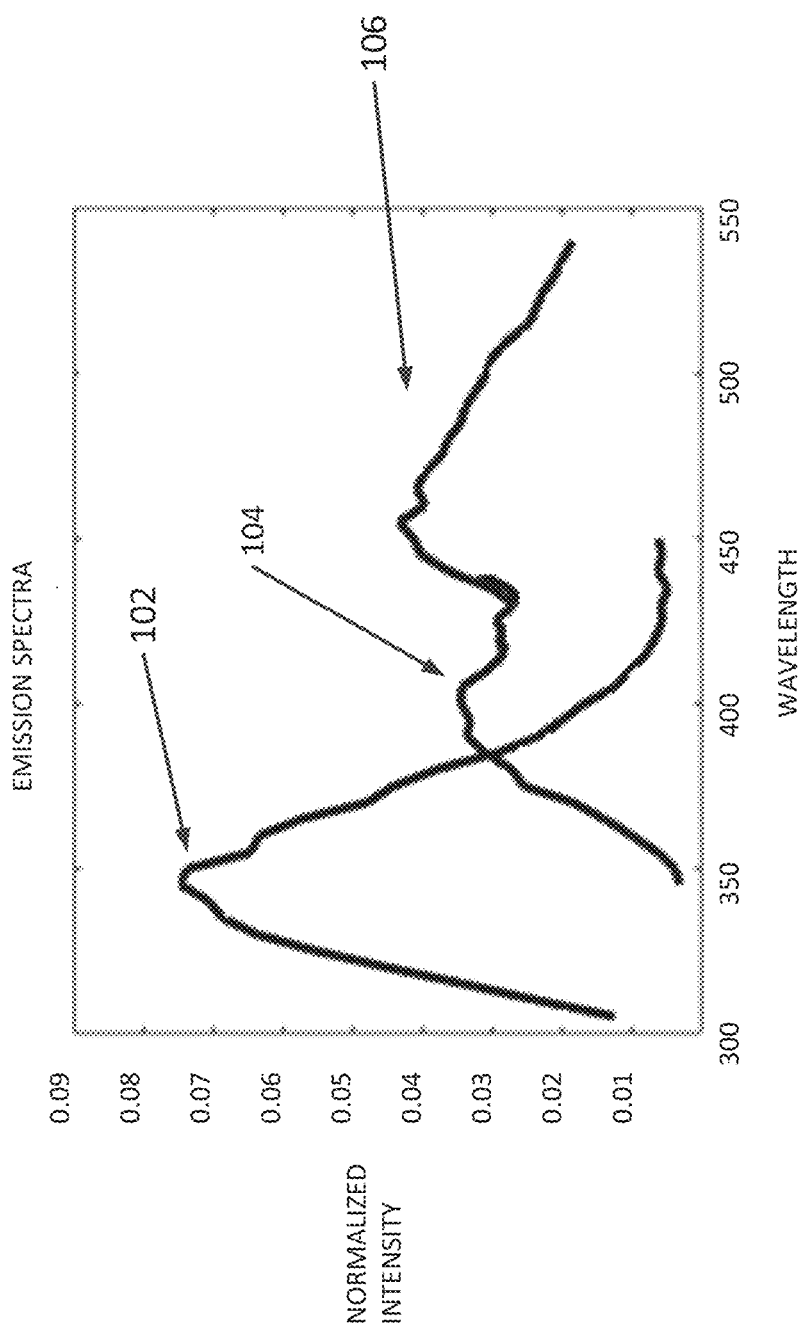
FIG. 11 illustrates the typical fluorescence spectra of prostate tissues for 290 and 340 nm excitation where peaks 102, 104 and 106 correspond to tryptophan, collagen, and NADH 104. X-axis represents emission spectra measured between 300 nm and 550 nm and Y-axis represents normalized intensity measured between 0.01 and 0.09.

There are a number of endogenous fluorophores available in human tissue (See Table 1, below). FIG. 11 illustrates the typical fluorescence spectra of prostate tissues for 290 and 340 nm excitation where peaks 102, 104 and 106 correspond to tryptophan, collagen, and NADH 104. X-axis represents emission spectra measured between 300 nm and 550 nm and Y-axis represents normalized intensity measured between 0.01 and 0.09. Collagen spectra can be obtained by excitation of tissue with a light source at 320-340 nm. NADH spectra can be obtained by excitation of tissue with a light source at 350-370 nm. As illustrated in FIG. 11, tryptophan spectra 102, collagen spectra 104, and NAHD spectra 106 register peak values at approximately 350 nm, 400 nm, and 460 nm, respectively.

Figure 12:
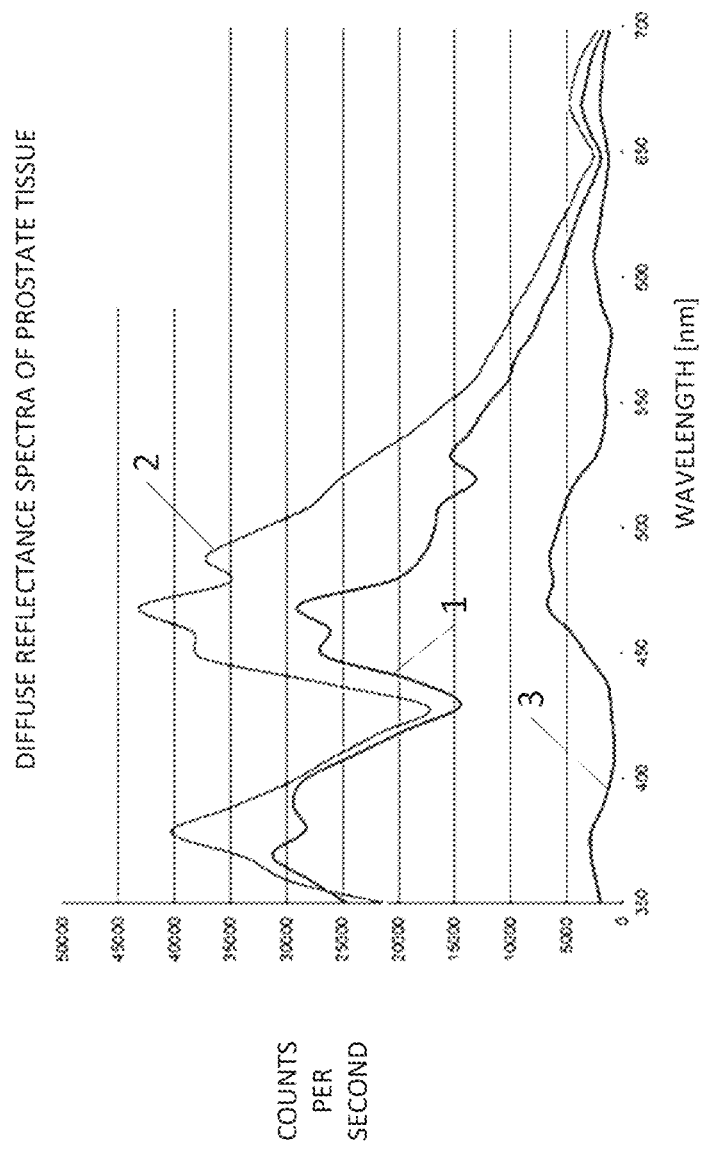
FIG. 12 illustrates typical diffuse reflectance spectra of prostate tissue. Each scan represents diffuse reflectance spectra obtained from different locations.

FIG. 12 illustrates typical diffuse reflectance spectra of prostate tissue for three different scans 1-3 taken by an optical probe array at three different locations within the prostate gland. Each scan represents diffuse reflectance spectra obtained from different locations. Diffuse reflectance spectra (DRS) provide architectural information about the tissue rather than chemical composition. Light photons scatter, bounce, and even get absorbed by the tissue. Diffuse reflectance spectroscopy, sometimes known as Elastic Scattering Spectroscopy, is a technique that measures the characteristic reflectance spectrum produced as light passed through a medium. The primary mechanisms are absorption and scattering, both of which vary with wavelength to produce the reflectance spectrum that is recorded. This spectrum contains information about the optical properties and structure of the medium being measured.

FIG. 12 illustrates typical DRS spectra of prostate tissue captured between 350 nm-700 nm inclusive of visible (VIS) range along the x-axis and intensity counts per second along the y-axis as a result of illuminating the tissue with a broadband light source having a wavelength range of at least 350 nm to 700 nm. Counts on y-axis are the measure of intensity at each wavelength. The spectrum is measured between 350-700 nm range at 5 nm intervals. The range along the x-axis (independent variable) is chosen and the intensity on y-axis (dependent variable) is measured.

There are two absorption features approximately 425 nm and 650 nm and variation in the slope between 475 nm-650 nm. If a broader band light source is used to illuminate the tissue (e.g., 350 nm to 1200 nm), additional features may be available from 700 nm-1200 nm (not shown) inclusive of near infrared (NIR) as well. These features may be utilized for prostate tissue classification. DRS primarily probes morphological features and has proven to be sensitive to histological grades. Gleason grade, which characterizes aggressiveness of PCa lesions based on glandular architecture, is a valuable prognostic variable. Patients with PCa of Gleason grade 4 or 5 are known to have poor clinical prognosis. Since light is scattered at cells or intracellular structures, DRS data contains structural information of the medium. Hence, the structural information in DRS can be used to differentiate low grade (Gleason score=6) from high grade (Gleason score≥7) carcinoma as well as classify benign versus malignant tissue.

In one embodiment, a fluorometer has a connector where it can communicate with an ultrasound system used within prostate cancer diagnostics and therapeutic procedures. User interface software is used to capture 3D transrectal ultrasound (TRUS) images of the prostate. Grid coordinates of brachytherapy template will be superimposed on 3D TRUS image of the prostate. Software enables users to highlight each XY coordinate position as well as Z coordinate (depth of the prostate) when cancer is identified. An optical probe is inserted into each grid coordinate point and fluorescence spectra are captured using the fluorometer.

Figure 13:
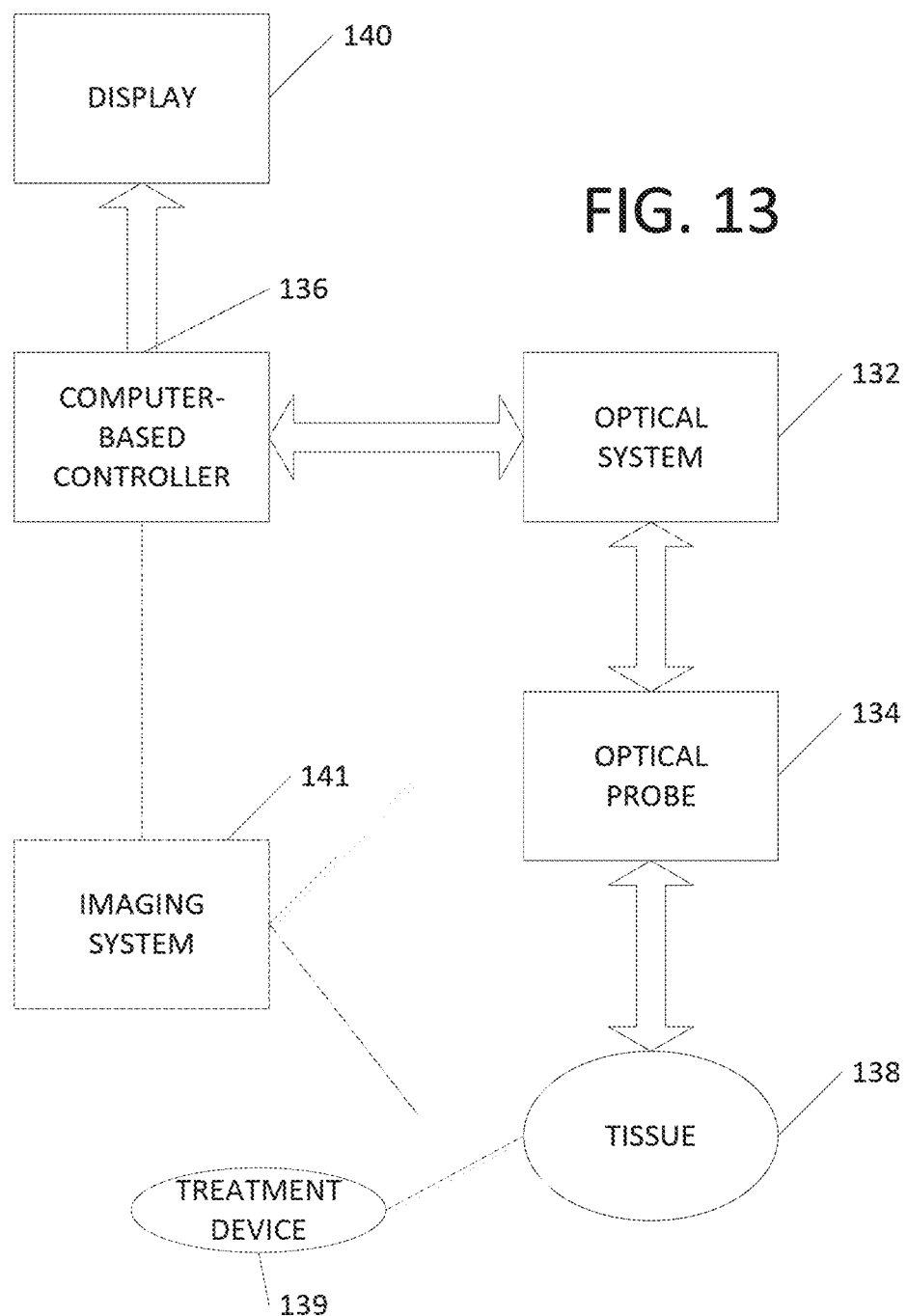
FIG. 13 illustrates in block diagram form one embodiment of an optical system connected to an optical probe and a computer controller executing user interface software and a tissue classification algorithm.

FIG. 13 illustrates in block diagram form one embodiment of an optical system 132 such as a fluorometer connected to an optical probe 134 and connected to a computer-based controller 136 executing user interface software and a tissue classification algorithm. The fluorometer 132 transmits light from a light source or sources through the probe 134 where light interacts with the tissue 138 and is received and transmitted back to a detector inside the fluorometer 132. The fluorometer 132 is operated by the computer-based controller 136 which processes received signals and delivers via display 140 diagnostic classification of the tissue under examination to the user. Thus, the display 140 presents a graphical user interface which, in its simplest form, is a two or three-dimensional image of the tissue. Alternatively, the interface may provide the user with options so that the user can select various images or perspectives of an image. For example, the interface can give the user the option to select a two-dimensional image, a three-dimensional image, a fused image, or some other image variation. The interface can also provide the user with the option to select a black-and-white image, a color image, a line image or other image parameter variations. Optionally, the system of FIG. 13 can be used in combination with an imaging system 141 such as an ultrasound system or a MRI/CT system or both for identifying the position of the optical probes relative to the tissue. (See also FIG. 23). A treatment device 139 employing a treatment modality such as described herein can be used in combination with the imaged or mapped tissue to treat the imaged tissue. For example, the device 139 can be a Cryotherapy device; a Photodynamic Therapy device; a Brachytherapy device; a high-intensity focused ultrasound (HIFU) device; a tissue ablation device; a Laser ablation device; a RF ablation device; a Vapor ablation device; and a Local drug delivery device.

In one embodiment, when the tissue classification algorithm indicates that the location is positive for cancer based on fluorophores tryptophan, collagen, and NADH, an operator estimates the location (e.g., the depth of insertion on live TRUS image of the prostate) and highlights corresponding XYZ coordinates in the 3D TRUS image on the fluorometer. The above process continues until all grid coordinates overlapping the prostate are complete. Each optical sensor measurement will be correlated to an ultrasound coordinate so that the optical sensor measurements and the ultrasound image can be overlapped to create the 3D optical image of the prostate. This is shown in the FIG. 5A which illustrates a 3D optically mapped image of the prostate following optical measurements identifying locations of prostate cancer lesions according to one embodiment. FIG. 5A shows a 3D cross section of XYZ coordinates and FIG. 5A shows tumor volume estimates based on optical sensor readings. At the completion of optical measurements and tissue classification using the algorithm, a 3D image of the prostate based on the optical measurements is generated. Optionally, image analysis software can be used to analyze the image of FIG. 5A to generate a corresponding line drawings as shown in FIG. 5B.

Endogenous fluorophores in biological tissues include FAD, NADH, collagen, elastin, tryptophan, tyrosine, phenylalanine, some vitamins, and lipids (which are main components of the cell membrane and some organelles). Excitation light at 290 and 340 nm is currently being used to classify prostate cancer tissue limiting us to items which excite near those wavelengths (see Table 1, below). However, additional excitation light sources may be added to excite other types of fluorophores to diagnose various other types of cancer based on further research. See table 1 below for an exemplary listing of endogenous fluorophores which may make up the components of tissue to be evaluation and their excitation maxima and emission maxima.

TABLE 1

| Endogenous fluorophores | Excitation minima (nm) | Emission maxima (nm) |
|---|---|---|
| Amino Acids | | |
| Tryptophan | 280 | 350 |
| Tyrosine | 275 | 300 |
| Phenylalanine | 260 | 280 |
| Structural proteins | | |
| Collagen | 325 | 400, 405 |
| Elastin | 290, 325 | 340, 400 |
| Enzymes and coenzymes | | |
| FAD, flavins | 450 | 535 |
| NADH | 290, 351 | 440, 460 |
| NADPH | 336 | 464 |
| Vitamins | | |
| Vitamin A | 327 | 510 |
| Vitamin K | 335 | 480 |
| Vitamin D | 390 | 480 |
| Vitamin $B_6$ compounds | | |
| Pyridoxine | 332, 340 | 400 |
| Pyridoxamone | 335 | 400 |
| Pyridoxal | 330 | 385 |
| Pyridoxic acid | 315 | 425 |
| Pyridoxal 5'-phosphate | 330 | 400 |
| Vitamin $B_{12}$ | 275 | 305 |
| Lipids | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

Data processing and a typical tissue classification algorithm are based on a support vector machine (SVM) or other statistical methods and systems suitable for classification such as linear discriminant analysis (LDA), artificial neural networks (ANN), multiple logistic regression, etc. Here we describe the procedure for SVM-based tissue classification, although it can be extended to other methods and systems as well. In machine learning, support vector machines (SVMs) are supervised learning models with associated learning algorithms that analyze data and recognize patterns, used for classification and regression analysis. The basic SVM takes a set of input data and predicts, for each given input, which of two possible classes forms the output, making it a non-probabilistic binary linear classifier. Given a set of training examples, each marked as belonging to one of two categories, an SVM training algorithm builds a model that assigns new examples into one category or the other. An SVM model is a representation of the examples as points in space, mapped so that the examples of the separate categories are divided by a clear gap that is as wide as possible. New examples are then mapped into that same space and predicted to belong to a category based on which side of the gap they fall on. In addition to performing linear classification, SVMs can efficiently perform non-linear classification using what is called the kernel trick, implicitly imaging their inputs into high-dimensional feature spaces.

Below is one example of a software data process of computer executable instructions stored on a tangible, non-transitory storage medium and executed by a processor to validate data based on a support vector machine (SVM):

Raw Data such as fluorescence spectra and histopathology of the tissue score is captured;

Conditioning of the raw data includes background subtraction and S/N ratio cutoff;

Preprocessing of the conditioned data involved data smoothing, interpolation and normalization;

Prostate Cancer evaluation includes partial least square (PLS) analysis of the preprocessed data;

Prostate Cancer selection involves statistical analysis of the evaluated data including reducing false positives (FP) and reducing false negatives (FN);

An algorithm executed on the selected data by a support vector machine (SVM) analyzes the selected data to provide a binary classification (cancer/no cancer) of the tissue under evaluation.

Validation of the analyzed data includes statistical analysis by such techniques as "leave one out" cross-validation and/or external analysis.

Figure 14:
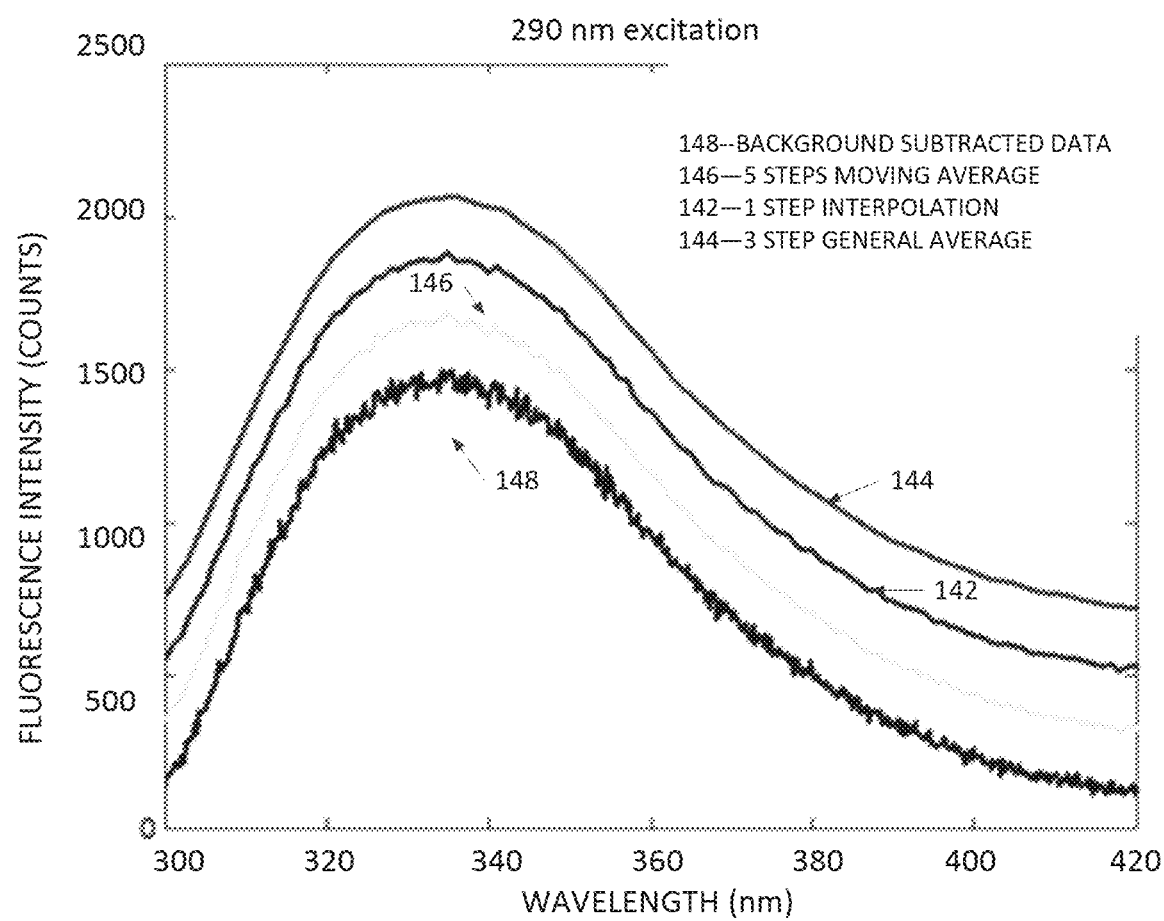
FIGS. 14-15 illustrate fluorescence intensity spectra of prostate tissue at 290 and 340 nm excitation being processed for analysis and classification, with fluorescence intensity (counts) along the y-axis and wavelength (nm) along the x-axis.
Figure 15:
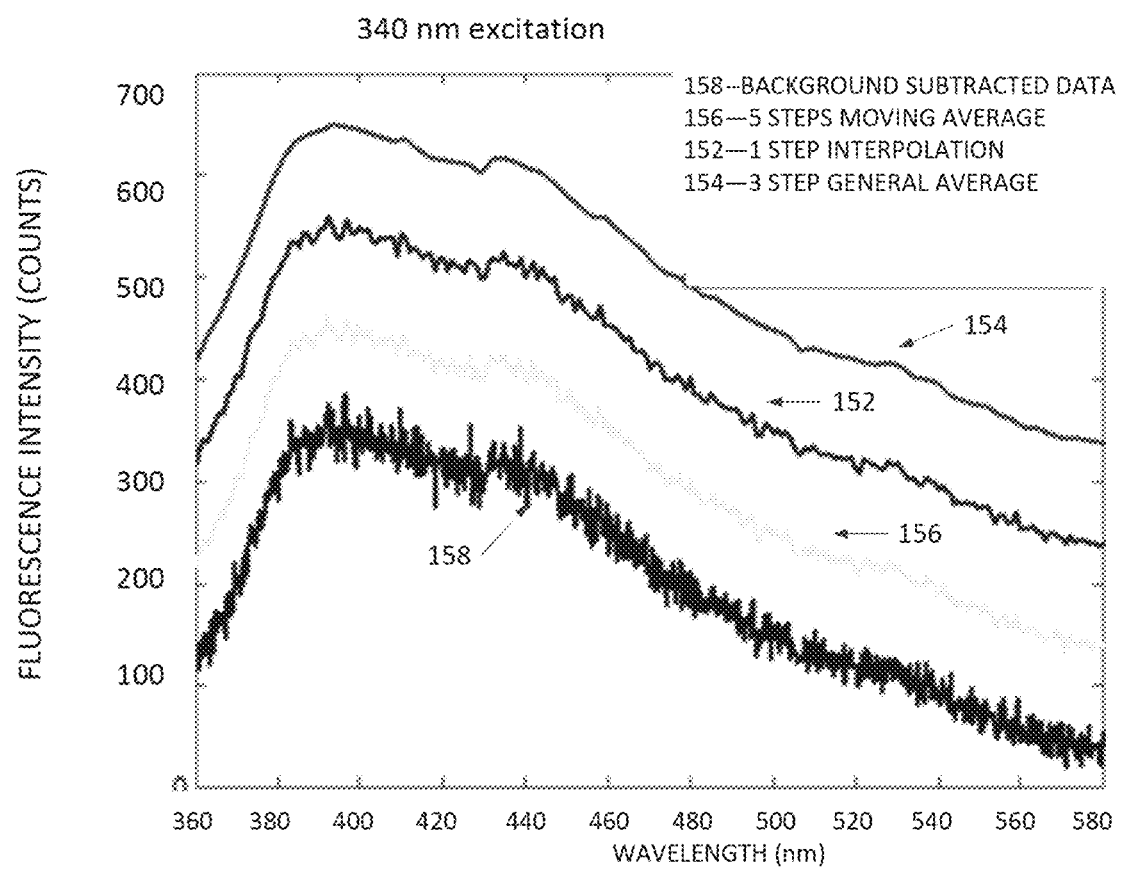
Figure 16:
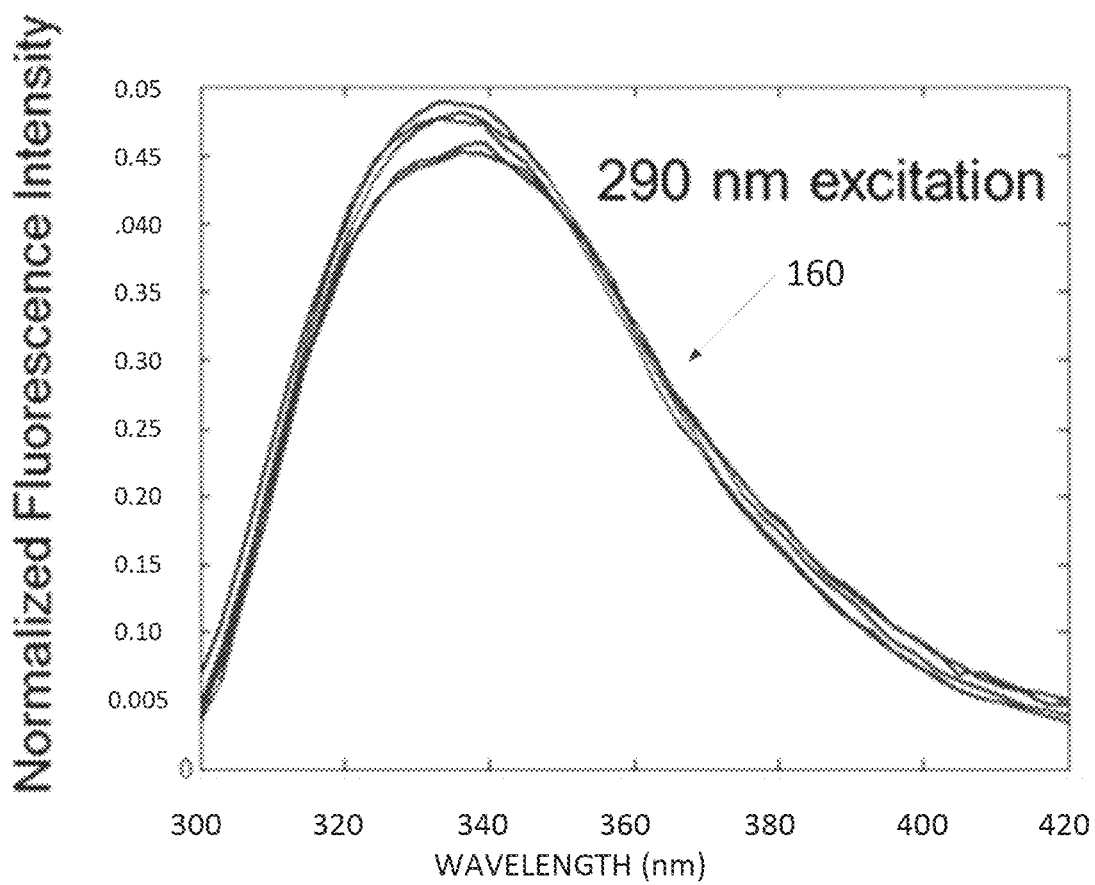
FIGS. 16-17 illustrate normalized fluorescence intensity spectra of prostate tissue at 290 and 340 nm excitation being processed for analysis and classification, with normalized fluorescence intensity along the y-axis and wavelength in nanometers (nm) along the x-axis.
Figure 17:
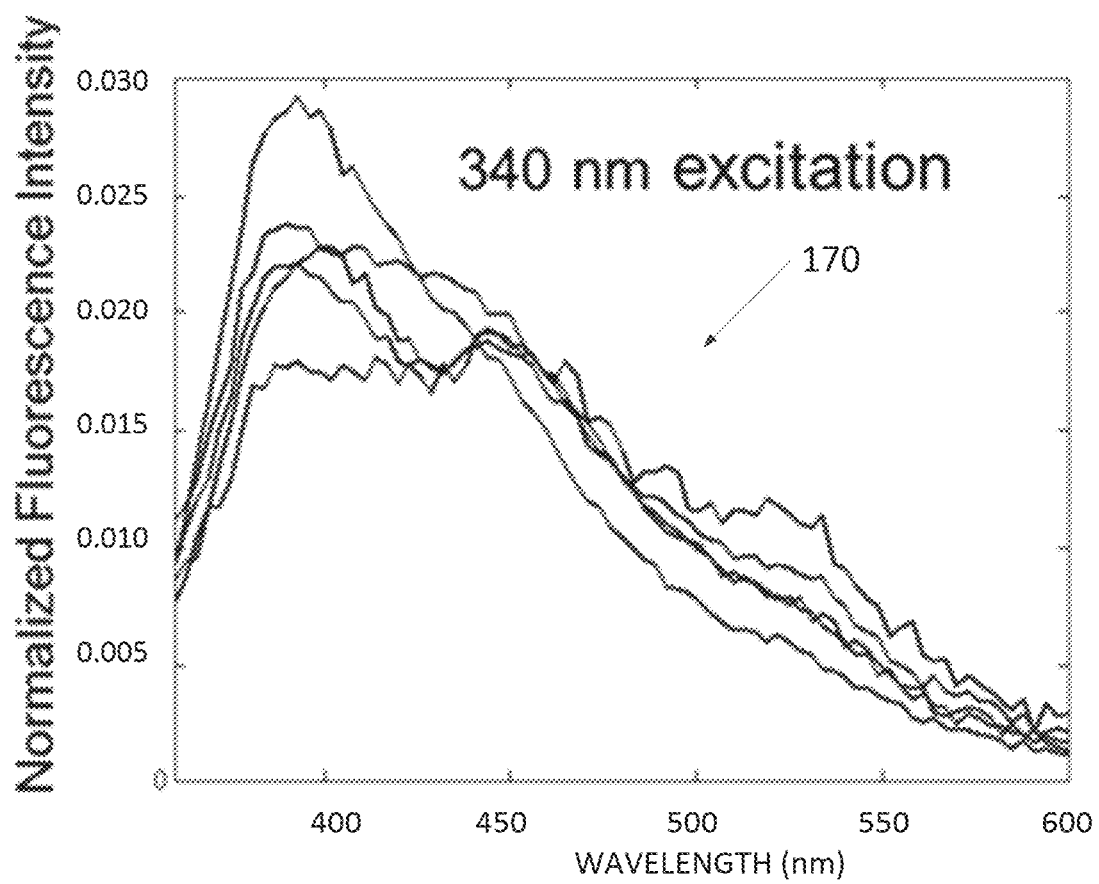
Figure 18:
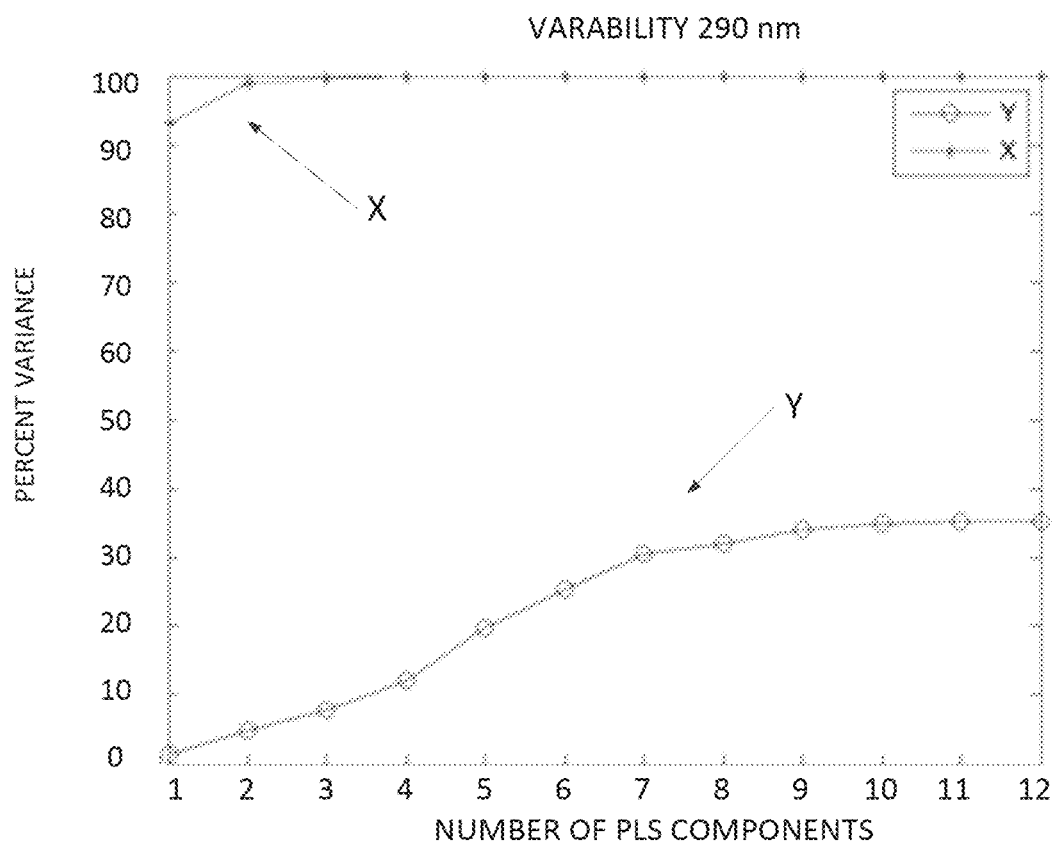
FIGS. 18-19 illustrate percentage variability in fluorescence spectra labeled X and histopathology data labeled Y associated with partial least square (PLS) components at 290 nm and 340 nm variability, with percent variance along the y-axis and number of partial least square (PLS) components along the x-axis.
Figure 19:
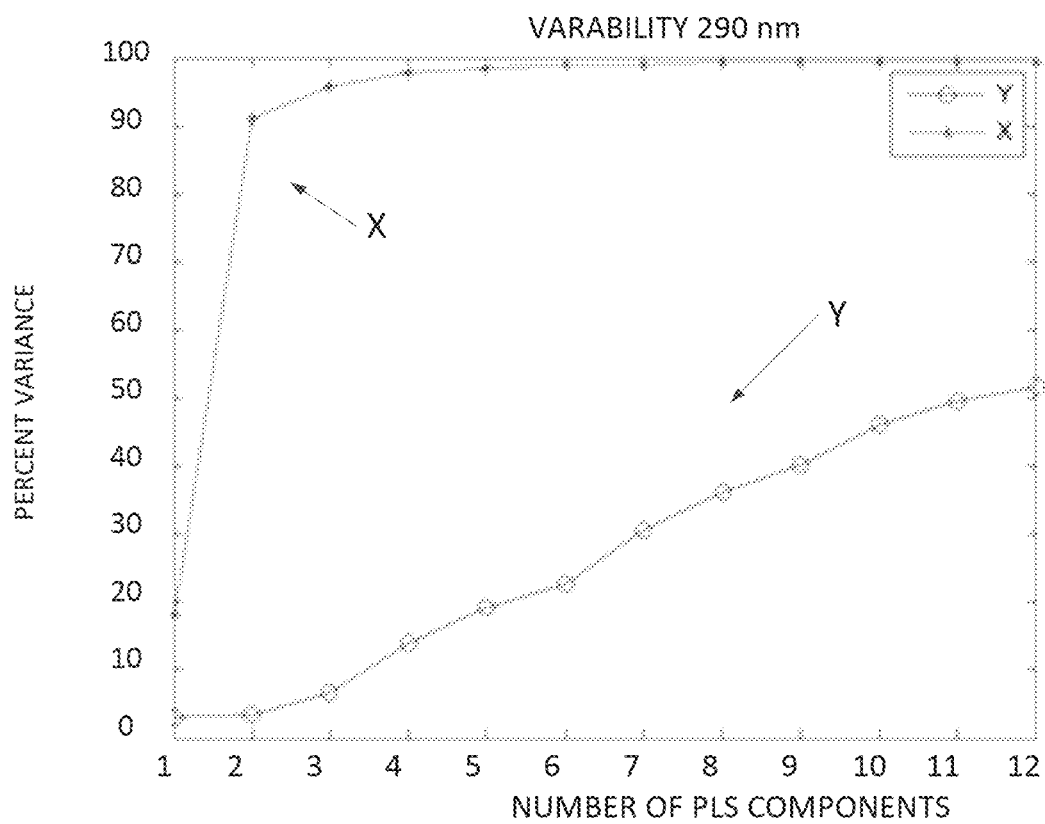

FIG. 14 illustrates fluorescence intensity spectra at 290 nm being processed for analysis and classification by 1-step interpolation 142, 3-step general average 144, 5-step moving average 146, and background data 148 which is subtracted. FIG. 15 illustrates fluorescence intensity spectra at 340 nm being processed for analysis and classification by 1-step interpolation 152, 3-step general average 154, 5-step moving average 156, and background data 158 which is subtracted. FIG. 16 illustrates several normalized fluorescence intensity spectra 160 at 290 nm excitation being processed for analysis and classification. FIG. 17 illustrates several normalized fluorescence intensity spectra 170 at 340 nm excitation being processed for analysis and classification. FIGS. 18-19 illustrate percentage variability in fluorescence spectra X and histopathology data Y associated with 1 to 12 PLS components at 290 nm and 340 nm variability, respectively.

In one embodiment, not all components in fluorescence spectra will have the same "weights." The partial least squares (PLS) analysis identifies which portions of the emission spectra are likely to contain unique features to help with determining the classification. PLS analysis will create a linear combination of weighted values relative to the size of the spectral data values. As an example, if there are 1000 discrete intensity values from a single emission spectra, there will be a weight matrix of the same number of discrete values (in this example, 1000 in all). An algorithm can be configured to focus on the interested component, say 12 partial least squares components, which in this example would create a matrix of size 1000 by 12 where each column vector represents the linear combination of weighted values for the single PLS analysis. FIG. 18 illustrates percentage variability in fluorescence spectra and histopathology data associated with 1 to 12 PLS components. A ranking test such as a Wilcoxon Rank Sum test is then used to determine which weight vectors are least significantly correlated since some features may be redundant due to tracking the identical fluorophores. Since PLS components for fluorescence spectra at different excitations may be correlated, Pearson correlation coefficient is tested to identify such correlations. In the event two PLS components are correlated, only one is selected for tissue classification. PLS will inherently create disproportionate weighting of spectral data in attempts of highlighting important features and suppressing less important elements. A feasibility study was conducted during July-December, 2012 to determine the efficacy of an optical biopsy needle adjunct with fluorescence spectroscopy for diagnosis of prostate cancer. A total of 208 in vivo biopsies (29 malignant) and 224 ex vivo biopsies (51 malignant) were studied. The next two tables summarize the SVM results for sensitivity (SE), specificity (SP), positive predictive value (PPV), negative predictive value (NPV), true positives (TP), true negative (TN), false positives (FP), and false negatives (FN) based on selected PLS components.

The following Tables 2 and 3 illustrate results as noted above:

TABLE 2

SVM Classification of Benign versus Malignant Disease For In Vivo Data

|  | PLSC#1-5 | PLSC#1-7 | PLSC#1-10 |
| --- | --- | --- | --- |
| TP | 17 | 21 | 19 |
| TN | 118 | 133 | 133 |
| FP | 29 | 14 | 14 |
| FN | 8 | 4 | 6 |
| SP | 80% | 90% | 90% |
| SE | 68% | 84% | 76% |
| PPV | 37% | 60% | 58% |
| NPV | 94% | 97% | 96% |

TABLE 3

SVM Classification of Benign versus Malignant Disease For Ex Vivo Data

|  | PLSC#1-5 | PLSC#1-7 | PLSC#1-10 |
| --- | --- | --- | --- |
| TP | 28 | 26 | 25 |
| TN | 132 | 136 | 138 |
| FP | 11 | 7 | 5 |
| FN | 4 | 6 | 7 |
| SP | 92% | 95% | 97% |
| SE | 88% | 81% | 78% |
| PPV | 72% | 79% | 83% |
| NPV | 97% | 96% | 95% |

Figure 20:
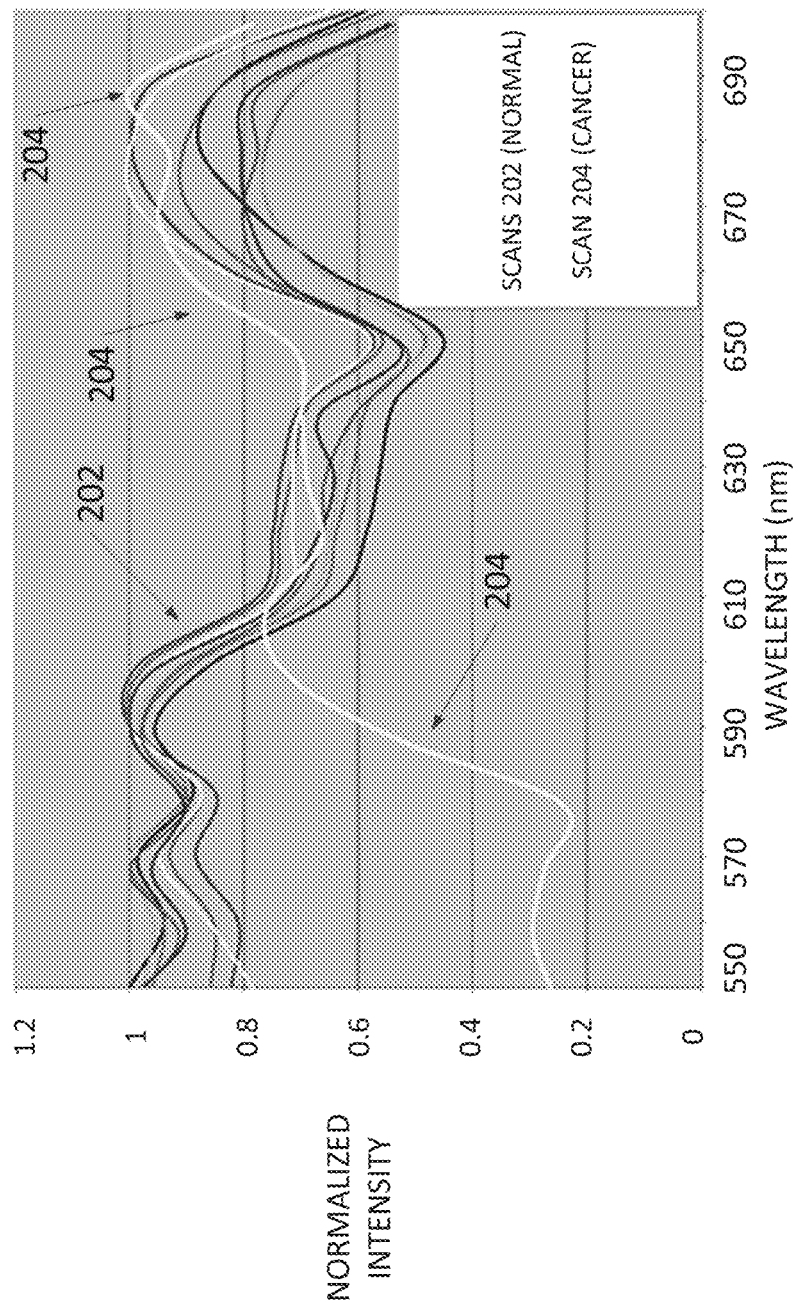
FIG. 20 shows typical normalized diffuse reflectance spectra scans of prostate tissue within the range of 550 nm-700 nm, with normalized intensity along the y-axis and wavelength (nm) along the x-axis.
Figure 21:
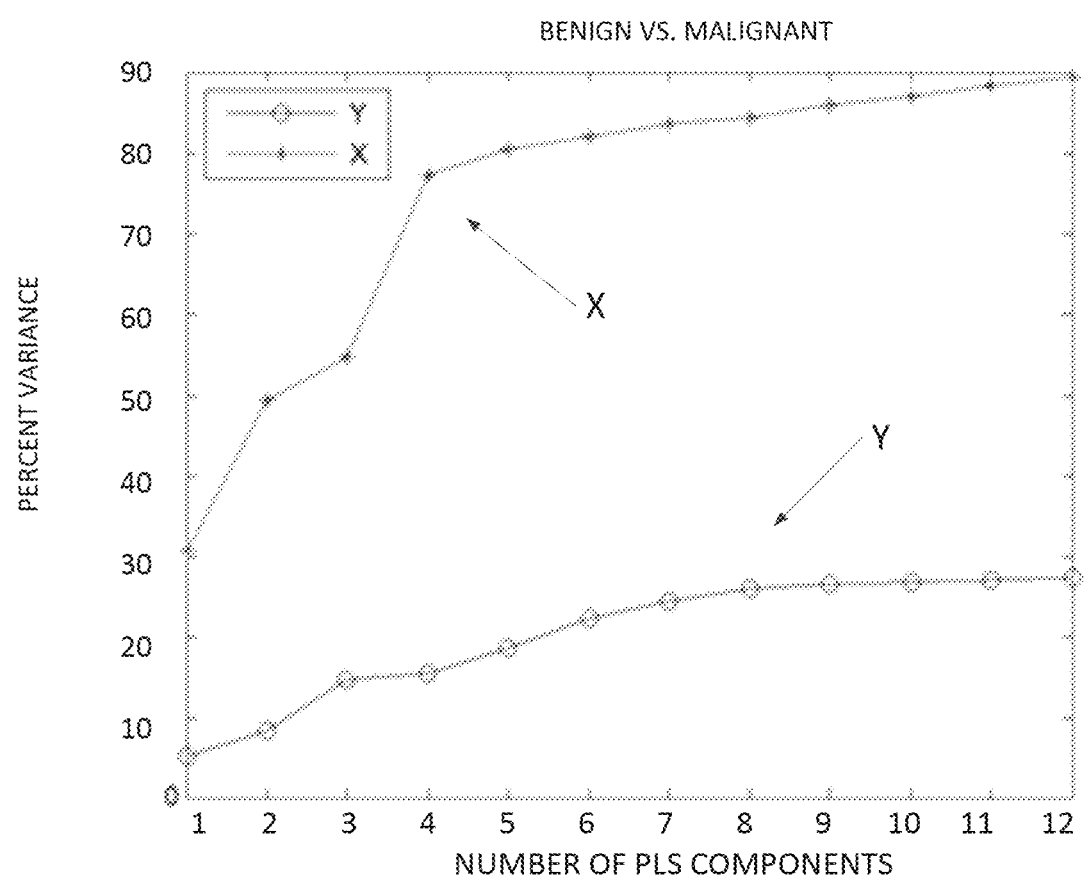
FIGS. 21-22 illustrate the percentage variability in diffuse reflectance spectra labeled X and histopathology data labeled Y associated with 1 to 12 PLS components for benign versus malignant and high grade versus low grade prostate tissue classification, respectively, with percent variance along the y-axis and number of PLS components along the x-axis.
Figure 22:
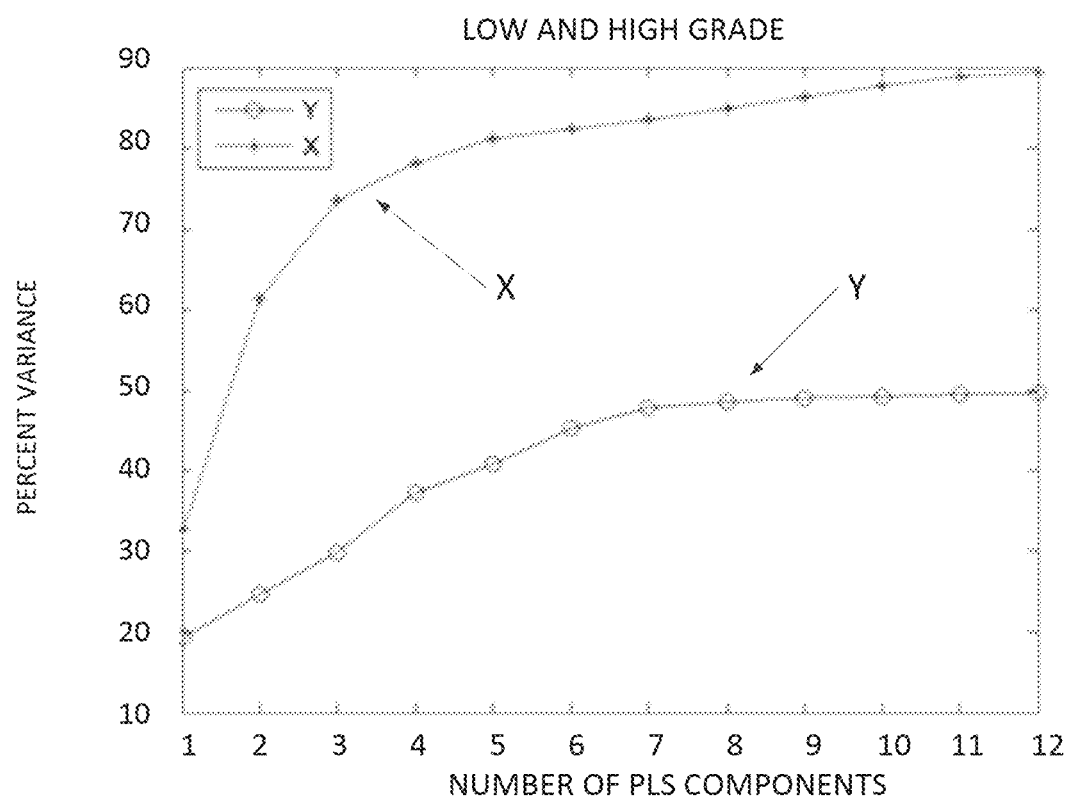

In one embodiment, diffuse reflectance spectra are processed as an adjunct to identify benign versus malignant disease as well as high (Gleason sum≥7) versus low (Gleason sum≤6) disease located up to 1 cm from the optical sensor. FIG. 20 shows typical normalized diffuse reflectance spectra scans for prostate tissue within the range of 550 nm-700 nm for eight (8) normal scans 202 and one cancer indicative scan 204. Histopathology of the biopsy core up to 1 cm length is taken into consideration for DRS. A total of 263 biopsy cores were analyzed Histopathological analysis classified 151 biopsy cores as benign and 112 as malignant. Out of 112 malignant cores, 61 were classified as low grade disease (Gleason score≤6) and remaining 51 were classified as high grade disease (Gleason score≥7). DRS data were processed according to steps outlined above based on a support vector machine (SVM). PLS components were computed and selected as previously described FIGS. 21-22 illustrate the percentage variability in DRS and histopathology data associated with 1 to 12 PLS components for benign versus malignant and high grade versus low grade prostate tissue classification, respectively. The percent variance is illustrated along the y-axis and the number of PLS components is illustrated along the x-axis. FIG. 21 illustrates percentage variability in spectral data X and histopathology Y associated with each PLS component. PLS attempts to minimize least square error while projecting X and Y data. By selecting a combination of PLS components, one can identify a minimum set of classifiers that best describe X and Y while keeping the percentage variability to acceptable levels. In this FIG. 21, PLS components #1-6 describes 80% out of 90% total variability of X and 25% out of 30% of total variability of Y. Therefore, PLS components #1-6 may be used in SVM for benign versus malignant tissue classification.

Similarly, FIG. 22 illustrates variability in spectral data X and histopathology Y associated with each PLS component. In this FIG. 22, PLS components #1-7 describes 85% out of 90% total variability of X and 48% out of 50% of total variability of Y. Therefore, PLS components #1-7 may be used in SVM for low versus high grade cancer tissue classification.

The following Table 4 summarizes typical values for sensitivity (SE), specificity (SP), positive predictive value (PPV), negative predictive value (NPV), true positives (TP), true negative (TN), false positives (FP), and false negatives (FN) obtained for this type of data set.

TABLE 4

Prostate Tissue Classification based on Diffuse Reflectance Spectra

| | Classification | | | | | | | |
|---|---|---|---|---|---|---|---|---|
| | TP | TN | FP | FN | SE | SP | PPV | NPV |
| Benign vs. Malignant | 73 | 105 | 57 | 39 | 65% | 70% | 61% | 73% |
| Benign vs. Low Grade | 44 | 106 | 45 | 17 | 72% | 70% | 49% | 86% |
| Benign vs. High Grade | 39 | 119 | 32 | 12 | 76% | 79% | 55% | 91% |
| High vs. Low Grade | 41 | 49 | 12 | 10 | 80% | 80% | 77% | 83% |

FIG. 23 illustrates in block diagram form one embodiment of an optical system 332 such as a fluorometer or a diffuse reflectance spectometer connected to an optical probe 334 and connected to a computer-based controller 336 executing user interface software and a tissue classification algorithm. The optical system 332 transmits light from a light source or sources through the probe 334 where light interacts with the tissue 338 and is received and transmitted back to a detector inside the optical system 332. The optical system 332 is operated by the computer-based controller 336 which processes received signals and delivers via display 340 diagnostic classification of the tissue under examination to the user. For example, the display 340 may be an image as illustrated in FIG. 11, 12 or 14-22. Thus, the display 340 presents a graphical user interface which, in its simplest form, is a two (or three) dimensional image indicate of the condition of the tissue as indicated by the light signal detected by the optical system 332. For example, the light signals are indicative of the light emitted, reflected and/or absorbed by the tissue. In addition, an imaging system 341 such as an ultrasound system or a MRI/CT system or both in combination has a display 343 which provides a fused US/MRI or US/CT image for identifying the position of the optical probe 334 relative to the tissue 338. Alternatively or in addition, the user interface on display 340 can provide the user with options so that the user can select various images or perspectives of an image. For example, the interface can give the user the option to select a two-dimensional image, a three-dimensional image, a fused image, or some other image variation. The interface can also provide the user with the option to select a black-and-white image, a color image, a line image or other image parameter variations.

Figure 24A:
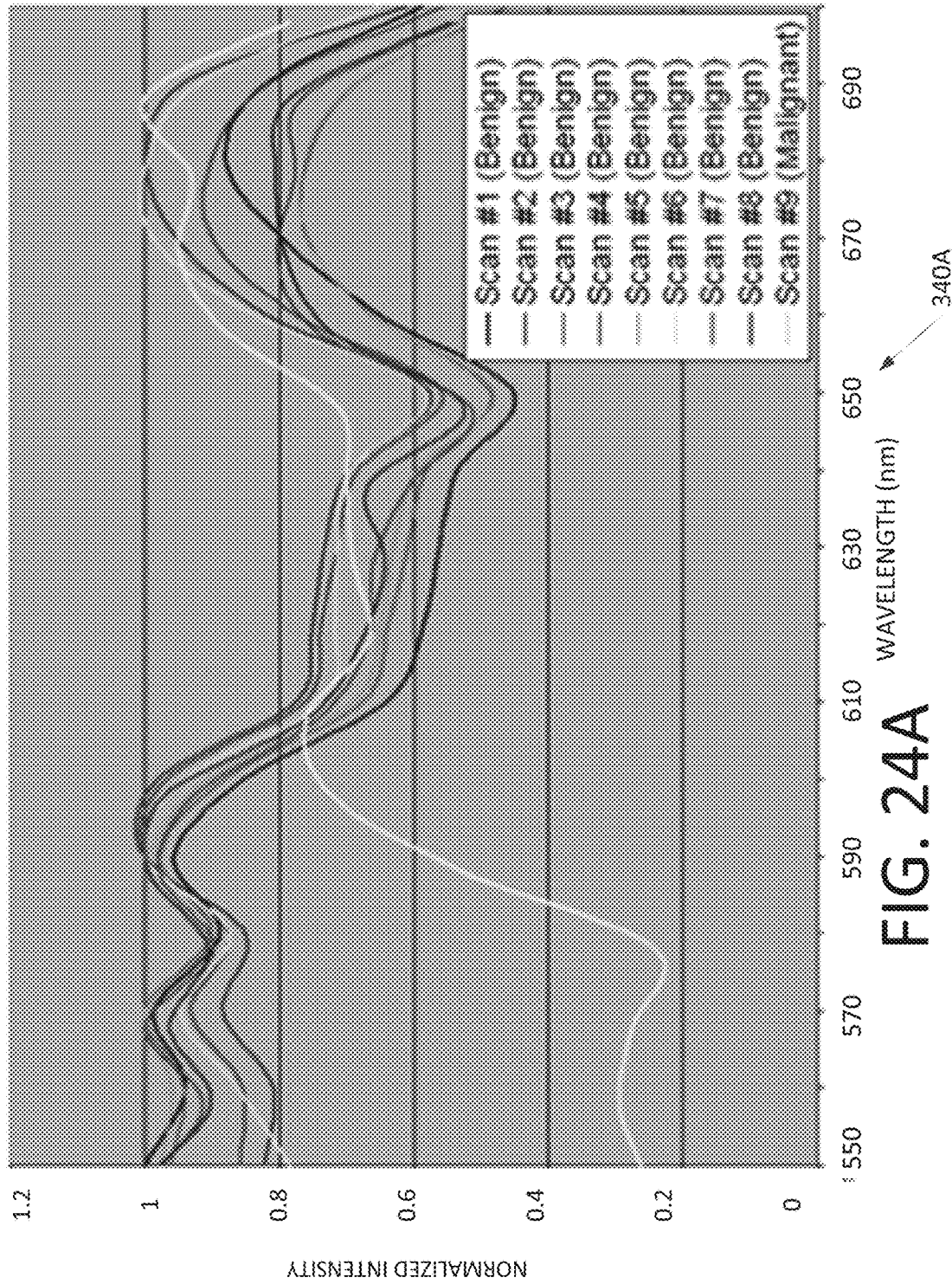
FIG. 24A illustrates one photograph 340A which illustrates elastic scattering spectra captured from the location or vicinity of the cancer lesion shown in MRI/US fusion image 343B. When this spectrum is processed by a tissue classification algorithm, it can either confirm or contradict the existence of cancer lesion shown in MRI/US fusion image for 3D optical mapping of the prostate.
Figure 24B:
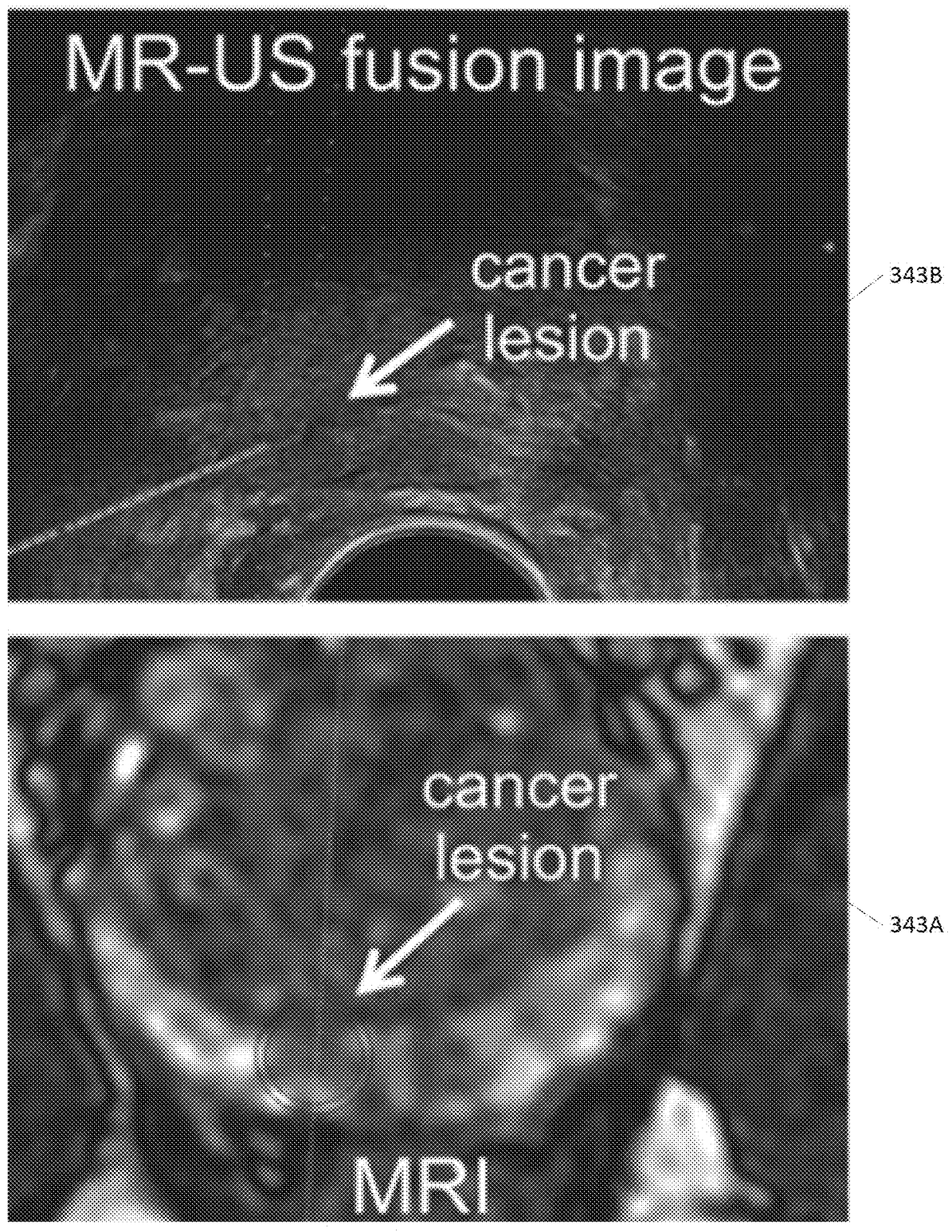
FIG. 24B illustrates two photographs, the lower photo 343A is an MRI image where a cancer lesion was first diagnosed by a radiologist and the upper photo 343B is a MRI fusion image showing a cancer lesion fused with an ultrasound (US) image.

It is also contemplated that any of the above noted images may be combined or fused with a MRI image or CT image of the same tissue to provide additional diagnostic and treatment information. For example, FIG. 24B illustrates two photographs, the lower photo 343A is an MRI image where a cancer lesion was first diagnosed by a radiologist and the upper photo 343B is a MRI fusion image showing a cancer lesion fused with an ultrasound (US) image. This combined MRI/US image can be used for transrectal or transperineal directed biopsy of the prostate. When an optical biopsy needle 334 is used, elastic scattering spectra (e.g., FIG. 12) can be generated in the computer monitor display 340 from the location or vicinity of the cancer lesion shown in MRI/US fusion image. FIG. 24A illustrates one photograph 340A which illustrates elastic scattering spectra. This elastic scattering spectra presented on display 340A when processed by a tissue classification algorithm, can either confirm or contradict the existence of a cancer lesion shown in MRI/US fusion image 343B.

Figure 25A:
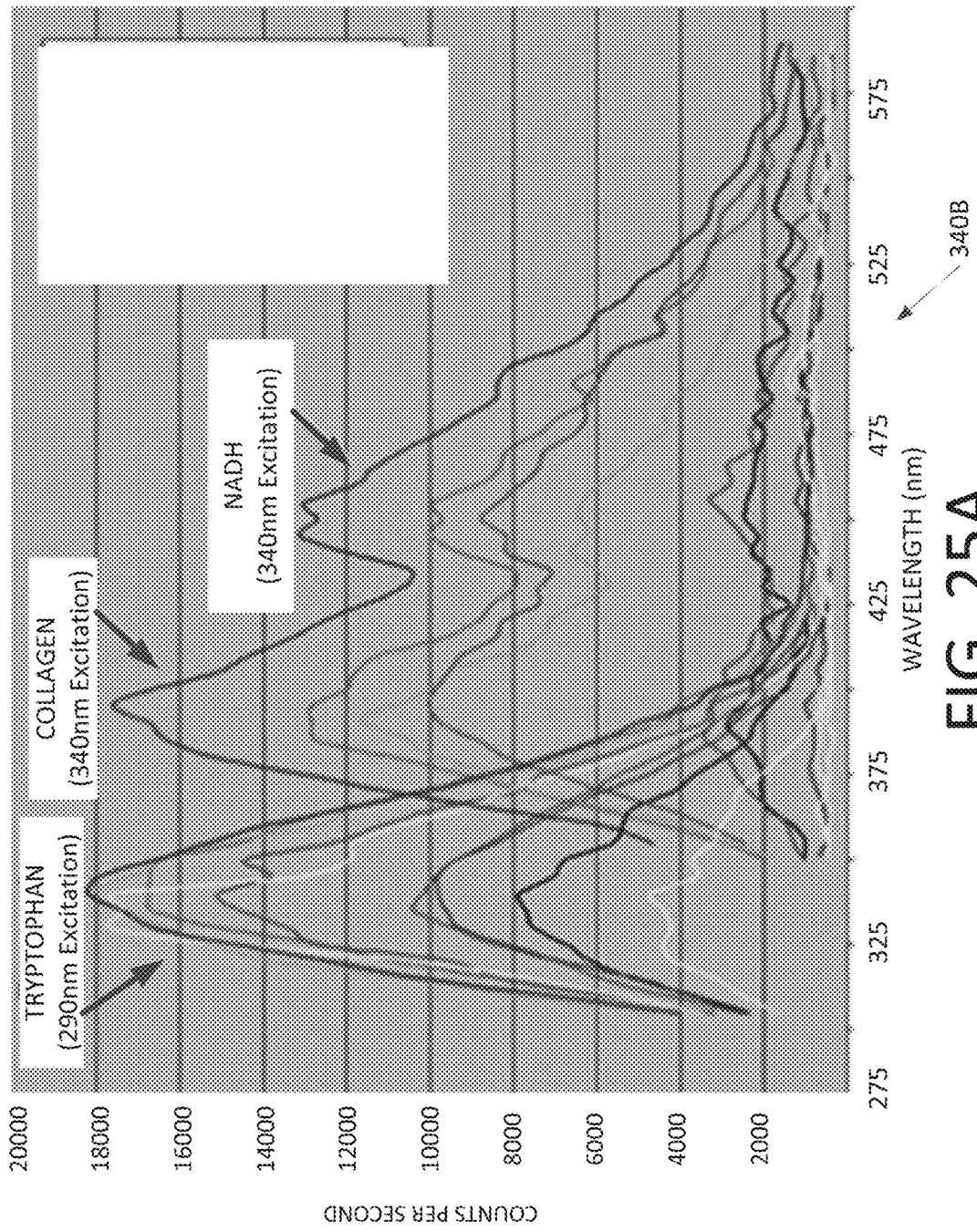
FIG. 25A illustrates one photograph 340B which illustrates fluorescence spectra captured from the location or vicinity of the cancer lesion shown in MRI/US fusion image 343D. When the spectra is processed by a tissue classification algorithm, it can either confirm or contradict the existence of cancer lesion shown in MRI/US fusion image for 3D optical mapping of the prostate.
Figure 25B:
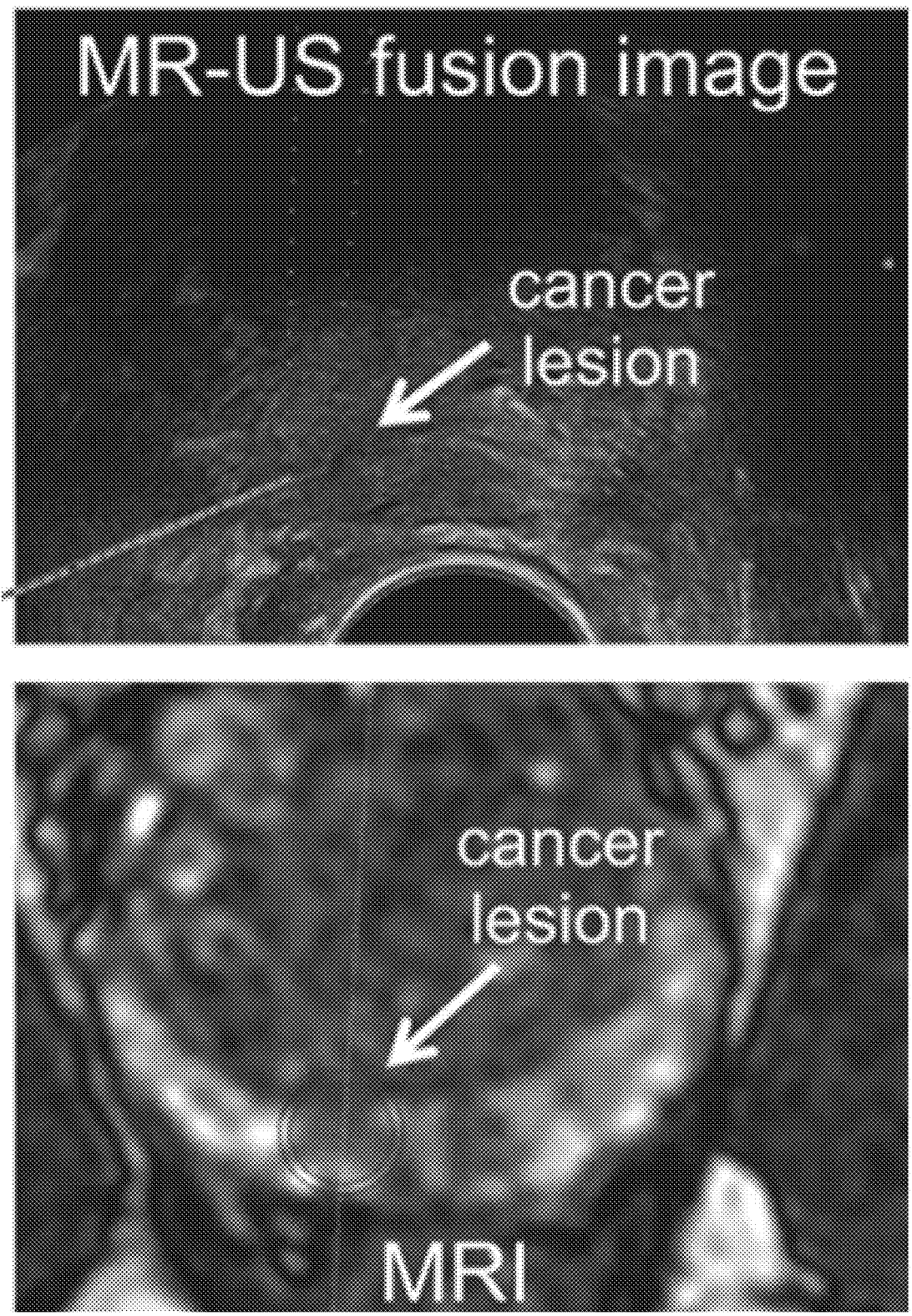
FIG. 25B illustrates two photographs, the lower photo 343C is an MRI image where a cancer lesion was first diagnosed by a radiologist and the upper photo 343D is a MRI fusion image showing a cancer lesion fused with an ultrasound (US) image.

As another example, FIG. 25B illustrates two photographs, the lower photo 343C is an MRI image where a cancer lesion was first diagnosed by a radiologist and the upper photo 343D is a MRI fusion image showing a cancer lesion fused with an ultrasound (US) image. This combined MRI/US fusion image can be used for transrectal or transperineal directed biopsy of the prostate. When an optical biopsy needle 334 is used, an additional fluorescence spectra can be generated in the computer monitor display 340 from the location or vicinity of the cancer lesion shown in MRI/US fusion image. FIG. 25A illustrates one photograph 340B which illustrates fluorescence spectra. This fluorescence spectra presented on display 340 when processed by a tissue classification algorithm can either confirm or contradict the existence of a cancer lesion shown in MRI/US fusion image 343D.

For example, a system for use with a tissue to create a fused image includes the optical probe array 74 in combination with a MRI or CT imaging guidance system 141 for identifying the position of the optical probes relative to the tissue. In addition, an ultrasound imaging guidance system 114 identifies the position of the optical probes relative to the tissue. A three-dimensional user interface imaging system 116 generates a three-dimensional image of the tissue based on the generated light signals and the identified position of the optical probes 74 as indicated by the MRI imaging guidance system 141 and as indicated by the ultrasound imaging guidance system 114. The resulting images as shown in FIGS. 24A-25B are a fusion of an MRI (or CT) image provided by the MRI (or CT) imaging guidance system 141 and an ultrasound image provided by the ultrasound imaging guidance system 114. As noted herein, MR, CT, or fusion images can be used to guide prostate biopsies to cancer lesions identified by the radiologists. The optical biopsy needle 134 provides additional information by elastic scattering spectra or fluorescence spectra or both. This information after processed by a tissue classification algorithm indicates whether a cancer lesion shown by the images indeed is cancer or not.

Thus, in one form, a system as shown in FIG. 10 is for use with a tissue. An optical probe array system 112, 115 has at least two or more optical probes for inserting into the tissue, for illuminating the tissue and for generating light signals corresponding to the illuminated tissue. An imaging system 116, 117 generates an image of the tissue based on the generated light signals.

Thus, in another form, a system as shown in FIG. 10 is for use with a tissue. An optical probe array system 112, 115 has at least two or more optical probes for inserting into the tissue, for illuminating the tissue and for generating light signals corresponding to the illuminated tissue. An imaging system 114, 116, 117 generates an image of the tissue based on the generated light signals.

Thus, in another form, a system as shown in FIG. 13 is for use with a tissue 138. An optical probe array system 132 has at least two or more optical probes 134 for inserting into the tissue, for illuminating the tissue 138 and for generating light signals corresponding to the illuminated tissue. An imaging system 136, 140 generates an image of the tissue based on the generated light signals.

Thus, in another form, a system as shown in FIG. 23 is for use with a tissue 338. An optical probe array system 332 has at least two or more optical probes 334 for inserting into the tissue, for illuminating the tissue 338 and for generating light signals corresponding to the illuminated tissue. An imaging system 336, 340, 341, 343 generates an image of the tissue based on the generated light signals.

Thus, in another form, a system as shown in FIG. 23 is for use with a tissue 338. An optical probe array system 332 has at least two or more optical probes 334 for inserting into the tissue, for illuminating the tissue 338 and for generating light signals corresponding to the illuminated tissue. An imaging system 336, 340 generates an image of the tissue based on the generated light signals.

Thus, in another form, a system as shown in FIG. 23 is for use with a tissue 338. An optical probe array system 332 has at least two or more optical probes 334 for illuminating the tissue 338 and for generating light signals corresponding to the illuminated tissue fluorescence and/or corresponding to the illuminated tissue diffuse reflectance spectroscopy for distinguishing between cancer tissue and non-cancer tissue. A controller 336 and display 340 generate an image corresponding to the generated light signals. An MRI or CT image indicative of the position of the optical probes relative to the tissue (stored on a storage device) is generated by an imaging system 341. An ultrasound imaging guidance system for identifying the position of the optical probes relative to the tissue is part of the imaging system 341. The imaging system 341 generates an image (see photograph 343B, 343D) of the tissue on display 343 based on the identified position of the optical probes 334 as indicated by the MRI or CT imaging guidance system 341 and as indicated by the ultrasound imaging guidance system. The generated image is a fusion of an MRI or CT image provided by the MRI or CT imaging guidance system and an ultrasound image provided by the ultrasound imaging guidance system. A treatment device 339 employing a treatment modality such as described herein can be used in combination with the imaged and/or mapped tissue to treat the imaged tissue. For example, the device 139 can be a Cryotherapy device; a Photodynamic Therapy device; a Brachytherapy device; a high-intensity focused ultrasound (HIFU) device; a tissue ablation device; a Laser ablation device; a RF ablation device; a Vapor ablation device; and a Local drug delivery device.

In summary of one embodiment, a physician will introduce the optical probe under imaging guidance (e.g. ultrasound, MRI, CT) into specific regions of the prostate using a spatial template. The physician will then systematically perform an optical sampling of the prostate to create a 3-D mapping of the prostate where both benign and malignant sites are identified and recorded. With this 3-D mapping the physician can then return to the malignant sites and deploy therapeutic modalities. Optionally, other images from systems such as MRI and CT scans combined with TRUS image (Image fusion of TRUS and MRI or TRUS and CT) can be communicated into the fluorometer and overlapped with optical measurements.

The measurement points where the tissue classification algorithm has classified as abnormal may be displayed with a different color than the normal tissue. The location of the abnormal tissue with respect to transrectal ultrasound system may also be provided by the optical system so the physician can easily locate the abnormal tissue under ultrasound and deliver therapy to the appropriate location.

Design and Materials

The optical probe is an elongated hypodermic needle with a fiber optic bundle passing through an internal bore. The fiber optic bundle is comprised of at least one transmitter fiber and at least one receiver fiber to form an optical sensor(s). The needle is capable of accommodating optical sensors both at the distal tip and various positions along its length. The transmitter fiber optics transmit light from a light source or light sources (e.g. light-emitting diode or laser) to the tissue under examination. Multiple light sources may be routed to the fibers either individually or simultaneously by way of optical guides (e.g. focusing lenses or mirrors). The receiver fiber optics transmit light reflected from or subsequently emitted by the tissue under examination to at least one detector or sensor. The light sources and light detector are controlled by computer or similar electronic control that comprises a microprocessor, storage, display, and graphical user interface (GUI). Signals generated by the detector are processed through a diagnostic algorithm and stored.

The component for generating the 3-D diagnostic mapping couples diagnostic information from the spectroscopic evaluation with the spatial location of the respective optical sensors at the time of acquisition. The 3-D mapping system comprises a computer with graphical display, graphical user interface, and software that integrates inputs from the diagnostic algorithm and the imaging system (e.g. ultrasound or MRI).

In one embodiment, a physician will introduce the optical probe under imaging guidance (e.g. ultrasound, MRI) into specific regions of the prostate using a spatial template. The physician will then systematically perform an optical sampling of the prostate to create a 3-D mapping of the prostate where both benign and malignant sites are identified and recorded. With this 3-D mapping the physician can then return to the malignant sites and deploy therapeutic modalities. For example, the physician would insert a 2×2 probe and the system would sequentially excite each of the optical sensors in order to determine the configuration of tissue adjacent to, contiguous to and/or in contact with the probes. The system knows the position of each sensor relative to each other and relative to the tissue (based on the USP) and would store the resulting information. Next, the physician would re-insert the probe at a different, adjacent location and the excitation and measuring process would be repeated. Additional insertions may be needed until the tissue of insert is measured and a complete 3-D map is generated.

Integrated 3-D Mapping and Therapy System

The 3-D mapping system can be used with all therapeutic modalities to diagnose and treat prostate cancer patients. The system initially optically maps the prostate and identifies the locals of the abnormal tissue. Either using the same probe with optical sensors or another probe, any of the therapies, such as the mentioned in therapy section of this application (or others), may be applied.

Motorized Imaging

Introduction

Prostate cancer is the most frequently diagnosed non-cutaneous malignancy among U.S. men. In 2015, an estimated 220,800 men will be diagnosed with prostate cancer and 27,540 are expected to die from this disease. Undiagnosed prostate cancers are at high risk of spreading and metastasizing to other organs, in particular to the bone. Therefore, early diagnosis of this disease is critical. The "gold standard" for prostate cancer diagnosis is histopathological assessment of tissue obtained using transrectal ultrasound (TRUS)-guided prostate biopsy. Approximately one million men undergo TRUS-guided prostate biopsies each year in the U.S.

TRUS biopsies are taken randomly without targeting specific cancer lesions since TRUS is not designed to accurately identify prostate cancer lesions. TRUS images only show anatomical boundary of the prostate gland for guidance of prostate biopsies. TRUS biopsies may fail to provide accurate assessment of the extent of the disease with respect to laterality (unilateral versus bilateral disease) or tumor burden. One study found 66% of patients with unilateral disease on TRUS biopsy findings had bilateral disease on final pathology after surgery. Initial TRUS biopsies diagnosed all 180 patients with unilateral cancer in the previously described study. Among these patients, 110/180 (61.1%) were later up-staged to bilateral cancer following TMB. In the study conducted at the University of Colorado Hospital, 82/180 patients were up-staged by TMB as a result of either increase in the number of positive cores on Trans-perineal Mapping Biopsy (TMB) by 2 or more than that on TRUS biopsy (i.e., tumor burden) or TMB detecting bilateral disease compared to unilateral disease on TRUS biopsy. The major shortcomings of current systematic TRUS-guided prostate biopsies can be summarized as follows:

Low cancer diagnostic yield

High false negative rates

Over- or underestimate patient's correct Gleason Score

Under-sampling of the anterior prostate

Systematic targeting of cancer lesions is difficult

Failure to Provide Accurate Assessment of the Extent of the Disease

The diagnostic accuracy of prostate biopsies can be improved by classifying underlying tissue as normal versus suspicious using optical spectroscopy techniques as a precursor to biopsy. There are several advantages of using optical spectroscopy for cancer diagnosis; it is quantitative, fast, and sensitive to intrinsic biomarkers of tissue such as histopathological grade. The light-tissue interaction is characterized by the physical nature of light and specific tissue morphology and composition.

In fluorescence spectroscopy, one or more narrowband light sources are used to excite endogenous fluorophores and the emission spectrum at each excitation wavelength is detected. The auto-fluorescence spectra (AFS) depend on several important endogenous fluorophores such as tryptophan, collagen, nicotinamide adenine dinucleotide (NADH), flavin adenine dinucleotide (FAD), and others. Quantitative analysis of AFS obtained from tissue can provide valuable information regarding biochemical changes that correlate with disease status. In diffuse reflectance spectroscopy, light is delivered to tissue and after several successive scattering and absorption events it re-emerges from the tissue. Hence, diffuse reflectance spectra (DRS) have information regarding size and shape of cells and intracellular structures of tissue underneath.

Overview of Exemplary Motorized Device

An optical biopsy needle obtains a correlative tissue biopsy core after the optical characterization of underlying tissue. The needle uses a standard laboratory fluorometer to collect auto-fluorescence spectra (AFS) and correlative tissue biopsy cores from surgically excised prostate. Study results showed 86% sensitivity, 87% specificity, 90% negative predictive value, and 83% positive predictive value for separating malignant cores from benign cores.

A US patent (U.S. Pat. No. 8,406,858 B2) has been awarded to the University of Colorado for the aforementioned optical biopsy needle technology. Based on this technology, the ClariCore™ Optical Biopsy System ("ClariCore™ System") obtains TRUS-guided prostate biopsies in the clinical settings following optical characterization of underlying prostate tissue. Optical characterization is binary: either 'Normal' or 'Suspicious.'

The ClariCore™ System comprises the following components:

Optical Biopsy Needle (OBN), which transmits light energy and performs biopsy

Handpiece, which houses the OBN and provides the connection to the console

Console, which provides the primary interface between the user and device

System Software, which contains the analytical algorithm

In one form, the OBN comprises a 16-gauge (1.59 mm) outer cannula and a slightly smaller diameter (1.36 mm) inner needle that houses an optical sensor. The working length of the needle is 25 cm. The optical sensor utilizes a single 200 µm fiber for tissue excitation as well as collecting auto-fluorescence spectra (AFS) and diffuse reflectance spectra (DRS). The handpiece has a built-in stepper motor for auto-advancing the inner needle at 1 mm increments up to 18 mm. The stepper motor is synchronized with the fluorometer for tissue excitation and collecting spectral data at each 1 mm increment. The handpiece has three buttons; 1) to initiate auto-advancement of the inner needle with optical sensor, 2) to release the outer cannula for cutting a tissue core, and 3) to manually or automatically retract/energize the cannula for revealing the tissue notch and cocking the device for the next sample. The handpiece connects to the console via three connectors; one for excitation transmission through the optical sensor, second for collecting tissue spectra, and a third for synchronization/communication of the handpiece electronics with the Console.

The console, with a touch-screen monitor, comprises four main modules: Excitation Unit (EU module 1342), Detection Unit (DU module 1344), Computer Controlled Unit (CCU module 1346) and Master Control Unit (MCU module 1348). The EU module 1342 comprises three light sources: 280-290 nm and 340 nm excitation sources for AFS and 450-700 nm broadband light source for DRS. The DU module 1344 comprises a spectrophotometer to collect corresponding tissue spectra. The CCU module 1346 comprises a computer motherboard and associated peripheral devices. The MCU module 1348 has its own microcontroller and communicates with and controls the excitation sources of EU module 1342. It also communicates with the handpiece 1350 and synchronizes spectral data with the EU module 1342 and auto-needle advancing. Main functions of the control board of the MCU module 1348 include synchronization of data collection with auto-needle advancing, optical characterization of tissue, display results on the monitor, and user inputs from the monitor. User interface software supports the Graphical User Interface (GUI) for interacting with the user.

Figure 26:
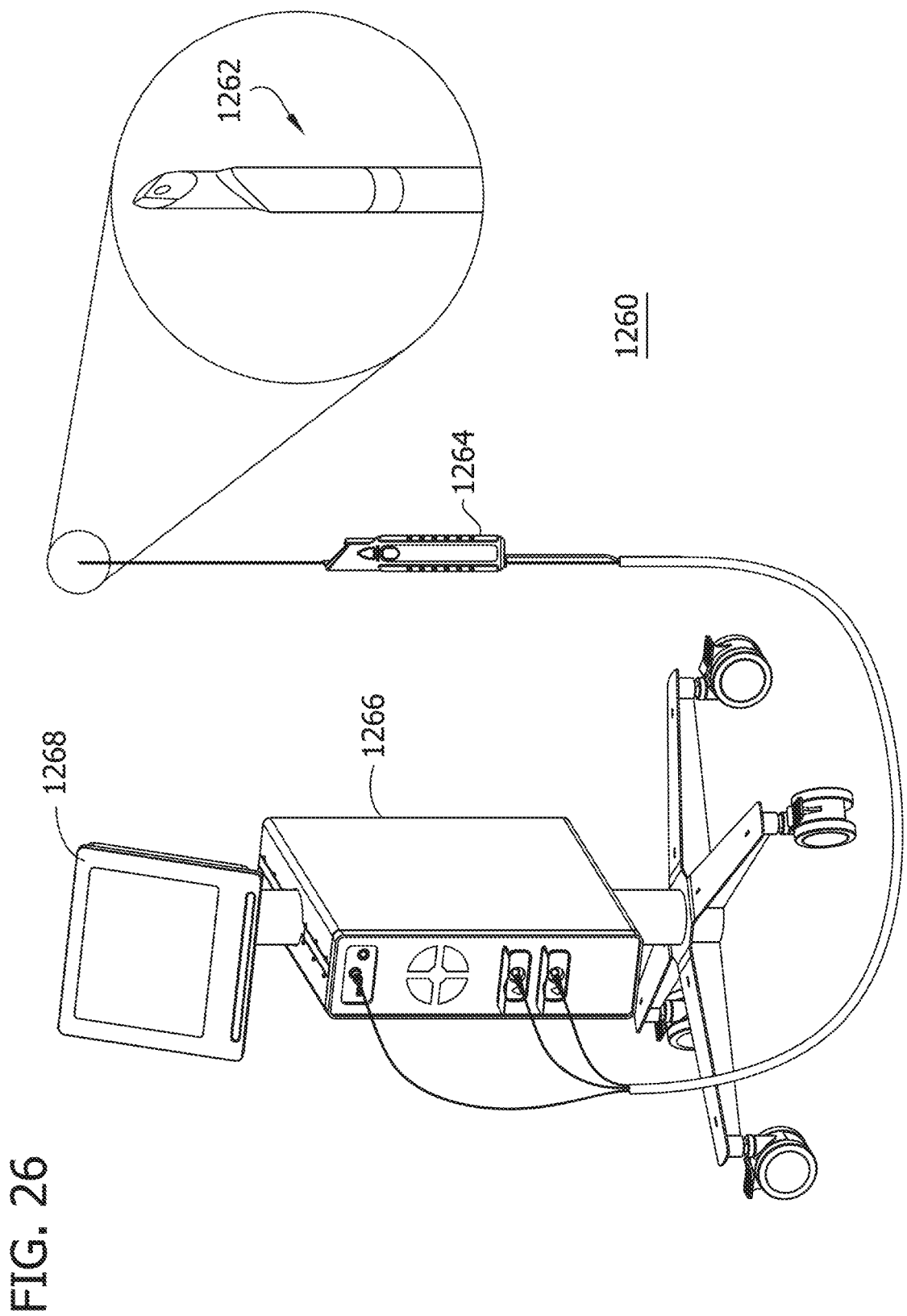
FIG. 26 illustrates in one form the components of the ClariCore™ System.

The components of the ClariCore™ System 1260 in one form are illustrated in FIG. 26.

Figure 27:
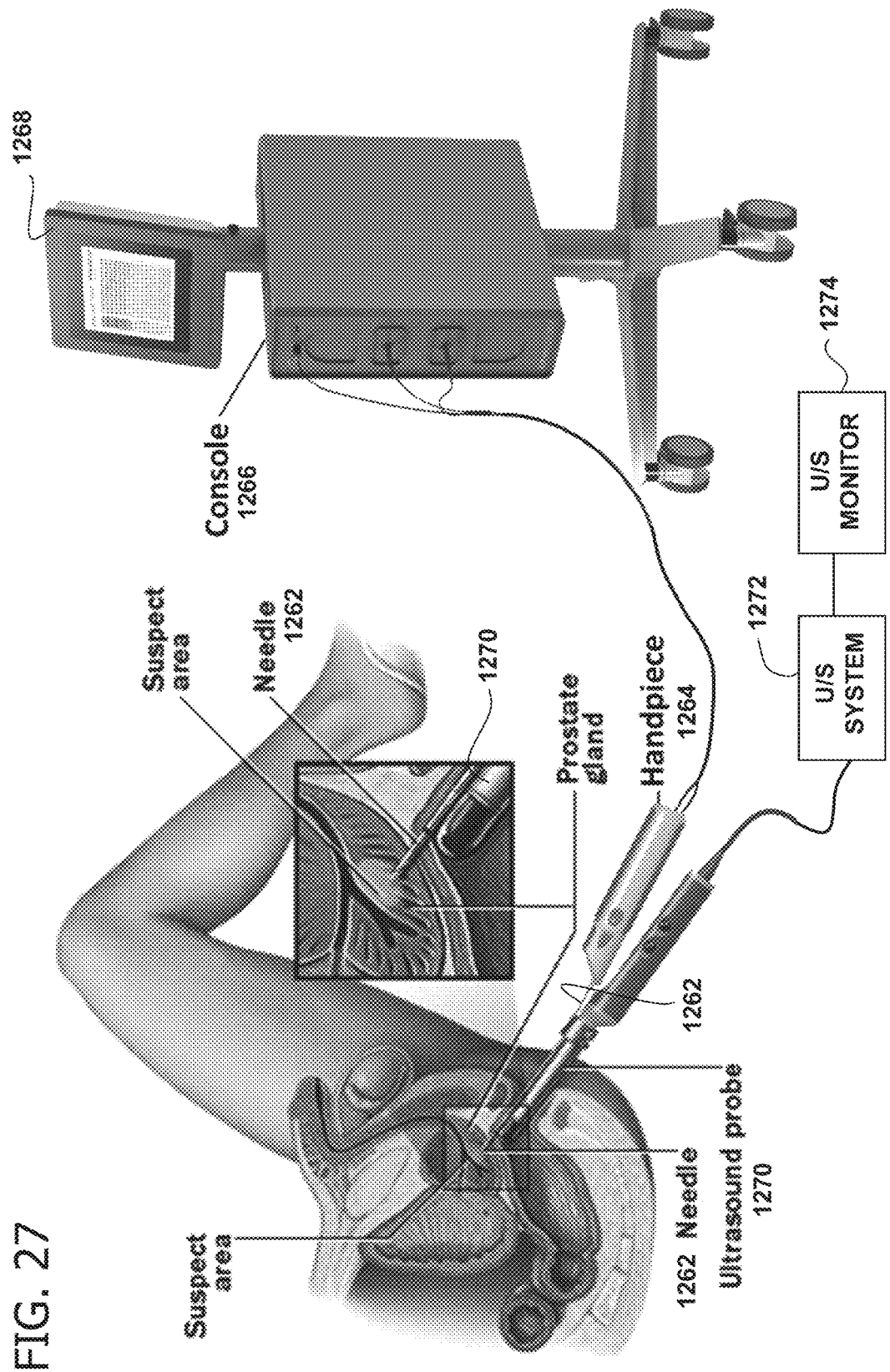
FIG. 27 depicts in one form the ClariCore™ System and its clinical placement.

Use of the ClariCore™ System has been designed to follow standard TRUS biopsy procedures (FIG. 27).

In one form, the ClariCore™ System, similar to standard TRUS biopsy, is used as follows. With the Optical Biopsy Needle (OBN 1262) inserted in the ultrasound probe 1270 connected to the ultrasound system 1272, the urologist first manually inserts the OBN 1262 a few millimeters inside the prostate by piercing through the prostate capsule. The urologist is able to observe the OBN penetration depth on the ultrasound monitor 1274. A button on the handle 1264 of the OBN 1262 is depressed to activate the auto needle advancement mechanism (see FIGS. 33A and 33B) and depressing the button again will cause the needle advancement to pause. The built-in auto needle advancing mechanism enables incremental advancement of the inner needle in preselected increments (e.g., 1 mm steps) while capturing optical readings of the underlying tissue after each incremental step. The auto needle advancing mechanism will automatically stop after a preset number of increments (e.g., after the 18th 1 mm incremental step). The preset number of increments can be equal to the length of the collection space 1294 (e.g., notch). This is the stop position for the ClariCore™ System.

Figures 28A, 28B:
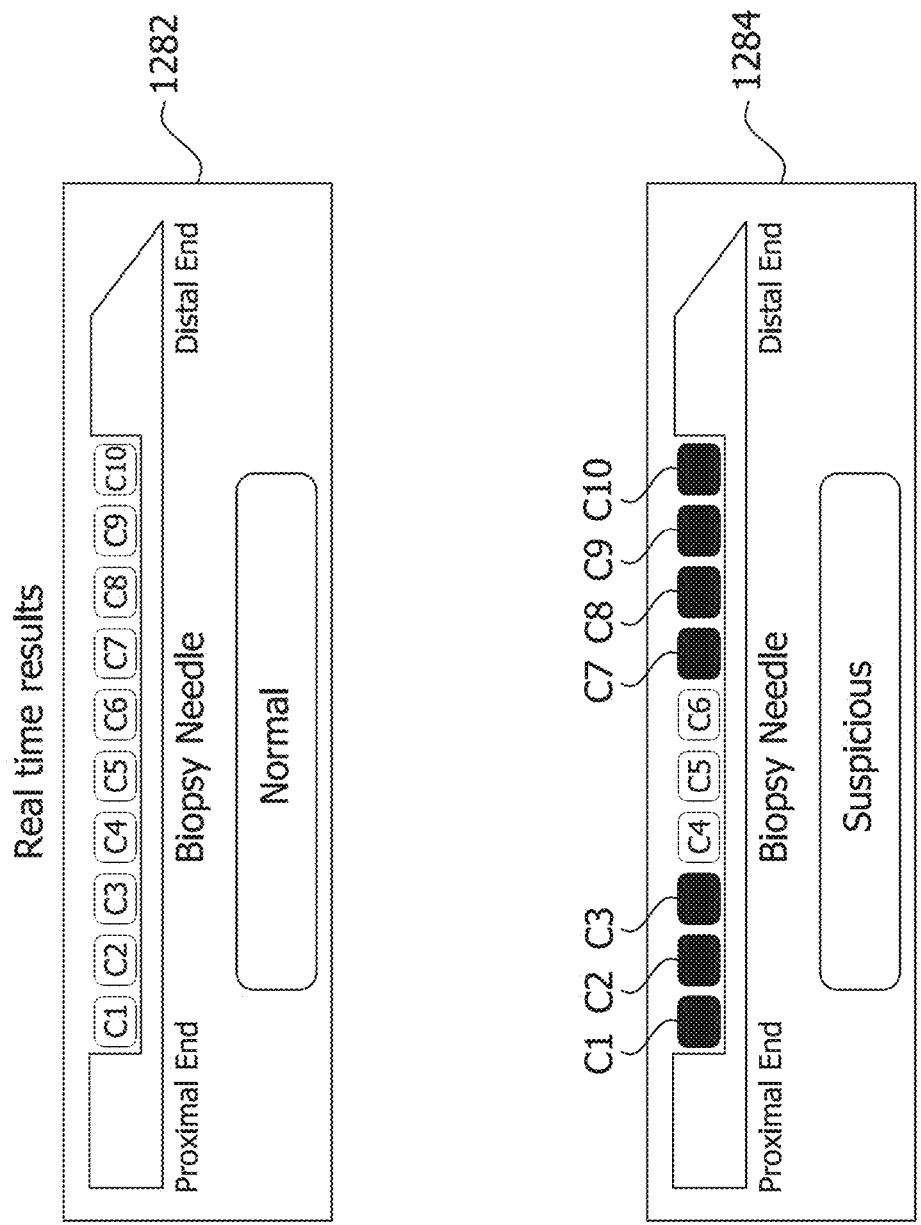
FIGS. 28A and 28B illustrate the normal/suspicious optical reading monitor display achieved by applying a classification algorithm to determine if the tissue is 'Suspicious' at each increment movement of the needle.

At this time, the results of the optical characterization of the tissue will be displayed to the urologist on the touch-screen monitor. The normal/suspicious optical reading is achieved by applying a classification algorithm to determine whether the tissue is 'Normal' 1282 or 'Suspicious' 1284. FIGS. 28A and 28B illustrate the normal/suspicious optical reading monitor display achieved by applying a classification algorithm to determine if the tissue is 'Suspicious' at each increment movement of the needle. FIGS. 28A and 28B illustrate 10 incremental movements of the needle 1292 which correspond to the 10 indications of the tissue classification. Thus, the urologist (an operator) is able to observe the classification of the tissue within the collection space 1294 before releasing the cannula 1290 to obtain a biopsy. FIG. 28A illustrates that all 10 tissue classifications C1-C10 for the 10 increments are all normal and are illustrated in the same color corresponding to normal, such as green. FIG. 28B illustrates that the first 3 tissue classifications C1-C3 for the first 3 increments are suspicious and that last 4 tissue classifications C7-C10 for the last 4 increments are suspicious whereas the 3 central tissue classifications C4-C6 for the 3 central increments are normal. Thus, FIG. 28B illustrates the first 3 and last 4 tissue classifications C1-C3, C7-C10 in the same color corresponding to suspicious, such as red, and the central three classifications C4-C6 in a different color corresponding to normal, such as green.

On the monitor 1268, each 1 mm of the tissue volume will be denoted in "Green" to indicate 'Normal' tissue and in "Red" to indicate 'Suspicious' tissue. When a biopsy sample is desired, the urologist presses the second button on the Handle to advance the Cannula (see FIGS. 33A and 33B) and cut the tissue core. Otherwise, the urologist can remove the Needle 1262 from the prostate without taking a tissue sample. This procedure can be repeated until all preselected biopsy locations are examined.

There are a number of advantages to using the ClariCore™ System for prostate biopsies previously not available to urologists and patients. The ClariCore™ System provides real-time feedback. If all cores are 'Normal', the patient can be informed immediately rather than waiting two to ten days for the histopathological results. The ClariCore™ System may increase the cancer diagnostic yield of prostate biopsies by focusing acquisition of biopsy cores from locations indicated as 'Suspicious.' The ClariCore™ System may reduce the high false negative rates of prostate biopsies by giving the urologist the opportunity to probe extra locations including the anterior prostate when previous locations are indicated as 'Normal.' Additional probing of new biopsy locations may facilitate increase in suspicious tissue biopsy samples thereby reducing false negative rates.

If desired, the urologist has the opportunity to probe within the vicinity of location(s) indicated as 'Suspicious' when using the ClariCore™ System. Optical analysis of tissue samples from 'Suspicious' location(s) and their neighboring locations may lead to better assessment of the suspicious tissue and aid the pathologists in diagnosing the true extent of the disease with respect to laterality and tumor burden. The ClariCore™ System may eliminate under sampling of the anterior prostate. Some urologists may avoid taking biopsies from the anterior prostate due to fear of perforating the prostate capsule and penetrating adjacent anatomical structures when activating the biopsy gun. However, use of the ClariCore™ System enables the urologist to maintain a safe distance from prostate boundary when activating the controlled needle advancing mechanism and obtaining the tissue core.

Detailed Description of Exemplary Motorized Device

The ClariCore™ System 1260 comprises an Optical Biopsy Needle (OBN) 1262 and Handpiece Assembly 1264 that connects to a system Console 1266 (FIG. 26). In one form, the system uses non-ionizing LED (light emitting diode) light sent from an excitation source (in the system Console) to stimulate fluorescence and diffuse reflectance emission from the tissue in contact with the optical sensor at the distal tip of the OBN. The light from the emission is transmitted back to the Console to be interpreted by the algorithm. Based upon the spectral data, the algorithm classifies the tissue as 'Suspicious' or 'Normal' and allows the physician to perform "targeted" biopsies.

The ClariCore™ System comprises the following components:
  Optical Biopsy Needle (OBN), which transmits light energy and performs biopsy
  Handpiece, which houses the OBN and provides the connection to the console
  Console, which provides the primary interface between the user and device
  System Software, which contains the analytical algorithm
  The components of the ClariCore™ System are described below.

Optical Biopsy Needle (OBN)

Figure 29:
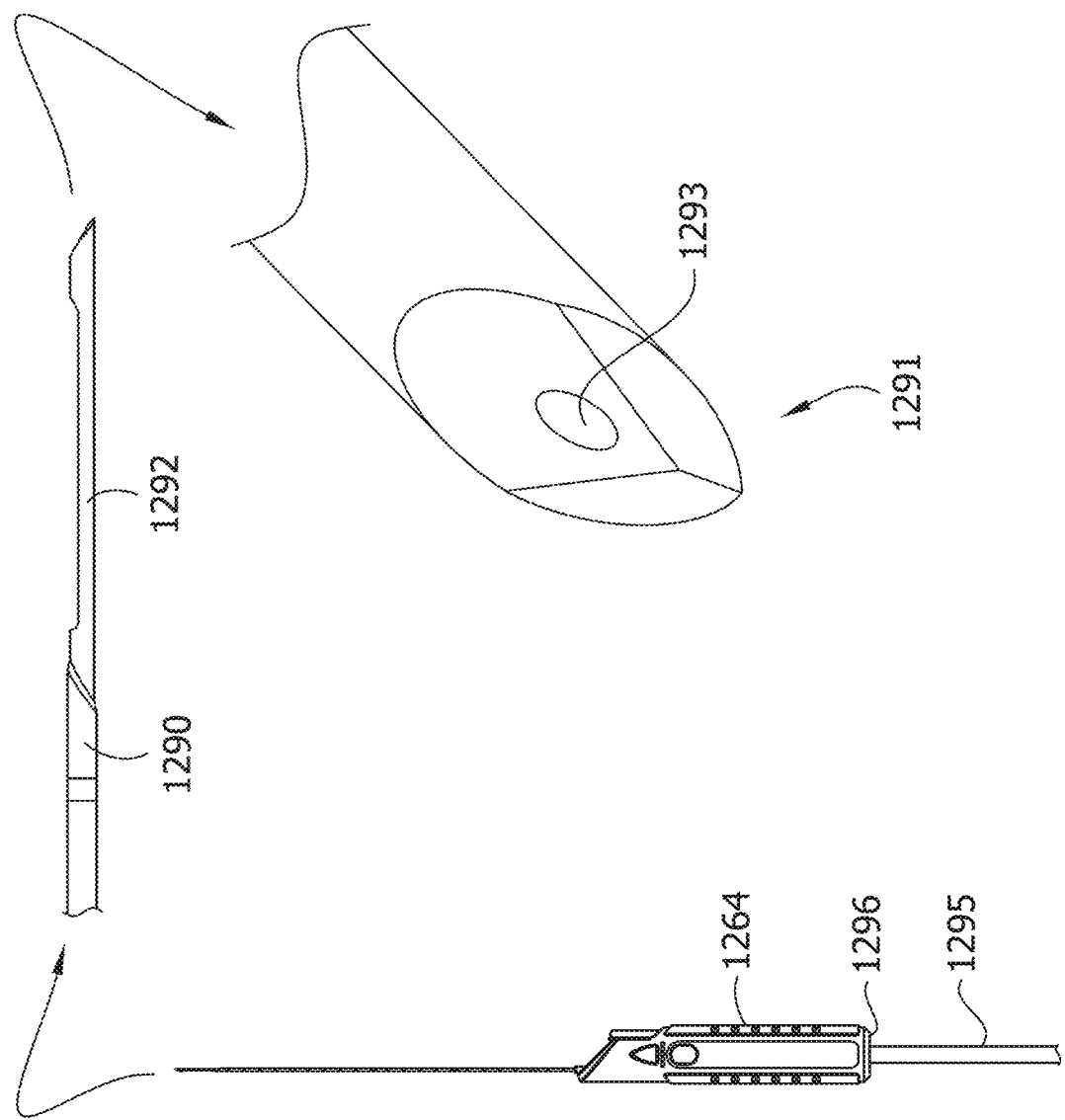
FIG. 29 illustrates in one form the OBN composed of a 16-gauge (1.59 mm) stainless steel cannula with an open beveled-tip configuration and a slightly smaller diameter (1.36 mm) inner needle with embedded optical fiber and a space for sample collection (19 mm sample notch), cable wraps and connectors.

The OBN is composed of a 16-gauge (1.59 mm) stainless steel Cannula 1290 with an open beveled-tip configuration 1291 and a slightly smaller diameter (1.36 mm) Inner Needle 1292 with embedded optical fiber 1293 and a collection space 1294 (a sample notch) for sample collection (19 mm sample notch), cable wraps 1295 and connectors 1296 (FIG. 29). The working length of the Inner Needle is 25 cm. The optical sensor, at the distal tip of the Inner Needle, utilizes a single 200 µm fiber for tissue excitation and collecting auto-fluorescence spectra (AFS) and diffuse reflectance spectra (DRS).

Figure 30:
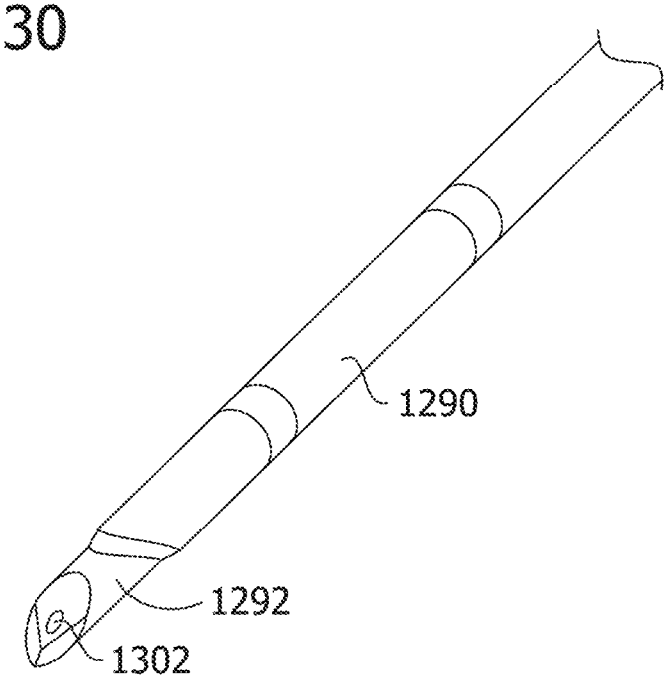
FIG. 30 illustrates in one form the tip of the OBN containing the single exposed fiber as an optical sensor for light source and detection. The outer beveled Cannula overlays the Inner Needle and is used to shear and collect tissue samples.
Figure 31:
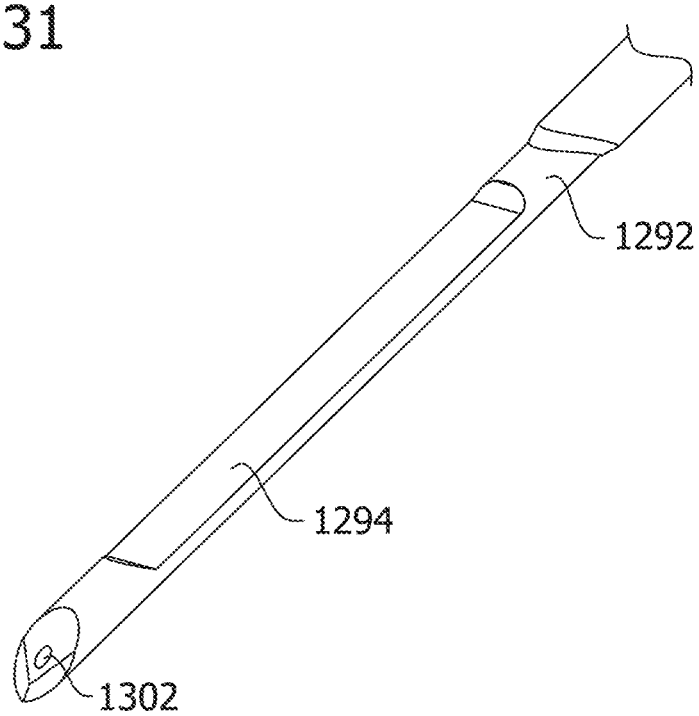
FIG. 31 illustrates in one form the sample notch (e.g., collection space of 19 mm) at the distal end of the inner needle used to chamber the excised biopsy core.

The tip of the OBN contains the single exposed fiber as an optical sensor 1302 for light source and detection (FIGS. 30 and 31). The outer beveled Cannula 1290 overlays the Inner Needle 1292 and is used to shear and collect tissue samples. The collection space 1294 (i.e., the sample notch, 19 mm) at the distal end of the Inner Needle is used to chamber the excised biopsy core (FIG. 31). The OBN 1262 is integrated into the Handpiece 1264.

Handpiece

Figure 32:
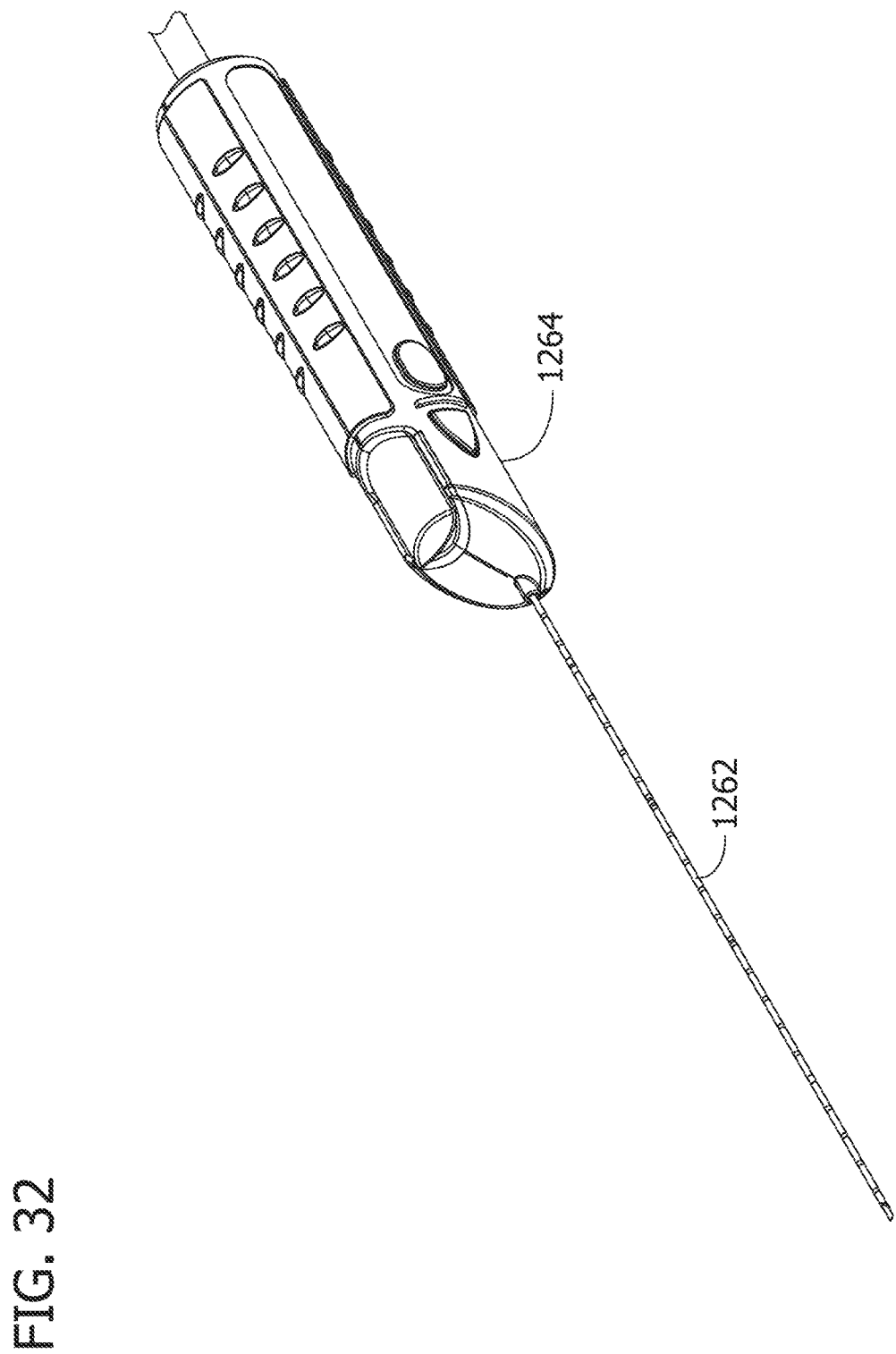
FIG. 32 illustrates in one form the Handpiece and OBN having integrated fiber optics, and electrical and optical cabling to interface with the system Console. The Handpiece is an enclosed assembly that houses the OBN (ref.). The Handpiece contains electro-mechanical interfaces (motor and chassis) and has three operational buttons by which the physician controls the advancement of the Inner Needle and Cannula into selected regions of the prostate tissue under TRUS guidance.

The Handpiece 1264 and OBN 1262 have integrated fiber optics, and electrical and optical cabling to interface with the system console. The Handpiece 1262 is an enclosed assembly that houses the OBN 1264 (FIG. 32). The Handpiece 1262 contains electro-mechanical interfaces (motor and chassis) and has three operational buttons by which the physician controls the advancement of the Inner Needle 1292 (guided by inner needle sled 1337) and Cannula 1290 (guided by cannula sled 1338) into selected regions of the prostate tissue under TRUS guidance. The Handle 1330 houses the DC stepper motor 1331 (connected to electrical cable 1339) for auto-advancing the Inner Needle 1292 in 1 mm increments up to 18 mm, see FIGS. 33A and 33B. The stepper motor 1331 is synchronized with the fluorometer for tissue excitation and collection of spectral data at each 1 mm increment. The handpiece 1264 connects to the console 1266 via three connectors: one for excitation transmission through the optical sensor 1302, second for collecting tissue spectra, and a third for synchronization/communication of the Handpiece 1264 electronics with the console 1266.

The Handpiece 1264 has three buttons to control the advancement of the Inner Needle 1292 with the optical sensor 1302 (advancement button 1333), fire the Cannula 1290 (cannula release button 1334 which allows a spring to advance the cannula) to obtain a tissue biopsy and to cock the lever (cannula retraction button 1335) for retracting the Cannula 1290 to reveal the Sample Notch 1294 and tissue sample, respectively (FIGS. 33A and 33B). It is contemplated that any advancing device can be used to advance the cannula such as a spring as shown in FIGS. 33A and 33B, or a motor, or a combination thereof.

Once the sample has been removed, the physician homes the optical sensor 1302 by touching the sensor 'home' tab on the monitor 1268. The built-in stepper motor 1331 mechanism in the Handpiece 1264 enables incremental advancement of the Inner Needle 1292 in 1 mm steps (up to 18 mm) monitored by advancement sensor 1336 while obtaining optical readings of the underlying tissue at each increment. The stepper motor 1331 is synchronized with the EU module 1342 and DU module 1344 in the Console 1266 for tissue excitation and collection of spectral data, respectively, at each 1 mm increment. Once the physician receives spectra or optical characterization of tissue for each 1 mm step, the physician manually fires the Cannula 1290 to obtain desired tissue sample(s).

The OBN is designed and made of medical grade materials that are widely used in the medical industry and the Handpiece is made of various plastic polymers molded parts and metal components.

The OBN/Handpiece Assembly and cables are provided sterile to the user as a single-use, disposable device.

Console

The Console 1266 is housed in a transportable self-contained cabinet. The Console 1266 has a user interface system with display (e.g., touch-screen monitor 1268), audio components and operation buttons. As noted above, there are four main components installed in the Console: an Excitation Unit (EU 1342), Detection Unit (DU 1344), Computer Controlled Unit (CCU 1346) and Master Control Unit (MCU 1348). The CCU module 1346 comprises a computer motherboard and associated peripheral devices. Its main functions are executing application software for Graphical User Interface (GUI) and communication with DU, MCU and to external Networks. The MCU communicates with the Handpiece and synchronizes spectral data with the EU and auto-needle advancing.

Figure 34:
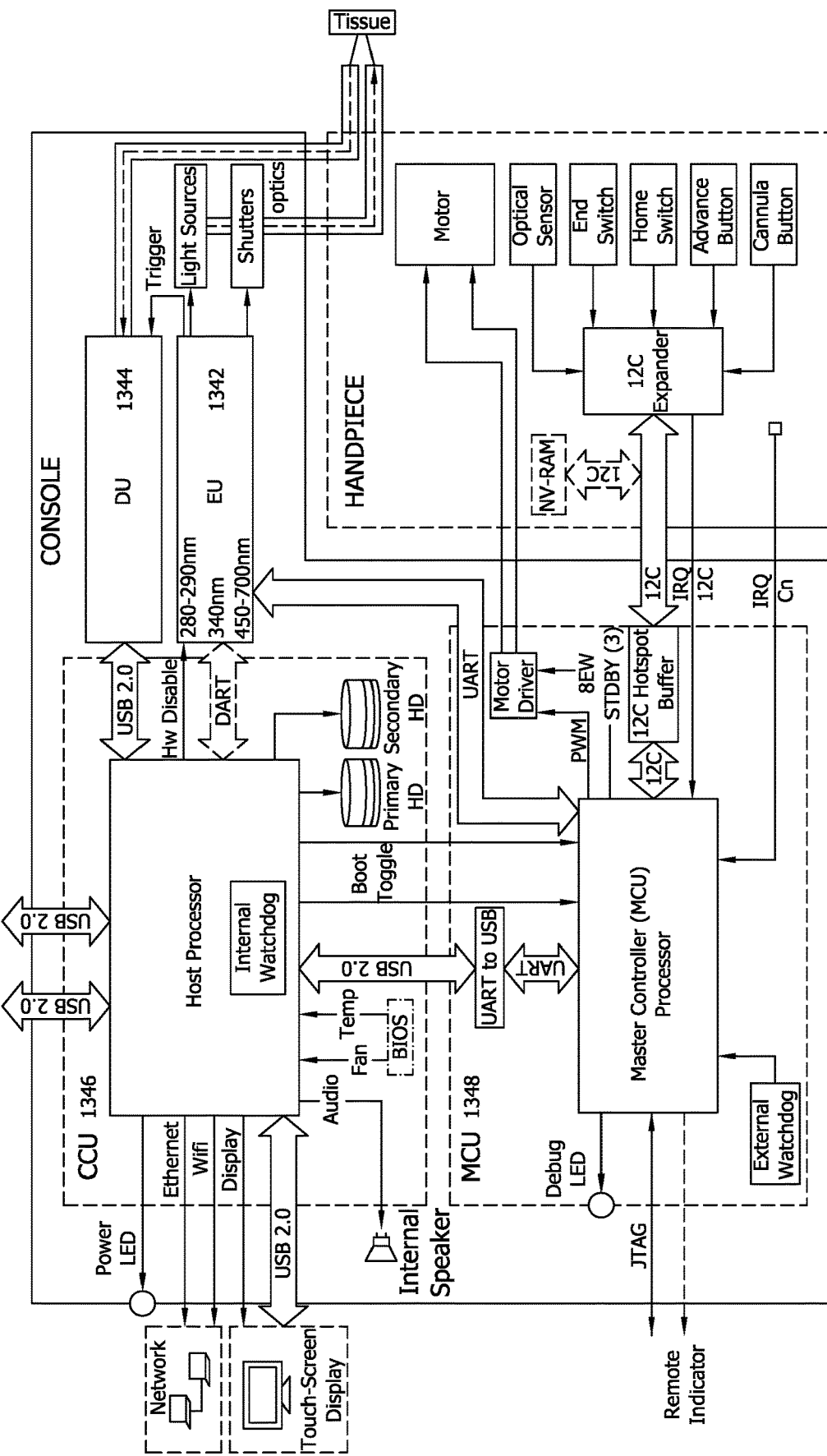
FIG. 34 shows in one form the modules of the Console and the hardware interfaces controlled by the Host and MCU Processors.

FIG. 34 shows the modules of the Console and the hardware interfaces controlled by the Host and MCU Processors.

The Console 1266 is provided fully assembled (and delivered with a monitor and stand). The Console and accessories are provided non-sterile and are reusable.

System Software with Algorithm

Described at a high level, the primary functions of the System Software and Algorithm include:
1. System software that performs various functions such as housekeeping functions, taking user inputs and displaying outputs.
2. Algorithm for tissue classification.

The Console 1266 contains a number of software modules. These include software executing on CCU module 1346, MCU module 1348, EU module 1342, and DU module 1344. The user interface software supports GUI for interacting with the user. It allows user inputs from the monitor 1268 including patient data prior to the procedure and display results on the monitor following optical characterization of tissue.

Figure 35:
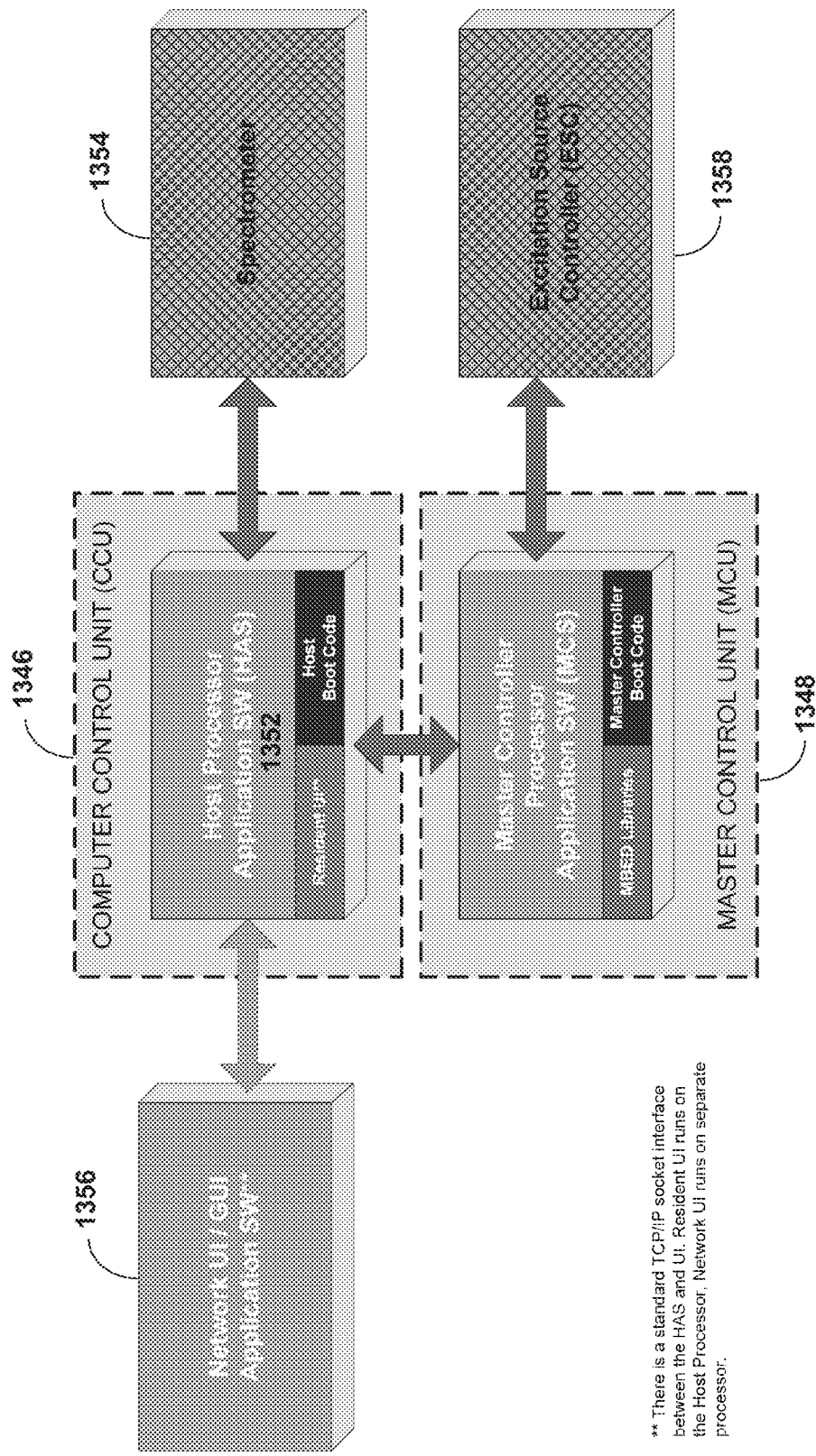
FIG. 35 illustrates in one form each functional block of the system representing an independent software item of the console (note: the embedded software for the spectrometer and excitation source are separate).

Each functional block represents an independent software item of the Console 1266. The embedded software for the spectrometer and excitation source are separate, see FIG. 35. The CCU module 1346 includes a processor executing HAS (host application software) instructions 1352 for connecting to and coordinating operation between a spectrometer 1354, a network user interface software 1356 and the MCU module 1348. The CCU module 1346 includes a resident user interface software and host boot code instructions. The MCU 1348 module executes MCS (master control software) instructions for connecting to and coordinating operation between the CCU module 1346 and an ESC (excitation source controller). The MCU module 1348 includes MBED libraries and master controller boot code instructions. In one form, there is a standard TCP/IP socket interface between the HAS and UI. The resident UI runs on the Host Processor 1352 and the network UI runs on a separate processor.

CCU or Host Processor and HAS

The CCU module 1346 processor or 'Host' processor is the central controller of the system 1260. Software running on the Host processor is denoted as "Host Application Software" or "HAS". All supervisory tasks (non-safety critical) are handled by the HAS on the Host processor, which follows the IEC 62304 guidelines pertaining to a Class B device. Any UI designated to run on the Host processor is referred as a "Resident UI". [Note: Other UI not run on the Host processor are referred to a "Network UI".]

The Host processor is running the HAS and Resident UIs in the CentOS Operating System (OS). The code for the HAS is written in C++.

HAS supervises and coordinates the other software modules of the Console 1266. The primary responsibilities of HAS include:

- Via communications with the MCS (master control software): request Handpiece 1264 needle advancements or retractions, set or retrieve parameters of operation and report system events and errors;
- Via communications with the Excitation Source Controller (ESC) and Spectrometer: request turn on/off the UV LEDs, open/close main shutter through MCU (master control unit), request or retrieve emission spectral data, disable the ESC or Spectrometer;
- Via communications with the UI: send updated procedural information, report system events and errors and receive command requests.

HAS Interface to the Algorithm

The system software includes a Tissue Classification Algorithm (TCA) that analyzes the spectra data collected by the Spectrometer. Based upon the spectral data, the algorithm classifies the tissue. Optical characterization is binary: either 'Normal' or 'Suspicious.' The algorithm/classification software module will classify the measured optical signals based on pre-established criteria. The 'Normal' or 'Suspicious' assignment will be based on the optical signal principle component parameters of the measured signal when compared to a threshold to be derived from pathologically known values of suspicious (or cancerous) and normal (or non-cancerous) measurements in prostate tissue.

The TCA comprises three major components:

- Pre-Processing to remove baseline and DC components of optical data by use of dark (background) spectral data, and to provide optical data whitening (normalization). Optical data with very low signal-to-noise ratio (SNR) are flagged by this step and are not passed to next steps and as a result are classified as "not usable".
- Spectral Components (Features) Extraction by use of principle components analysis or similar methods. This step helps to maintain the necessary information and eliminate redundant and unnecessary information, which is vital to reduce computational time and overtraining of TCA.
- Knowledge-based Tissue Classification (kTC) which is a type of supervised machine learning task of inferring a function from labeled training data (ground truth). The training data is a set of training examples, where each example is a pair of data consisting of a features (Spectral Components) vector and a desired output value (corresponding histopathological reading of the same tissue sample). The kTC algorithm analyzes the training data and produces an inferred function, which can be used to correctly determine the class labels for unseen (testing) data. The class labels are 'Suspicious' and 'Normal'. The TCA after sufficient training and optimization is deployed into HAS (Host Application Software) for real-time tissue classification to 'Suspicious' and 'Normal'.

The HAS will provide an interface to call and to execute the Algorithm, passing it the required data acquired from the spectrometer and receiving the algorithm status. The HAS will have a system event for relaying the algorithm status to the UI, which can then display this status to the user.

Master Controller Processor and Software (MCS)

The Master Controller Software (MCS) (on the MCU module 1348 processor) is written as a stand-alone operation without an OS. All code is written in C++ using the Keil uVision Integrated Development Environment. MCS directly interfaces to and controls the Handpiece motor and sensors on the OBN allowing the user to advance and/or retract it as well as stop it at incremental depths within the tissue under analysis. The MCS controls the direction, velocity and duration of the Handpiece motor 1331 and inputs for optical sensor, advance push-button and Cannula button. The MCU also interfaces to the Excitation Source Controller (ESC), which excites the tissue under analysis at each incremental location with one of three light sources. The Excitation Source controls the excitation light sources (intensity, on/off main shutters and regulation of UV exposure time) with its embedded software. Because of the patient risk of injury, the MCS will follow IEC 62304 guidelines pertaining to a Class C device.

Exemplary Motorized Device Characteristics

The ClariCore™ System characteristics are listed in Table 5.

TABLE 5

| ClariCore System Characteristics | |
|---|---|
| Characteristic | Description |
| Design | Biopsy Handpiece with capability of emission of light and collection of spectra data through fiber optic located at distal tip |
| Anatomic Site | Prostate |
| Method of Placement | Transrectal Ultrasound (TRUS) guided placement |
| Method of Visualization | Ultrasound |
| Mechanics of Action | A) Mechanical (spring-activated) biopsy of tissue and B) Collection of spectra data based on the principle of auto-fluorescence and defuse reflective |
| Mode of Action | Single puncture/sample |
| Relevant Characteristics | Handpiece with a biopsy cannula/needle that contains an optical sensor that is incrementally advanced by 1 mm into the prostate taking spectra at each increment |
| Safety Features | Electro-mechanical interface with software that controls on/off of UV LEDs, open/closes main shutter, and electrical circuits that measure overall exposure can disable the excitation source Alarms: - Alarms may be included. Examples: an alarm may be generated if the exposure limit is reached, or if the Console or Handpiece malfunctions. |

Exemplary System Specifications

Table 6 lists the known component specifications for the ClariCore™ System.

TABLE 6

| System Specifications by Component | |
|---|---|
| OBN/Handpiece Assembly | |
| Cannula Size | 16-gauge |
| Cannula/Needle Material | SS304 |
| Fiber Optics | 200 um diameter, 0.22 NA, High OH Silica, multimode fiber |
| Sample Notch Length | 19 mm |
| Needle Penetration Depth | 22 mm |
| Needle Working Length | 25 cm |
| Depth Gradations on Cannula | Centimeter markings |
| Cable Length | 1.8 m |
| Sterilization Method | EO |
| Operating Voltage | 6 V, 1 Amp max |
| Handpiece Chassis | PC/ABS |
| Console | |
| Dimensions | 122 cm × 68 cm × 68 cm |
| Electrical Safety Classification | Class II |
| Classification | Type BF applied part |
| Power Input (Voltage, Current) | 100-240 V at 50/60 Hz |
| ANSI IESNA RP-27.3-96 Risk Group Classification and Labeling | RG-3 |
| Mode of Operation | Continuous |
| Ingress Protection Rating | IPX0 |
| Operating Temperature and Humidity | 10 to 40° C., up to 85% RH |
| Storage Temperature and Humidity | −25 to 60° C., up to 90% RH |
| Excitation Source | |
| Source Emission | 280 ± 2 nm UVB, 340 ± 2 nm UVA, 450-850 nm VIS/NIR |
| Classification | Type BF applied part TBD |
| ANSI IESNA RP-27.3-96 Risk Group Classification and Labeling | RG-3 TBD |
| Mode of Operation | Pulse Width Modulation, 40 kHz base frequency |
| Output Power, from fiber | UVB −2 uW at 25% of max power, UVA 5 uW at 25% of max power, VIS/NIR 1 uW/3 nm |
| Ingress Protection Rating | IPX0 TBD |
| Spectrometer | |
| Light detection | 250 nm to 850 nm |
| Classification | Type BF applied part TBD |
| ANSI IESNA RP-27.3-96 Risk Group Classification and Labeling | TBD |
| Mode of Operation | TBD |
| Output Power, from fiber | 5 v DC ± 5% |
| Ingress Protection Rating | IPX0 TBD |
| Computer Control Unit | |
| CCU Subcomponents | |
| Motherboard | BCM Advanced Research MX81H |
| CPU | Intel Core i5-4570TE processor with Hyper-Threading |
| Operating System | CentOS 7 Linux |
| Software | Custom Application Software |
| Memory | 16 GB- 2 each Micron 8GBMT16KTF1G64HZ-1G6E1 SODIMM |
| Storage (internal) | Operating System Hard Drive mSATA- 128 GB SanDisk SD7SF6S-128G-1122 Patient Data Hard Drive 2.5 Solid State Drive- 512 GB SanDisk SD7SB7S-512G-1122 |
| Storage (external) | USB Flash Drive |
| WiFi | Intel Wireless-N 7260, IEEE 802.11b/g/n Wi-Fi plus |
| Touch Screen Display | Open Frame Display: Apollo Displays POS-Line 10.4" with True Flat Glass and Projective Capacitive touch screen |
| Power Supply | Medical AC/DC Power Supply: Murata 400 W 12 V Output AC/DC Power Supply Converter MVAC400-12AF |

TABLE 6-continued

System Specifications by Component

| | |
|---|---|
| Master Control Unit PCBA | Custom PCB assembly |
| Microcontroller | STMicroelectronics STM32F401 |
| Operating System | None- Custom software |
| Power Distribution PCBA | Custom PCB assembly |
| Applied Part EMC Filter PCBA | Custom PCB assembly |
| Graphical User Interface | Custom Software (TBD) |

Exemplary Operation

Mechanical biopsy of tissue and collection of spectra data based on the principle of auto-fluorescence, i.e., when energy is applied to tissue, the tissue emits light energy at a specific wavelength intensity and pattern. In fluorescence spectroscopy, one or more narrowband light sources are used to excite endogenous fluorophores and the emission spectrum at each excitation wavelength is detected. The auto-fluorescence spectra (AFS) depend on several important endogenous fluorophores such as tryptophan, collagen, nicotinamide adenine dinucleotide (NADH), flavin adenine dinucleotide (FAD), and others. Quantitative analysis of AFS obtained from tissue can provide valuable information regarding biochemical changes that correlate with disease status. In diffuse reflectance spectroscopy, light is delivered to tissue and after several successive scattering and absorption events it re-emerges from the tissue. Hence, diffuse reflectance spectra (DRS) have information regarding size and shape of cells and intracellular structures of tissue underneath. Refer to Appendix A, Mechanism of Action (Expanded), for additional mechanism of action details.

With the exception of the OBN 1262 there are no other device components that come in contact with the patient's blood or bodily fluids. The user (physician) is gloved while handling the OBN/Handpiece Assembly and the other system components (e.g. monitor).

Exemplary Principles of Operation

Use of the ClariCore™ System has been designed to follow standard TRUS biopsy procedures (FIG. 27).

When the biopsy procedure is complete, the Handpiece cables are removed from the Console and the entire Handpiece is disposed of in accordance with hospital standards. The protective film is removed from the monitor and disposed of in a biohazard waste container. The user can download the report information via an external USB storage device. The information will be stored on the console for future retrieval, if desired. The device is powered off with the power button (and confirmation of power off sequence is visible on the screen). Refer to Appendix B, Quick Reference Guide, for additional principle of operations details.

Exemplary Use/Indications for Use

The ClariCore™ System is designed to perform biopsies of the prostate and provide adjunctive tissue characterization. The optical spectroscopy component is primarily a documentation tool.

The ClariCore™ System is an in vivo real-time tissue-classifying biopsy system for targeted tissue biopsies. The system is indicated for intraoperative use as an adjunctive diagnostic tool during TRUS guided prostate biopsy. The system is intended to provide intra-operative tissue characterization of 'Normal' versus 'Suspicious' in vivo prostate tissue for subsequent excision. The system is to be used in facilitating targeted biopsy sampling (which includes submission for histological examination).

Non-/Pre-Clinical Testing

Bench, in vivo (animal), and ex vivo (human prostate and bovine) testing for the first generation of the ClariCore™ System were performed to validate and verify that the system satisfies the performance, functional, and safety requirements relative to the product specifications, risk analysis, and Instructions for Use. A series of non-clinical laboratory studies were performed and included testing related to the safety and performance of the first generation system. The testing included electrical safety/electromagnetic compatibility, software verification, mechanical and structural bench testing, biological evaluation, reliability, sterility and stability. Additionally, component and system level in vivo (animal) and ex vivo (human prostate and bovine) tissue testing demonstrated device performance.

Clinical Feasibility Study

The pre/non-clinical testing noted above were used to support an initial human, non-significant use clinical study—using the device in an open surgical setting immediately prior to a patient's already scheduled radical prostatectomy. In one form, the system comprises a core biopsy needle with fiber optics (optical biopsy needle), fluorometer, and laptop with operating software. The fiber optics were incorporated into a general-purpose biopsy needle. The system was used to collect optical spectral data and a correlative biopsy core from patients undergoing radical retropubic prostatectomy surgery.

The overall objective of the study was to acquire and analyze spectral data and correlative tissue biopsy cores using the investigational optical biopsy needle, fluorometer, and associated software. This objective was achieved by performing prostate biopsies immediately after optical spectral data was collected from each of the biopsy locations, on patients scheduled for radical retropubic prostatectomy surgery, just prior to removal of their prostate. The in vivo optical biopsies were performed during the surgery as an open procedure while the prostate was exposed with the blood vessels to the gland not yet severed. Additionally, ex vivo acquisition and analysis of spectral data and correlation of tissue biopsy cores were evaluated post-prostatectomy surgery. The initial effectiveness of the optical biopsy system and understanding of the inter-patient and intra-patient variations of tissue classification algorithm were evaluated.

Prostate biopsies were grouped into benign or malignant based on the histological findings within a measurement window 0.5 mm wide and located 1.7 mm from each core's distal-end. Partial Least Squares analysis of tissue spectra was performed to identify principal components (PCs) as potential classifiers. Using a linear support vector machine and a leave-one-out cross validation method, selected PCs were tested for their ability to classify benign vs. malignant prostatic tissue.

TABLE 10

List of Acronyms

| | |
|---|---|
| AFLS | Auto Fluorescence Lifetime Spectroscopy |
| AFS | Auto Fluorescence Spectra |
| ASAP | Atypical Small Acinar Proliferation |
| AUC | Area Under the Curve |
| CCU | Computer Control Unit |
| CMs | Contract Manufacturers |
| CT | X-ray Computed Tomography |
| DFMEA | Design Failure Mode Effects Analysis |
| DHF | Device History File |
| DMR | Device Master Record |
| DRS | Diffuse Reflectance Spectra |
| DU | Detection Unit |
| ESC | Excitation Source Controller |
| EU | Excitation Unit |
| FDA | Food & Drug Administration |
| FAD | Flavin Adenine Dinucleotide |
| GS | Gleason Score |
| GUI | Graphical User Interface |
| HGPIN | High-Grade Prostatic Intra-epithelial Neoplasia |
| IDE | Investigational Device Exemption |
| IEC | International Electrotechnical Commission |
| IHC | Immunohistochemical Staining |
| IRB | Institutional Review Board |
| ISO | International Organization for Standardization |
| HAS | Host Application Software |
| H&E | Hematoxylin and Eosin stain |
| HG | High Grade |
| KTC | Knowledge-based Tissue Classification |
| LED | Light Emitting Diodes |
| LG | Low Grade |
| LHR | Lot History Records |
| MCS | Master Controller Software |
| MCU | Master Control Unit |
| MR | Magnetic Resonance |
| Mp-MRI | Multiparametric Magnetic Resonance Imaging |
| MRI | Magnetic Resonance Imaging |
| NADH | Nicotinamide Adenine Dinucletide |
| OBN | Optical Biopsy Needle |
| OPC | Objective Performance Criteria |
| OS | Operating System |
| OTS | Off-the-Shelf |
| PB | Precision Biopsy LLC |
| PC | Principal Component |
| PET | Positron Emission Tomography |
| PFMEA | Process Failure Mode Effects Analysis |
| PIN | Prostatic Intra-epithelial Neoplasia |
| QMS | Quality Management System |
| ROC | Receiver Operating Curves |
| RRP | Radical Retropubic Prostatectomy |
| SAE | Serious Adverse Events |
| SMA | Sub-Miniature version A |
| SNR | Signal to Noise Ratio |
| SVM | Support Vector Machine |
| SW | Software |
| TCA | Tissue Classification Algorithm |
| TMB | Transperineal Mapping Biopsy |
| TRUS | Transrectal Ultrasound |
| UIS | User Interface Software |
| UV | Ultraviolet |

In one form, the system is for use with a tissue and comprises an optical probe array system having at least one or more optical probes for inserting into the tissue, for illuminating the tissue and for generating light signals corresponding to the illuminated tissue, and an imaging system for generating an image of the tissue based on the generated light signals. The optical probe imaging system comprises a motorized handheld device to move the probe and excite the tissue. The optical probe imaging system records responses based on location of the optical probe imaging system relate to the tissue. The optical probe imaging evaluates the generated light signals using a near real-time algorithm to provide classification of the tissue.

In one form, a method comprises positioning one or more optical light sources adjacent to or within tissue to illuminate the tissue, and capturing spectra or other optical phenomena from the illuminated tissue using a sensor. The method characterizes the tissue at the location of the optical sensor based on the captured spectra or other optical phenomena and determines corresponding coordinates of the tissue to map a 3D image of the tissue. The 3D optical image of the tissue is created based on the mapped 3D image. A motorized handheld device is used to move the sources within the tissue to excite the tissue. Responses of the sensor are recorded based on location of the sources relate to the tissue. The spectra or other optical phenomena from the illuminated tissue are evaluated using a near real-time algorithm to provide classification of the tissue.

In one form, the system is for use with a tissue and comprises an optical probe array system having at least one or more optical probes for illuminating the tissue and for generating light signals corresponding to the illuminated tissue fluorescence and/or corresponding to the illuminated tissue diffuse reflectance spectroscopy for distinguishing between cancer tissue and non-cancer tissue, a controller and display generating a light signal image corresponding to the generated light signals, an imaging system including a display generating an MRI or CT image indicative of the position of the optical probes relative to the tissue. The, imaging system includes an ultrasound imaging guidance system for identifying the position of the optical probes relative to the tissue wherein the imaging system generates a fused image on its display of the tissue based on the identified position of the optical probes as indicated by the MRI or CT imaging guidance system and as indicated by the ultrasound imaging guidance system wherein the fused image is a fusion of an MRI or CT image provided by the MRI or CT imaging guidance system and an ultrasound image provided by the ultrasound imaging guidance system. The optical probe imaging system comprises a motorized handheld device to move the probe and excite the tissue. The optical probe imaging system records responses based on location of the optical probe imaging system relate to the tissue. The optical probe imaging evaluates the generated light signals using a near real-time algorithm to provide classification of the tissue.

The Abstract and summary are provided to help the reader quickly ascertain the nature of the technical disclosure. They are submitted with the understanding that they will not be used to interpret or limit the scope or meaning of the claims. The summary is provided to introduce a selection of concepts in simplified form that are further described in the Detailed Description. The summary is not intended to identify features or essential features of the claimed subject matter, nor is it intended to be used as an aid in determining the claimed subject matter.

For purposes of illustration, programs and other executable program components, such as the operating system, are illustrated herein as discrete blocks. It is recognized, however, that such programs and components reside at various times in different storage components of a computing device, and are executed by a data processor(s) of the device.

Although described in connection with an exemplary computing system environment, embodiments of the aspects of the invention are operational with numerous other special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well-known computing systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the invention may be described in the general context of data and/or processor-executable instructions, such as program modules, stored one or more tangible, non-transitory storage media and executed by one or more processors or other devices. Generally, program modules include, but are not limited to, routines, programs, components, and data structures that perform particular tasks or implement particular abstract data types. Aspects of the invention may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the invention.

Embodiments of the aspects of the invention may be implemented with processor-executable instructions. The processor-executable instructions may be organized into one or more processor-executable components or modules on a tangible processor readable storage medium which is not a signal. Aspects of the invention may be implemented with any number and organization of such components or modules. For example, aspects of the invention are not limited to the specific processor-executable instructions or the specific components or modules illustrated in the figures and described herein. Other embodiments of the aspects of the invention may include different processor-executable instructions or components having more or less functionality than illustrated and described herein.

The order of execution or performance of the operations in embodiments of the aspects of the invention illustrated and described herein is not essential, unless otherwise specified. That is, the operations may be performed in any order, unless otherwise specified, and embodiments of the aspects of the invention may include additional or fewer operations than those disclosed herein. For example, it is contemplated that executing or performing a particular operation before, contemporaneously with, or after another operation is within the scope of aspects of the invention.

All references, including without limitation all papers, publications, presentations, texts, reports, manuscripts, brochures, internet postings, journal articles, periodicals, and the like, cited in this specification are hereby incorporated by reference. The discussion of the references herein is intended merely to summarize the assertions made by their authors and no admission is made that any reference constitutes prior art. The inventors reserve the right to challenge the accuracy and pertinence of the cited references.

It is intended that all patentable subject matter disclosed herein be claimed and that no such patentable subject matter be dedicated to the public. Thus, it is intended that the claims be read broadly in light of that intent. In addition, unless it is otherwise clear to the contrary from the context, it is intended that all references to "a" and "an" and subsequent corresponding references to "the" referring back to the antecedent basis denoted by "a" or "an" are to be read broadly in the sense of "at least one." Similarly, unless it is otherwise clear to the contrary from the context, the word "or," when used with respect to alternative named elements is intended to be read broadly to mean, in the alternative, any one of the named elements, any subset of the named elements or all of the named elements.

In view of the above, it will be seen that several advantages of the aspects of the invention are achieved and other advantageous results may be attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the invention by way of example and not by way of limitation. This description enables one skilled in the art to make and use the aspects of the invention, and describes several embodiments, adaptations, variations, alternatives and uses of the aspects of the invention, including what is presently believed to be the best mode of carrying out the aspects of the invention. Additionally, it is to be understood that the aspects of the invention is not limited in its application to the details of construction and the arrangement of components set forth in the following description or illustrated in the drawings. The aspects of the invention are capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of the invention as defined in the appended claims. It is contemplated that various changes could be made in the above constructions, products, and methods without departing from the scope of aspects of the invention. In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A method of evaluating a three dimensional image of at least a portion of a prostate of a patient, the method comprising:

positioning an optical probe configured to target a location within the prostate of the patient;

transmitting light from the optical probe toward the location and receiving fluorescence spectra by the optical probe from the location;

generating, by a tissue classification system, a diagnosis classification indicative of tissue condition of tissue at the location, the tissue classification system executing at least one algorithm that generates the diagnosis classification based only on selected data of the fluorescence spectra from the location; and generating a visual display of the image of the prostate and the diagnosis classification overlapping the image at the location so as to confirm or contradict the existence of a cancer lesion at the location.

2. A method as in claim 1, wherein the image comprises a magnetic resonance imaging (MRI) image, an ultrasound (US) image, or a computed tomography (CT) image or a multimodality (MMI image.

3. A method as in claim 1, wherein the image comprises an MRI/US fusion image.

4. A method as in claim 1, wherein the diagnosis classification is visualized on the visual display by a color indicating the diagnosis classification.

5. A method as in claim 1, further comprising selecting an option for the visual display, wherein the option comprises a black-and-white image, a color image, and/or a line image.

6. A method as in claim 1, wherein positioning the probe comprises introducing the probe under ultrasound, MRI or CT guidance.

7. A method as in claim 1, wherein the optical probe includes a biopsy needle, the method further comprising deploying the biopsy needle so af, configured to biopsy the location within the prostate if the visual display of the diagnosis classification confirms the existence of the cancer lesion at the location.

8. A method as in claim 7, wherein deploying the biopsy needle comprises activating an auto needle advancing mechanism.

9. A method as in claim 1, wherein the optical probe includes a treatment modality, the method further comprising activating the treatment modality so as to treat the location within the prostate if the visual display of the diagnosis classification confirms the existence of the cancer lesion at the location.

10. A method as in claim 9, wherein the treatment modality comprises cryotherapy, photodynamic therapy, brachytherapy, high-intensity focused ultrasound (HIFU) therapy, ablation therapy, laser ablation therapy, radio frequency (RFI ablation therapy, vapor ablation therapy or local drug delivery.

11. A method as in claim 1, wherein the image indicates a plurality of locations within the prostate of the patient having potential presence of cancer lesions, the method further comprising repeating the method of evaluating the image at each of the plurality of locations.

12. A method as in claim 11, wherein the optical probe includes a biopsy needle, the method further comprising deploying the biopsy needle so af, configured to biopsy each of the plurality of locations having a correlated visual display of diagnosis classification confirming the existence of the cancer lesion and skipping deploying the biopsy needle at each of the plurality of locations having a correlated visual display of diagnosis classification contradicting the existence of the cancer lesion.

13. A method as in claim 11, wherein the optical probe includes a treatment modality, the method further comprising activating the treatment modality so as to treat each of the plurality of locations having a correlated visual display of diagnosis classification confirming the existence of the cancer lesion and skipping activating the treatment modality at each of the plurality of locations having a correlated visual display of diagnosis classification contradicting the existence of the cancer lesion.

14. A method as in claim 1, wherein the fluorescence spectra is generated from endogenous fluorophores.

15. A method as in claim 14, wherein the endogenous fluorophores comprise amino acids, tryptophan, tyrosine, phenylalanine, structural proteins, collagen, elastin, enzymes, coenzymes, flavin adenine dinucleotide (FAD), flavins, nicotinamide adenine dinucleotide (NADH), nicotinamide adenine dinucleotide phosphate (NADPH), vitamins, vitamin A, vitamin K, vitamin D, vitamin B6, compounds, pyridoxine, pyridoxamone, pyridoxal, pyridoxic acid, pyridoxal 5'-phosphate, vitamin B12, lipids, phospholipids, lipofuscin, ceroid, and/or porphyrins.

16. A method as in claim 1, wherein the image indicates a potential presence of a cancer lesion at at least one additional location within the prostate of the patient, the method further comprising re-positioning the optical probe configured to target the at least one additional location within the prostate of the patient, transmitting light from the optical probe toward the at least one additional location and receiving fluorescence spectra by the optical probe from the at least one additional location, generating, by the tissue classification system, an additional diagnosis classification indicative of tissue condition of tissue at the at least one additional location, the tissue classification system executing the at least one algorithm that generates the additional diagnosis classification based only on selected data of the fluorescence spectra from the at least one additional location, and generating a visual display of the additional diagnosis classification overlapping the image at the at least one additional location so as to confirm or contradict the existence of the cancer lesion at the at least one additional location.

* * * * *